(12) United States Patent
Camarero Palao et al.

(10) Patent No.: US 10,988,522 B2
(45) Date of Patent: Apr. 27, 2021

(54) PROTEOLICALLY RESISTANT CYCLOTIDES WITH ANGIOTENSIN 1-7 LIKE ACTIVITY

(71) Applicant: University of Southern California, Los Angeles, CA (US)

(72) Inventors: Julio A. Camarero Palao, San Gabriel, CA (US); Teshome L. Aboye, Los Angeles, CA (US); Kathleen E. Rodgers, Los Angeles, CA (US)

(73) Assignee: UNIVERSITY OF SOUTHERN CALIFORNIA, Los Angeles (GA)

( * ) Notice: Subject to any disclaimer, the term of this patent is extended or adjusted under 35 U.S.C. 154(b) by 0 days.

(21) Appl. No.: 16/232,985

(22) Filed: Dec. 26, 2018

(65) Prior Publication Data

US 2019/0359674 A1 Nov. 28, 2019

Related U.S. Application Data

(63) Continuation of application No. 15/422,376, filed on Feb. 1, 2017, now abandoned.

(60) Provisional application No. 62/290,329, filed on Feb. 2, 2016.

(51) Int. Cl.
*C07K 14/575* (2006.01)
*C07K 14/00* (2006.01)

(52) U.S. Cl.
CPC .......... *C07K 14/575* (2013.01); *C07K 14/001* (2013.01)

(58) Field of Classification Search
CPC .............................. C07K 14/575; C07K 14/001
See application file for complete search history.

(56) References Cited

U.S. PATENT DOCUMENTS

| | | | |
|---|---|---|---|
| 7,018,801 B2 | 3/2006 | Kodadek | |
| 7,476,500 B1 | 1/2009 | Liu et al. | |
| 2002/0049162 A1 | 4/2002 | Rodgers et al. | |
| 2002/0146823 A1 | 10/2002 | Rodgers et al. | |
| 2003/0203834 A1* | 10/2003 | Tailant | A61P 35/02 514/1 |
| 2010/0189682 A1 | 7/2010 | Schellenberger et al. | |
| 2012/0230947 A1* | 9/2012 | Schellenberger | C07K 7/06 424/85.2 |
| 2012/0244575 A1* | 9/2012 | Poth | C07K 14/415 435/68.1 |
| 2013/0330352 A1* | 12/2013 | Akita | A61P 9/10 424/145.1 |
| 2014/0356326 A1* | 12/2014 | Schellenberger | C07K 7/06 424/85.7 |
| 2014/0369930 A1* | 12/2014 | Gruber | A61K 38/168 424/1.69 |
| 2016/0096895 A1* | 4/2016 | Campbell | C07K 16/2866 424/172.1 |
| 2016/0280753 A1* | 9/2016 | Schellenberger | C07K 7/06 |
| 2017/0239327 A9 | 8/2017 | Gruber et al. | |

FOREIGN PATENT DOCUMENTS

WO WO-2011/005598 A1 1/2011
WO WO-2014/046732 A1 3/2014

OTHER PUBLICATIONS

Huang et al., 2015, Optimization of the cyclotide framework to improve cell penetration properties, Frontiers in Pharmacology, 6(17): 1-7.*
Durik et al., 2012, The Effect of the Thioether-Bridged, Stabilized Angiotensin-(1-7) Analogue Cyclic Ang-(1-7) on Cardiac Remodeling and Endothelial Function in Rats with Myocardial Infraction, International Journal of Hypertension, 2012: 8 pages.*
Jagadish et al., 2010, Cyclotides, a promising molecular scaffold for peptide-based therapeutics, Biopolymers, 94(5): 611-616.*
Gould et al., 2011, Cyclotides, a novel ultrastable polypeptide scaffold fordrug discovery, Curr Pharm Des, 17(38): 4294-4307.*
Vinson et al., 2012, The renin-angiotensin system in the breast and breast cancer, Endocrine-Related Cancer, 19: R1-R19.*
Ferreira et al., 2012, New Cardiovascular and Pulmonary Therapeutic Strategies Based on the Angiotensin-Converting Enzyme 2/Angiotensin-(1-7)/MAS Receptor Axis.*
Aboye, et al., "Design of a MCoTI-bsaed Cyclotide with Angiotensin 1-7-like Activity", Molecules, 2016, 21(2), 14 pages.
Baldwin, Michael, "Protein Identification by Mass Spectrometry", Molecular &Cellular Proteomics, Nov. 6, 2003, 3.1, pp. 1-9.
Bernal et al., "A Stapled p53 Helix Overcomes HDMX-Mediated Suppression of p53" Cancer Cell 18:411-422 (2010).
Camarero, et al., "A Cell-Based Approach for the Biosynthesis/ Screening of Cyclic Peptide Libraries against Bacterial Toxins", Chemistry Today, May 1, 2007, Report No. UCRL-JRNL-235916, pp. 1-8.
Camarero, et al., "Biosynthesis of a Fully Functional Cyclotide inside Living Bacterial Cells", ChemBioChem Supporting Information, 2007, 8, pp. 1-9.
Daly, et al., "Discovery, structure and biological activities of cyclotides", Adv Drug Deliv Rev 2009, 61, 918-930.
Gallagher, et al., "Angiotensin peptides and lung cancer", Current cancer drug targets 2011, 11, 394-404.
Gallagher, et al., "Inhibition of human lung cancer cell growth by angiotensin-(1-7)", Carcinogenesis 2004, 25, 2045-2052.
Garcia, et al., "Biological activities of natural and engineered cyclotides, a novel molecular scaffold for peptide-based therapeutics", Current molecular pharmacology, 2010, vol. 3, No. 3, pp. 153-163.
Huang, et al., "Design of substrate-based BCR-ABL kinase inhibitors using the cyclotide scaffold", Scientific Reports, 2015, 5: 12974, 15 pages.
Iusuf, et al., "Angiotensin-(1-7): Pharmacological properties and pharmacotherapeutic perspectives", European journal of pharmacology 2008, 585, 303-312.

(Continued)

*Primary Examiner* — Amber D Steele
(74) *Attorney, Agent, or Firm* — Foley & Lardner LLP

(57) ABSTRACT

Described herein is a novel cyclotide able to activate the unique receptor of angiotensin-(1-7) (AT1-7), the MAS1 receptor. This cyclotide may be used in the treatment of cancer and myocardial infarction.

36 Claims, 7 Drawing Sheets

Specification includes a Sequence Listing.

(56) References Cited

OTHER PUBLICATIONS

Jagadish, et al., "Expression of fluorescent cyclotides using protein trans-splicing for easy monitoring of cyclotide-protein interactions", Angewandte Chemie International Edition, 2013, vol. 52, No. 11, pp. 3126-3131.

Ji, et al., "In vivo activation of the p53 tumor suppressor pathway by an engineered cyclotide", J Am Chem Soc 2013, 135, 11623-11633.

Kempe, et al., "Intein-mediated protein assembly in transgenic wheat: production of active barnase and acetolactate synthase from split genes", Plant Biotechnology Journal, Apr. 2009, PubMed: 19222807, vol. 7, No. 3, pp. 283-297, XP002542925.

Kimura, et al., "Biosynthesis of the cyclotide Kalata B1 by using protein splicing", Angewandte Chemie (International Ed. in English), Jan. 30, 2006, PubMed: 16381044, vol. 45, No. 6, pp. 973-976.

Kimura, et al., "Development of a cell-based fluorescence resonance energy transfer reporter for Bacillus anthracis lethal factor protease", Analytical Biochemistry, 2007, 369, pp. 60-70.

Loot, et al., "Angiotensin-(1-7) attenuates the development of heart failure after myocardial infarction in rats", Circulation 2002, J05, 1548-1550.

Menon, et al., "Angiotensin-(1-7) inhibits growth of human lung adenocarcinoma xenografts in nude mice through a reduction in cyclooxygenase-2", Cancer Res 2007, 67, 2809-2815.

Mootz, et al., "Conditional Protein Splicing: A New Tool to Control Protein Structure and Function in Vitro and in Vivo", Journal of the American Chemical Society, 2003, 125, pp. 10561-10569.

Notice of Allowance dated Sep. 27, 2018, from U.S. Appl. No. 15/422,376.

Puttamadappa, et al. "Backbone dynamics of cyclotide mcoti-i free and complexed with trypsin", Angew Chem Int Ed Engl 2010, 49, 7030-7034.

Sancheti, et al., ""Splicing up" drug discovery. Cell-based expression and screening of genetically-encoded libraries of backbone-cyclized polypeptides", Advanced Drug Delivery Reviews, vol. 61, No. 11, Jun. 21, 2009, pp. 908-917, XP002604781.

Scott, et al., "Production of cyclic peptides and proteins in vivo", PNAS, 1999, vol. 96, No. 24, pp. 13638-13643.

Scott, et al., "Structural requirements for the biosynthesis of backbone cyclic peptide libraries", Chemistry and Biology, 2001, vol. 8, pp. 801-815.

Tallant, et al., "Molecular mechanisms of inhibition of vascular growth by angiotensin-(1-7)", Hypertension 2003, 42, 574-579.

Tan, Song, "A Modular Polycistronic Expression System for Overexpressing Protein Complexes in *Escherichia coli*", Protein Expression and Purification, 2001, 21, pp. 224-234.

Tavassoli, et al., "Inhibition of HIV Budding by a Genetically Selected Cyclic Peptide Targeting the Gag-TSG101 Interaction", ACS Chemical Biology, vol. 3, No. 12, Dec. 2008, pp. 757-764, XP002604780.

Tavassoli, et al., "Split-intein mediated circular ligation used in the synthesis of cyclic peptide libraries in *E. coli*", Nature Protocols, 2007, vol. 2, No. 5, pp. 1126-1133.

U.S. Final Office Action dated Apr. 25, 2014, from U.S. Appl. No. 13/379,340.

Wang, et al., "Circulating rather than cardiac angiotensin-(1-7) stimulates cardioprotection after myocardial infarction", Circ Heart Fail 2010, 3, 286-293.

You, et al., "Intracellular protein interaction mapping with FRET hybrids", Proceedings of the National Academy of Sciences of the United States of America, vol. 103, No. 49, Dec. 2006, pp. 18458-18463, XP002604779.

Young, et al., "Evolution of cyclic peptide protease inhibitors", PNAS, 2011, vol. 108, No. 27, pp. 11052-11056.

Camarero, "Screening and Selection of New Antagonists of the RING-Mediated Hdm2/Hdmx Interaction", Annual Report, DTIC Online, Accession No. ADA560756, Mar. 1, 2011, 126 pages.

Aboye, et al., "Design of a MCoTI-Based Cyclotide with Angiotensin (1-7)-Like Activity" Molecules, 21, 15, Jan. 26, 2016, 10 pages.

\* cited by examiner

MCoTI-I

```
        1          10          20          30
    ┌GGVCPKILQRCRRDSDCPGACICRGNGYCGSGSD┐
      loop 1 | loop 2 | loop 3 |  loop 5  | loop 6
```

+

AT1-7    H-DRVYIP-OH

↓

MCo-AT1-7

HO-EIYVRX-αNH₂

```
        1          10          20          30
    ┌GGVCPKILQRCRRDSDCPGACICRGNGYCGSG┐
      loop 1 | loop 2 | loop 3 |  loop 5  | loop 6
```

FIG. 1

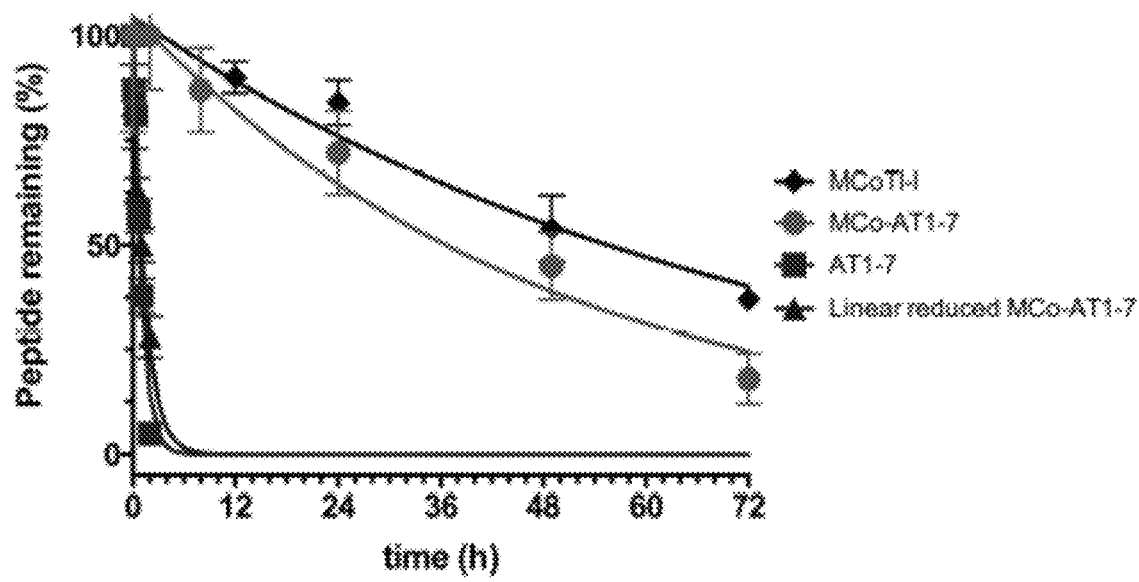
FIG. 7
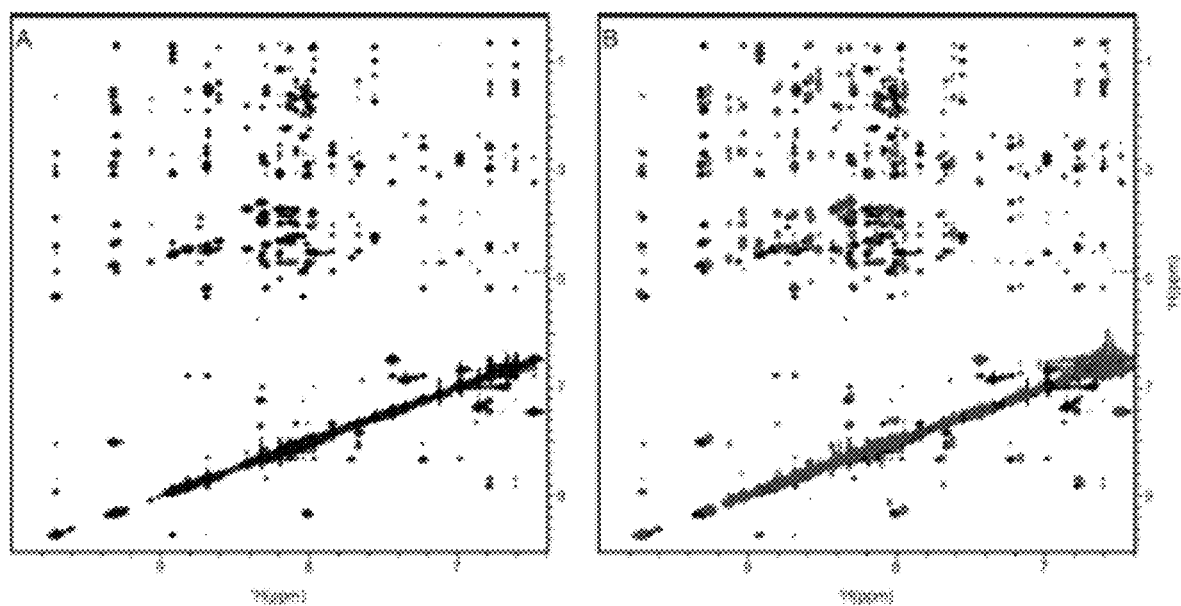
FIGS. 8A-B

SEQUENCE LISTING

<160> NUMBER OF SEQ ID NOS: 302

<210> SEQ ID NO 1
<211> LENGTH: 325
<212> TYPE: PRT
<213> ORGANISM: Homo sapiens

<400> SEQUENCE: 1

Met Asp Gly Ser Asn Val Thr Ser Phe Val Val Glu Glu Pro Thr Asn
1               5                   10                  15

Ile Ser Thr Gly Arg Asn Ala Ser Val Gly Asn Ala His Arg Gln Ile
            20                  25                  30

Pro Ile Val His Trp Val Ile Met Ser Ile Ser Pro Val Gly Phe Val
            35                  40                  45

Glu Asn Gly Ile Leu Leu Trp Phe Leu Cys Phe Arg Met Arg Arg Asn
50                  55                  60

Pro Phe Thr Val Tyr Ile Thr His Leu Ser Ile Ala Asp Ile Ser Leu
65                  70                  75                  80

Leu Phe Cys Ile Phe Ile Leu Ser Ile Asp Tyr Ala Leu Asp Tyr Glu
                85                  90                  95

Leu Ser Ser Gly His Tyr Tyr Thr Ile Val Thr Leu Ser Val Thr Phe
            100                 105                 110

Leu Phe Gly Tyr Asn Thr Gly Leu Tyr Leu Leu Thr Ala Ile Ser Val
            115                 120                 125

Glu Arg Cys Leu Ser Val Leu Tyr Pro Ile Trp Tyr Arg Cys His Arg
130                 135                 140

Pro Lys Tyr Gln Ser Ala Leu Val Cys Ala Leu Leu Trp Ala Leu Ser
145                 150                 155                 160

Cys Leu Val Thr Thr Met Glu Tyr Val Met Cys Ile Asp Arg Glu Glu
                165                 170                 175

Glu Ser His Ser Arg Asn Asp Cys Arg Ala Val Ile Ile Phe Ile Ala
            180                 185                 190

Ile Leu Ser Phe Leu Val Phe Thr Pro Leu Met Leu Val Ser Ser Thr
            195                 200                 205

Ile Leu Val Val Lys Ile Arg Lys Asn Thr Trp Ala Ser His Ser Ser
210                 215                 220

Lys Leu Tyr Ile Val Ile Met Val Thr Ile Ile Phe Leu Ile Phe
225                 230                 235                 240

Ala Met Pro Met Arg Leu Leu Tyr Leu Leu Tyr Tyr Glu Tyr Trp Ser
                245                 250                 255

Thr Phe Gly Asn Leu His His Ile Ser Leu Leu Phe Ser Thr Ile Asn
            260                 265                 270

Ser Ser Ala Asn Pro Phe Ile Tyr Phe Phe Val Gly Ser Ser Lys Lys
            275                 280                 285

Lys Arg Phe Lys Glu Ser Leu Lys Val Val Leu Thr Arg Ala Phe Lys
290                 295                 300

Asp Glu Met Gln Pro Arg Arg Gln Lys Asp Asn Cys Asn Thr Val Thr
305                 310                 315                 320

Val Glu Thr Val Val
                325

<210> SEQ ID NO 2
<211> LENGTH: 34
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 2

Gly Gly Asx Cys Pro Lys Ile Leu Gln Arg Cys Arg Arg Asp Ser Asp
1               5                   10                  15

Cys Pro Gly Ala Cys Ile Cys Arg Gly Ala Gly Tyr Cys Gly Ser Gly
            20                  25                  30

Ser Asp

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Gly Val Cys Pro Lys Ile Leu Gln Arg Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Gly Asx Cys Pro Lys Ile Leu Gln Arg Cys Arg Arg Asp Ser Asp
1               5                   10                  15

Cys Pro Gly Ala Cys Ile Cys Arg Gly Ala Gly Tyr Cys Gly Ser Gly
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Gly Val Cys Pro Lys Ile Leu Gln Arg Cys Arg Arg Asp Ser Asp
1               5                   10                  15

Cys Pro Gly Ala Cys Ile Cys Arg Gly Asn Gly Tyr Cys Gly Ser Gly
            20                  25                  30

<210> SEQ ID NO 6
<211> LENGTH: 1926
<212> TYPE: DNA
<213> ORGANISM: Homo sapiens

<400> SEQUENCE: 6
gttgttctgg gtactacagc agaagggtat gcggaagcga gcaccccagt ctgagatggc      60
tcctgccggt gtgagcctga gggccaccat cctctgcctc ctggcctggg ctggcctggc     120
tgcaggtgac cgggtgtaca tacccccctt ccacctcgtc atccacaatg agagtacctg     180

-continued

```
tgagcagctg gcaaaggcca atgccgggaa gcccaaagac cccaccttca tacctgctcc      240
aattcaggcc aagacatccc ctgtggatga aaaggcccta caggaccagc tggtgctagt      300
cgctgcaaaa cttgacaccg aagacaagtt gagggccgca atggtcggga tgctggccaa      360
cttcttgggc ttccgtatat atggcatgca cagtgagcta tggggcgtgg tccatggggc      420
caccgtcctc tccccaacgg ctgtctttgg caccctggcc tctctctatc tgggagcctt      480
ggaccacaca gctgacaggc tacaggcaat cctgggtgtt ccttggaagg acaagaactg      540
cacctcccgg ctggatgcgc acaaggtcct gtctgccctg caggctgtac agggcctgct      600
agtggcccag gcagggctg atagccaggc ccagctgctg ctgtccacgg tggtgggcgt       660
gttcacagcc ccaggcctgc acctgaagca gccgtttgtg cagggcctgg ctctctatac      720
ccctgtggtc ctcccacgct ctctggactt cacagaactg gatgttgctg ctgagaagat      780
tgacaggttc atgcaggctg tgacaggatg gaagactggc tgctcccctga cgggagccag     840 tgtggacagc accctggctt tcaacaccta cgtccacttc aaggaaga tgaagggctt        900 ctccctgctg gccgagcccc aggagttctg ggtggacaac agcacctcag tgtctgttcc      960
catgctctct ggcatgggca ccttccagca ctggagtgac atccaggaca acttctcggt     1020
gactcaagtg tccttcactg agagcgcctg cctgctgctg atccagcctc actatgcctc     1080
tgacctggac aaggtggagg gtctcacttt ccagcaaaac tccctcaact ggatgaagaa     1140
actgtctccc cggaccatcc acctgaccat gccccaactg gtgctgcaag atcttatga     1200 cctgcaggac ctgctcgccc aggctgagct gcccgccatt ctgcacaccg agctgaacct     1260
gcaaaaattg agcaatgacc gcatcagggt ggggggaggtg ctgaacagca ttttttttga    1320
gcttgaagcg gatgagagag agcccacaga gtctacccaa cagcttaaca agcctgaggt     1380
cttggaggtg accctgaacc gcccattcct gtttgctgtg tatgatcaaa gcgccactgc     1440
cctgcacttc ctgggccgcg tggccaaccc gctgagcaca gcatgaggcc agggccccag     1500
aacacagtgc ctggcaaggc ctctgccct ggcctttgag gcaaaggcca gcagcagata      1560
acaaccccgg acaaatcagc gatgtgtcac ccccagtctc ccaccttttc ttctaatgag     1620
tcgactttga gctggaaagc agccgtttct ccttggtcta gtgtgctgc atggagtgag      1680 cagtagaagc ctgcagcggc acaaatgcac ctcccagttt gctgggttta ttttagagaa     1740
tgggggtggg gaggcaagaa ccagtgttta gcgcgggact actgttccaa aaagaattcc     1800
aaccgaccag cttgtttgtg aaacaaaaaa gtgttccctt ttcaagttga gaacaaaaat     1860
tgggttttaa aattaaagta tacatttttg cattgcaaaa aaaaaaaaaa aaaaaaaaa      1920 aaaaaa                                                                 1926
```

<210> SEQ ID NO 7
<211> LENGTH: 10
<212> TYPE: PRT
<213> ORGANISM: Homo sapiens

<400> SEQUENCE: 7

Asp Arg Val Tyr Ile His Pro Phe His Leu
1               5                   10

<210> SEQ ID NO 8
<211> LENGTH: 8
<212> TYPE: PRT
<213> ORGANISM: Homo sapiens

<400> SEQUENCE: 8

```
Asp Arg Val Tyr Ile His Pro Phe
1               5

<210> SEQ ID NO 9
<211> LENGTH: 7
<212> TYPE: PRT
<213> ORGANISM: Homo sapiens

<400> SEQUENCE: 9

Arg Val Tyr Ile His Pro Phe
1               5

<210> SEQ ID NO 10
<211> LENGTH: 6
<212> TYPE: PRT
<213> ORGANISM: Homo sapiens

<400> SEQUENCE: 10

Val Tyr Ile His Pro Phe
1               5

<210> SEQ ID NO 11
<211> LENGTH: 7
<212> TYPE: PRT
<213> ORGANISM: Homo sapiens

<400> SEQUENCE: 11

Asp Arg Val Tyr Ile His Pro
1               5

<210> SEQ ID NO 12
<211> LENGTH: 6
<212> TYPE: PRT
<213> ORGANISM: Homo sapiens

<400> SEQUENCE: 12

Asp Arg Val Tyr Ile Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-2,3-diaminopropionic acid

<400> SEQUENCE: 13

Xaa Arg Val Tyr Ile Glu
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-2,3-diaminopropionic acid
```

```
<400> SEQUENCE: 14

Xaa Arg Val Tyr Ile His Glu
1               5

<210> SEQ ID NO 15
<211> LENGTH: 5
<212> TYPE: PRT
<213> ORGANISM: Homo sapiens

<400> SEQUENCE: 15

Asp Arg Val Tyr Ile
1               5

<210> SEQ ID NO 16
<211> LENGTH: 4
<212> TYPE: PRT
<213> ORGANISM: Homo sapiens

<400> SEQUENCE: 16

Asp Arg Val Tyr
1

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Gly Val Cys Pro Lys Ile Leu Gln Arg Cys Arg Arg Asp Ser Asp
1               5                   10                  15

Cys Pro Gly Ala Cys Ile Cys Arg Gly Asn Gly Tyr Cys Gly Ser Gly
            20                  25                  30

Asp Arg Val Tyr Ile His Pro
        35

<210> SEQ ID NO 18
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Gly Val Cys Pro Lys Ile Leu Gln Arg Cys Arg Arg Asp Ser Asp
1               5                   10                  15

Cys Pro Gly Ala Cys Ile Cys Arg Gly Asn Gly Tyr Cys Gly Ser Gly
            20                  25                  30

Asp Arg Val Tyr Ile Pro
        35

<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: L-2,3-diaminopropionic acid
```

<400> SEQUENCE: 19

Gly Gly Val Cys Pro Lys Ile Leu Gln Arg Cys Arg Arg Asp Ser Asp
1               5                   10                  15

Cys Pro Gly Ala Cys Ile Cys Arg Gly Asn Gly Tyr Cys Gly Ser Gly
            20                  25                  30

Xaa Arg Val Tyr Ile Glu
        35

<210> SEQ ID NO 20
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: L-2,3-diaminopropionic acid

<400> SEQUENCE: 20

Gly Gly Val Cys Pro Lys Ile Leu Gln Arg Cys Arg Arg Asp Ser Asp
1               5                   10                  15

Cys Pro Gly Ala Cys Ile Cys Arg Gly Asn Gly Tyr Cys Gly Ser Gly
            20                  25                  30

Xaa Arg Val Tyr Ile His Glu
        35

<210> SEQ ID NO 21
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Ile Pro Cys Ala Glu Ser Cys Val Tyr Ile Pro Cys Thr Val Thr
1               5                   10                  15

Ala Leu Leu Gly Cys Ser Cys Ser Asn Arg Val Cys Tyr Asn
            20                  25                  30

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 23

Gly Leu Pro Val Cys Gly Glu Thr Cys Phe Gly Gly Thr Cys Asn Thr
1               5                   10                  15

Pro Gly Cys Ser Cys Thr Trp Pro Ile Cys Thr Arg Asp
            20                  25

<210> SEQ ID NO 24
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Asp Pro Thr Phe Cys Gly Glu Thr Cys Arg Val Ile Pro Val Cys
1               5                   10                  15

Thr Tyr Ser Ala Ala Leu Gly Cys Thr Cys Asp Asp Arg Ser Asp Gly
            20                  25                  30

Leu Cys Lys Arg Asn
        35

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Ile Pro Cys Ala Glu Ser Cys Val Trp Ile Pro Cys Thr Val Thr
1               5                   10                  15

Ala Leu Leu Gly Cys Ser Cys Ser Asn Lys Val Cys Tyr Asn
            20                  25                  30

<210> SEQ ID NO 26
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Gly Thr Ile Phe Asp Cys Gly Glu Ser Cys Phe Leu Gly Thr Cys
1               5                   10                  15

Tyr Thr Lys Gly Cys Ser Cys Gly Glu Trp Lys Leu Cys Tyr Gly Thr
            20                  25                  30

Asn

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Ile Pro Cys Gly Glu Ser Cys Val Trp Ile Pro Cys Ile Ser Ala
1               5                   10                  15

Ala Leu Gly Cys Ser Cys Lys Asn Lys Val Cys Tyr Arg Asn
```

```
            20                  25                  30

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 29
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 30
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 31
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 32

Leu Pro Val Cys Gly Glu Thr Cys Val Gly Gly Thr Cys Asn Thr Pro
1               5                   10                  15

Gly Cys Thr Cys Ser Trp Pro Val Cys Thr Arg Asn
            20                  25

<210> SEQ ID NO 33
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Cys Val Gly Gly Thr Cys Asn Thr Pro Gly Cys Thr Cys Ser Trp
1               5                   10                  15

Pro Val Cys Thr Arg Asn Leu Pro Val Cys Gly
            20                  25

<210> SEQ ID NO 34
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Thr Cys Asn Thr Pro Gly Cys Thr Cys Ser Trp Pro Val Cys Thr
1               5                   10                  15

Arg Asn Gly Leu Pro Val Cys Gly Glu Thr Cys Val Gly
            20                  25

<210> SEQ ID NO 35
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Cys Thr Cys Ser Trp Pro Val Cys Thr Arg Asn Gly Leu Pro Val
1               5                   10                  15

Cys Gly Glu Thr Cys Val Gly Gly Thr Cys Asn
            20                  25

<210> SEQ ID NO 36
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Ser Trp Pro Val Cys Thr Arg Asn Gly Leu Pro Val Cys Gly Glu
1               5                   10                  15

Thr Cys Val Gly Gly Thr Cys Asn Thr Pro Gly Cys
            20                  25

<210> SEQ ID NO 37
<211> LENGTH: 27

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Cys Thr Arg Asn Gly Leu Pro Val Cys Gly Glu Thr Cys Val Gly
1               5                   10                  15

Gly Thr Cys Asn Thr Pro Gly Cys Thr Cys Ser
            20                  25

<210> SEQ ID NO 38
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Cys Gly Glu Thr Cys Val Gly Gly Thr Cys Asn Thr Pro Gly Cys
1               5                   10                  15

Thr Cys Ser Trp Pro Val Cys Thr
            20

<210> SEQ ID NO 39
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Asn Gly Leu Pro Val Cys Gly Glu Thr Cys Val Gly Gly Thr Cys
1               5                   10                  15

Asn Thr Pro Gly Cys Thr Cys Ser Trp Pro Val Cys Thr
            20                  25

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Ile Pro Cys Gly Glu Ser Cys Val Trp Ile Pro Cys Ile Ser Ser
1               5                   10                  15

Ala Ile Gly Cys Ser Cys Lys Ser Lys Val Cys Tyr Arg Asn
            20                  25                  30

<210> SEQ ID NO 41
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Cys Gly Glu Thr Cys Val Gly Gly Thr Cys Asn Thr Pro Gly Cys
1               5                   10                  15
```

Thr Cys Ser Trp Pro Val Cys Thr
            20

<210> SEQ ID NO 42
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Leu Pro Val Ala Gly Glu Thr Cys Val Gly Gly Thr Cys Asn Thr
1               5                   10                  15

Pro Gly Ala Thr Cys Ser Trp Pro Val Cys Thr Arg Asn
            20                  25

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Leu Pro Thr Cys Gly Glu Thr Cys Phe Gly Gly Thr Cys Asn Thr
1               5                   10                  15

Pro Gly Cys Ser Cys Ser Ser Trp Pro Ile Cys Thr Arg Asn
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gly Leu Pro Thr Cys Gly Glu Thr Cys Phe Gly Gly Thr Cys Asn Thr
1               5                   10                  15

Pro Gly Cys Thr Cys Asp Pro Trp Pro Ile Cys Thr Arg Asp
            20                  25                  30

<210> SEQ ID NO 45
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Leu Pro Val Cys Gly Glu Thr Cys Thr Leu Gly Thr Cys Tyr Thr
1               5                   10                  15

Gln Gly Cys Thr Cys Ser Trp Pro Ile Cys Lys Arg Asn
            20                  25

<210> SEQ ID NO 46
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gly Thr Leu Pro Cys Gly Glu Ser Cys Val Trp Ile Pro Cys Ile Ser
1               5                   10                  15

Ser Val Val Gly Cys Ser Cys Lys Ser Lys Val Cys Tyr Lys Asn
            20                  25                  30

<210> SEQ ID NO 47
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gly Thr Leu Pro Cys Gly Glu Ser Cys Val Trp Ile Pro Cys Ile Ser
1               5                   10                  15

Ala Val Val Gly Cys Ser Cys Lys Ser Lys Val Cys Tyr Lys Asn
            20                  25                  30

<210> SEQ ID NO 48
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asp
            20                  25

<210> SEQ ID NO 49
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Ala Pro Ile Cys Gly Glu Ser Cys Phe Thr Gly Lys Cys Tyr Thr
1               5                   10                  15

Val Gln Cys Ser Cys Ser Trp Pro Val Cys Thr Arg Asn
            20                  25

<210> SEQ ID NO 50
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ser Ile Pro Cys Gly Glu Ser Cys Val Phe Ile Pro Cys Thr Val Thr
1               5                   10                  15

Ala Leu Leu Gly Cys Ser Cys Lys Ser Lys Val Cys Tyr Lys Asn
            20                  25                  30

<210> SEQ ID NO 51

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Ile Pro Cys Gly Glu Ser Cys Val Tyr Ile Pro Cys Leu Thr Ser
1               5                   10                  15

Ala Ile Gly Cys Ser Cys Lys Ser Lys Val Cys Tyr Arg Asn
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Ile Pro Cys Gly Glu Ser Cys Val Trp Ile Pro Cys Leu Thr Ser
1               5                   10                  15

Ala Val Gly Cys Ser Cys Lys Ser Lys Val Cys Tyr Arg Asn
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Ser Ile Pro Cys Ala Glu Ser Cys Val Tyr Ile Pro Cys Phe Thr
1               5                   10                  15

Gly Ile Ala Gly Cys Ser Cys Lys Asn Lys Val Cys Tyr Tyr Asn
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Ile Pro Cys Gly Glu Ser Cys Val Trp Ile Pro Cys Ile Thr Ser
1               5                   10                  15

Ala Ile Gly Cys Ser Cys Lys Ser Lys Val Cys Tyr Arg Asn
            20                  25                  30

<210> SEQ ID NO 55
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Leu Pro Val Cys Gly Glu Thr Cys Val Gly Gly Thr Cys Asn Thr
1               5                   10                  15
```

Pro Gly Cys Ser Cys Ser Trp Pro Val Cys Thr Arg Asn
            20                  25

<210> SEQ ID NO 56
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Leu Pro Ile Cys Gly Glu Thr Cys Val Gly Gly Thr Cys Asn Thr
1               5                   10                  15

Pro Gly Cys Ser Cys Ser Trp Pro Val Cys Thr Arg Asn
            20                  25

<210> SEQ ID NO 57
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Leu Pro Val Cys Gly Glu Thr Cys Thr Leu Gly Lys Cys Tyr Thr
1               5                   10                  15

Ala Gly Cys Ser Cys Ser Trp Pro Val Cys Tyr Arg Asn
            20                  25

<210> SEQ ID NO 58
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Ser Ile Pro Cys Ala Glu Ser Cys Val Tyr Ile Pro Cys Ile Thr
1               5                   10                  15

Gly Ile Ala Gly Cys Ser Cys Lys Asn Lys Val Cys Tyr Tyr Asn
            20                  25                  30

<210> SEQ ID NO 59
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 60
<211> LENGTH: 30
<212> TYPE: PRT
<213> ORGANISM: Artificial Sequence
<220> FEATURE:
<223> OTHER INFORMATION: Description of Artificial Sequence: Synthetic

```
                       polypeptide

<400> SEQUENCE: 60

Gly Ile Pro Cys Ala Glu Ser Cys Val Tyr Ile Pro Cys Thr Ile Thr
1               5                   10                  15

Ala Leu Leu Gly Cys Ser Cys Lys Asn Lys Val Cys Tyr Asn
            20                  25                  30

<210> SEQ ID NO 61
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gly Val Ile Pro Cys Gly Glu Ser Cys Val Phe Ile Pro Cys Ile Ser
1               5                   10                  15

Thr Leu Leu Gly Cys Ser Cys Lys Asn Lys Val Cys Tyr Arg Asn
            20                  25                  30

<210> SEQ ID NO 62
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gly Ile Pro Cys Gly Glu Ser Cys Val Phe Ile Pro Cys Ile Thr Ser
1               5                   10                  15

Val Ala Gly Cys Ser Cys Lys Ser Lys Val Cys Tyr Arg Asn
            20                  25                  30

<210> SEQ ID NO 63
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Lys Ile Pro Cys Gly Glu Ser Cys Val Trp Ile Pro Cys Val Thr Ser
1               5                   10                  15

Ile Phe Asn Cys Lys Cys Glu Asn Lys Val Cys Tyr His Asp
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Lys Ile Pro Cys Gly Glu Ser Cys Val Trp Ile Pro Cys Leu Thr Ser
1               5                   10                  15

Val Phe Asn Cys Lys Cys Glu Asn Lys Val Cys Tyr His Asp
            20                  25                  30
```

```
<210> SEQ ID NO 65
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ile Pro Cys Gly Glu Ser Cys Val Trp Ile Pro Cys Ile Ser Ala
1               5                   10                  15

Ala Ile Gly Cys Ser Cys Lys Asn Lys Val Cys Tyr Arg
            20                  25

<210> SEQ ID NO 66
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gly Ile Pro Cys Gly Glu Ser Cys Val Trp Ile Pro Cys Ile Ser Ser
1               5                   10                  15

Ala Ile Gly Cys Ser Cys Lys Asn Lys Val Cys Tyr Arg Asn
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gly Ile Pro Cys Gly Glu Ser Cys Val Trp Ile Pro Cys Leu Thr Ser
1               5                   10                  15

Ala Ile Gly Cys Ser Cys Lys Ser Lys Val Cys Tyr Arg Asn
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gly Thr Pro Cys Gly Glu Ser Cys Val Trp Ile Pro Cys Ile Ser Ser
1               5                   10                  15

Ala Val Gly Cys Ser Cys Lys Asn Lys Val Cys Tyr Lys Asn
            20                  25                  30

<210> SEQ ID NO 69
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Thr Leu Pro Cys Gly Glu Ser Cys Val Trp Ile Pro Cys Ile Ser
```

```
                1               5                  10                  15
Ala Ala Val Gly Cys Ser Cys Lys Ser Lys Val Cys Tyr Lys Asn
                20                  25                  30
```

<210> SEQ ID NO 70
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Ser Ile Pro Cys Gly Glu Ser Cys Val Trp Ile Pro Cys Thr Ile Thr
1               5                   10                  15
Ala Leu Ala Gly Cys Lys Cys Lys Ser Lys Val Cys Tyr Asn
                20                  25                  30
```

<210> SEQ ID NO 71
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Gly Ile Pro Cys Gly Glu Ser Cys Val Tyr Ile Pro Cys Leu Thr Ser
1               5                   10                  15
Ala Val Gly Cys Ser Cys Lys Ser Lys Val Cys Tyr Arg Asn
                20                  25                  30
```

<210> SEQ ID NO 72
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Gly Thr Pro Cys Gly Glu Ser Cys Val Tyr Ile Pro Cys Ile Ser Gly
1               5                   10                  15
Val Ile Gly Cys Ser Cys Thr Asp Lys Val Cys Tyr Leu Asn
                20                  25                  30
```

<210> SEQ ID NO 73
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Gly Leu Pro Val Cys Gly Glu Thr Cys Phe Gly Gly Thr Cys Asn Thr
1               5                   10                  15
Pro Gly Cys Ser Cys Asp Pro Trp Pro Met Cys Ser Arg Asn
                20                  25                  30
```

<210> SEQ ID NO 74
<211> LENGTH: 29
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 74

Gly Val Pro Ile Cys Gly Glu Thr Cys Val Gly Gly Thr Cys Asn Thr
1               5                   10                  15

Pro Gly Cys Ser Cys Ser Trp Pro Val Cys Thr Arg Asn
            20                  25

<210> SEQ ID NO 75
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Leu Pro Ile Cys Gly Glu Thr Cys Val Gly Gly Ser Cys Asn Thr
1               5                   10                  15

Pro Gly Cys Ser Cys Ser Trp Pro Val Cys Thr Arg Asn
            20                  25

<210> SEQ ID NO 76
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Val Pro Ile Cys Gly Glu Thr Cys Thr Leu Gly Thr Cys Tyr Thr
1               5                   10                  15

Ala Gly Cys Ser Cys Ser Trp Pro Val Cys Thr Arg Asn
            20                  25

<210> SEQ ID NO 77
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gly Val Pro Val Cys Gly Glu Thr Cys Phe Gly Gly Thr Cys Asn Thr
1               5                   10                  15

Pro Gly Cys Ser Cys Asp Pro Trp Pro Val Cys Ser Arg Asn
            20                  25                  30

<210> SEQ ID NO 78
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gly Leu Pro Val Cys Gly Glu Thr Cys Phe Gly Gly Thr Cys Asn Thr
1               5                   10                  15

Pro Gly Cys Ser Cys Glu Thr Trp Pro Val Cys Ser Arg Asn
            20                  25                  30
```

<210> SEQ ID NO 79
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gly Val Ile Pro Cys Gly Glu Ser Cys Val Phe Ile Pro Cys Ile Ser
1               5                   10                  15

Ala Ala Ile Gly Cys Ser Cys Lys Asn Lys Val Cys Tyr Arg Asn
            20                  25                  30

<210> SEQ ID NO 80
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Thr Ala Cys Gly Glu Ser Cys Tyr Val Leu Pro Cys Phe Thr Val
1               5                   10                  15

Gly Cys Thr Cys Thr Ser Ser Gln Cys Phe Lys Asn
            20                  25

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gly Ile Pro Cys Gly Glu Ser Cys Val Phe Ile Pro Cys Leu Thr Thr
1               5                   10                  15

Val Ala Gly Cys Ser Cys Lys Asn Lys Val Cys Tyr Arg Asn
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gly Phe Pro Cys Gly Glu Ser Cys Val Phe Ile Pro Cys Ile Ser Ala
1               5                   10                  15

Ala Ile Gly Cys Ser Cys Lys Asn Lys Val Cys Tyr Arg Asn
            20                  25                  30

<210> SEQ ID NO 83
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)

<223> OTHER INFORMATION: Any unnatural amino acid

<400> SEQUENCE: 83

Gly Leu Pro Val Cys Gly Glu Thr Cys Val Gly Gly Thr Cys Asn Thr
1               5                   10                  15

Pro Gly Cys Ser Cys Ser Arg Pro Val Cys Thr Xaa Asn
            20                  25

<210> SEQ ID NO 84
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ser Ile Ser Cys Gly Glu Ser Cys Ala Met Ile Ser Phe Cys Phe Thr
1               5                   10                  15

Glu Val Ile Gly Cys Ser Cys Lys Asn Lys Val Cys Tyr Leu Asn
            20                  25                  30

<210> SEQ ID NO 85
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Leu Glu Thr Gln Lys Pro Asn His Leu Glu Glu Ala Leu Val Ala
1               5                   10                  15

Phe Ala Lys Lys Gly Asn Leu Gly Gly Leu Pro
            20                  25

<210> SEQ ID NO 86
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gly Ile Pro Cys Gly Glu Ser Cys His Tyr Ile Pro Cys Val Thr Ser
1               5                   10                  15

Ala Ile Gly Cys Ser Cys Arg Asn Arg Ser Cys Met Arg Asn
            20                  25                  30

<210> SEQ ID NO 87
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gly Ile Pro Cys Gly Asp Ser Cys His Tyr Ile Pro Cys Val Thr Ser
1               5                   10                  15

Thr Ile Gly Cys Ser Cys Thr Asn Gly Ser Cys Met Arg Asn
            20                  25                  30

```
<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Val Lys Ser Ser Glu Thr Thr Leu Met Phe Leu Lys Glu Met Gln
1               5                   10                  15

Leu Lys Leu Pro
            20

<210> SEQ ID NO 89
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gly Leu Pro Val Cys Gly Glu Thr Cys Phe Thr Gly Thr Cys Tyr Thr
1               5                   10                  15

Asn Gly Cys Thr Cys Asp Pro Trp Pro Val Cys Thr Arg Asn
            20                  25                  30

<210> SEQ ID NO 90
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gly Leu Pro Val Cys Gly Glu Thr Cys Phe Gly Gly Thr Cys Asn Thr
1               5                   10                  15

Pro Gly Cys Ile Cys Asp Pro Trp Pro Val Cys Thr Arg Asn
            20                  25                  30

<210> SEQ ID NO 91
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Ala Ile Ala Cys Gly Glu Ser Cys Val Tyr Ile Pro Cys Phe Ile
1               5                   10                  15

Pro Gly Cys Ser Cys Arg Asn Arg Val Cys Tyr Leu Asn
            20                  25

<210> SEQ ID NO 92
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Ser Ile Ser Cys Gly Glu Ser Cys Val Tyr Ile Pro Cys Thr Val Thr
```

```
                1               5                   10                  15
Ala Leu Val Gly Cys Thr Cys Lys Asp Lys Val Cys Tyr Leu Asn
                20                  25                  30
```

<210> SEQ ID NO 93
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Gly Ser Pro Ile Gln Cys Ala Glu Thr Cys Phe Ile Gly Lys Cys Tyr
1               5                   10                  15
Thr Glu Glu Leu Gly Cys Thr Cys Thr Ala Phe Leu Cys Met Lys Asn
                20                  25                  30
```

<210> SEQ ID NO 94
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Gly Ser Pro Arg Gln Cys Ala Glu Thr Cys Phe Ile Gly Lys Cys Tyr
1               5                   10                  15
Thr Glu Glu Leu Gly Cys Thr Cys Thr Ala Phe Leu Cys Met Lys Asn
                20                  25                  30
```

<210> SEQ ID NO 95
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

```
Gly Ser Val Pro Cys Gly Glu Ser Cys Val Tyr Ile Pro Cys Phe Thr
1               5                   10                  15
Gly Ile Ala Gly Cys Ser Cys Lys Ser Lys Val Cys Tyr Tyr Asn
                20                  25                  30
```

<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

```
Gly Glu Ile Pro Cys Gly Glu Ser Cys Val Tyr Leu Pro Cys Phe Leu
1               5                   10                  15
Pro Asn Cys Tyr Cys Arg Asn His Val Cys Tyr Leu Asn
                20                  25
```

<210> SEQ ID NO 97
<211> LENGTH: 30
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 97

Ser Ile Ser Cys Gly Glu Thr Cys Thr Thr Phe Asn Cys Trp Ile Pro
1               5                   10                  15

Asn Cys Lys Cys Asn His His Asp Lys Val Cys Tyr Trp Asn
            20                  25                  30

<210> SEQ ID NO 98
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Cys Ala Glu Thr Cys Val Val Leu Pro Cys Phe Ile Val Pro Gly Cys
1               5                   10                  15

Ser Cys Lys Ser Ser Val Cys Tyr Phe Asn
            20                  25

<210> SEQ ID NO 99
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Cys Ala Glu Thr Cys Ile Tyr Ile Pro Cys Phe Thr Glu Ala Val Gly
1               5                   10                  15

Cys Lys Cys Lys Asp Lys Val Cys Tyr Lys Asn
            20                  25

<210> SEQ ID NO 100
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gly Ile Pro Cys Gly Glu Ser Cys Val Phe Ile Pro Cys Ile Ser Gly
1               5                   10                  15

Val Ile Gly Cys Ser Cys Lys Ser Lys Val Cys Tyr Arg Asn
            20                  25                  30

<210> SEQ ID NO 101
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ile Ala Cys Gly Glu Ser Cys Ala Tyr Phe Gly Cys Trp Ile Pro
1               5                   10                  15

Gly Cys Ser Cys Arg Asn Lys Val Cys Tyr Phe Asn
            20                  25

<210> SEQ ID NO 102
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gly Thr Pro Cys Gly Glu Ser Cys Val Tyr Ile Pro Cys Phe Thr Ala
1               5                   10                  15

Val Val Gly Cys Thr Cys Lys Asp Lys Val Cys Tyr Leu Asn
            20                  25                  30

<210> SEQ ID NO 103
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Thr Pro Cys Ala Glu Ser Cys Val Tyr Leu Pro Cys Phe Thr Gly
1               5                   10                  15

Val Ile Gly Cys Thr Cys Lys Asp Lys Val Cys Tyr Leu Asn
            20                  25                  30

<210> SEQ ID NO 104
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Asn Ile Pro Cys Gly Glu Ser Cys Ile Phe Phe Pro Cys Phe Asn
1               5                   10                  15

Pro Gly Cys Ser Cys Lys Asp Asn Leu Cys Tyr Tyr Asn
            20                  25

<210> SEQ ID NO 105
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Cys Gly Glu Thr Cys Val Ile Leu Pro Cys Ile Ser Ala Ala Leu Gly
1               5                   10                  15

Cys Ser Cys Lys Asp Thr Val Cys Tyr Lys Asn
            20                  25

<210> SEQ ID NO 106
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

```
Cys Gly Glu Thr Cys Val Ile Phe Pro Cys Ile Ser Ala Ala Phe Gly
1               5                   10                  15

Cys Ser Cys Lys Asp Thr Val Cys Tyr Lys Asn
            20                  25

<210> SEQ ID NO 107
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gly Ser Val Pro Cys Gly Glu Ser Cys Val Trp Ile Pro Cys Ile Ser
1               5                   10                  15

Gly Ile Ala Gly Cys Ser Cys Lys Asn Lys Val Cys Tyr Leu Asn
            20                  25                  30

<210> SEQ ID NO 108
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Cys Gly Glu Thr Cys Leu Phe Ile Pro Cys Ile Phe Ser Val Val Gly
1               5                   10                  15

Cys Ser Cys Ser Ser Lys Val Cys Tyr Arg Asn
            20                  25

<210> SEQ ID NO 109
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Cys Gly Glu Thr Cys Val Thr Gly Thr Cys Tyr Thr Pro Gly Cys Ala
1               5                   10                  15

Cys Asp Trp Pro Val Cys Lys Arg Asp
            20                  25

<210> SEQ ID NO 110
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Cys Gly Glu Thr Cys Ile Trp Gly Arg Cys Tyr Ser Glu Asn Ile Gly
1               5                   10                  15

Cys His Cys Gly Phe Gly Ile Cys Thr Leu Asn
            20                  25

<210> SEQ ID NO 111
<211> LENGTH: 27
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 111

Cys Gly Glu Thr Cys Leu Phe Ile Pro Cys Leu Thr Ser Val Phe Gly
1               5                   10                  15

Cys Ser Cys Lys Asn Arg Gly Cys Tyr Lys Ile
            20                  25

<210> SEQ ID NO 112
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Cys Gly Glu Thr Cys Val Val Asp Thr Arg Cys Tyr Thr Lys Lys Cys
1               5                   10                  15

Ser Cys Ala Trp Pro Val Cys Met Arg Asn
            20                  25

<210> SEQ ID NO 113
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Val Trp Ile Pro Cys Ile Ser Ala Ala Ile Gly Cys Ser Cys Lys
1               5                   10                  15

Ser Lys Val Cys Tyr Arg Asn
            20

<210> SEQ ID NO 114
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Cys Gly Glu Ser Cys Val Tyr Ile Pro Cys Thr Val Thr Ala Leu Leu
1               5                   10                  15

Gly Cys Ser Cys Lys Asp Lys Val Cys Tyr Lys Asn
            20                  25

<210> SEQ ID NO 115
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Gly Glu Thr Cys Lys Val Thr Lys Arg Cys Ser Gly Gln Gly Cys
1               5                   10                  15

Ser Cys Leu Lys Gly Arg Ser Cys Tyr Asp
            20                  25
```

<210> SEQ ID NO 116
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Cys Gly Glu Thr Cys Val Val Leu Pro Cys Phe Ile Val Pro Gly Cys
1               5                   10                  15

Ser Cys Lys Ser Ser Val Cys Tyr Phe Asn
            20                  25

<210> SEQ ID NO 117
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Cys Gly Glu Thr Cys Ile Tyr Ile Pro Cys Phe Thr Glu Ala Val Gly
1               5                   10                  15

Cys Lys Cys Lys Asp Lys Val Cys Tyr Lys Asn
            20                  25

<210> SEQ ID NO 118
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gly Gly Thr Ile Phe Asp Cys Gly Glu Ser Cys Phe Leu Gly Thr Cys
1               5                   10                  15

Tyr Thr Lys Gly Cys Ser Cys Gly Glu Trp Lys Leu Cys Tyr Gly Glu
            20                  25                  30

Asn

<210> SEQ ID NO 119
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gly Ser Val Leu Asn Cys Gly Glu Thr Cys Leu Leu Gly Thr Cys Tyr
1               5                   10                  15

Thr Thr Gly Cys Thr Cys Asn Lys Tyr Arg Val Cys Thr Lys Asp
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 120

Gly Ile Pro Cys Ala Glu Ser Cys Val Trp Ile Pro Cys Thr Val Thr
1               5                   10                  15

Ala Leu Leu Gly Cys Ser Cys Ser Asn Asn Val Cys Tyr Asn
            20                  25                  30

<210> SEQ ID NO 121
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gly Ile Pro Cys Gly Glu Ser Cys Val Trp Ile Pro Cys Ile Ser Ala
1               5                   10                  15

Ala Ile Gly Cys Ser Cys Lys Ser Lys Val Cys Tyr Arg Asn
            20                  25                  30

<210> SEQ ID NO 122
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Ala Ile Ser Cys Gly Glu Thr Cys Phe Lys Phe Lys Cys Tyr Thr
1               5                   10                  15

Pro Arg Cys Ser Cys Ser Tyr Pro Val Cys Lys
            20                  25

<210> SEQ ID NO 123
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gly Ser Ile Pro Ala Cys Gly Glu Ser Cys Phe Lys Gly Lys Cys Tyr
1               5                   10                  15

Thr Pro Gly Cys Ser Cys Ser Lys Tyr Pro Leu Cys Ala Lys Asn
            20                  25                  30

<210> SEQ ID NO 124
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Leu Val Pro Cys Gly Glu Thr Cys Phe Thr Gly Lys Cys Tyr Thr
1               5                   10                  15

Pro Gly Cys Ser Cys Ser Tyr Pro Ile Cys Lys Lys Asn
            20                  25

<210> SEQ ID NO 125
```

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Leu Pro Cys Gly Glu Thr Cys Phe Thr Gly Lys Cys Tyr Thr Pro
1               5                   10                  15

Gly Cys Ser Cys Ser Tyr Pro Ile Cys Lys Lys Ile Asn
            20                  25

<210> SEQ ID NO 126
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gly Ile Pro Cys Gly Glu Ser Cys Val Trp Ile Pro Cys Ile Ser Ala
1               5                   10                  15

Ala Ile Gly Cys Ser Cys Lys Asn Lys Val Cys Tyr Arg Asn
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gly Ile Pro Cys Gly Glu Ser Cys Val Tyr Ile Pro Cys Thr Val Thr
1               5                   10                  15

Ala Leu Ala Gly Cys Lys Cys Lys Ser Lys Val Cys Tyr Asn
            20                  25                  30

<210> SEQ ID NO 128
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gly Thr Leu Pro Cys Gly Glu Ser Cys Val Trp Ile Pro Cys Ile Ser
1               5                   10                  15

Ser Val Val Gly Cys Ser Cys Lys Ser Lys Val Cys Tyr Lys Asp
            20                  25                  30

<210> SEQ ID NO 129
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gly Ile Pro Cys Gly Glu Ser Cys Val Trp Ile Pro Cys Leu Thr Ser
1               5                   10                  15
```

Ala Ile Gly Cys Ser Cys Lys Ser Lys Val Cys Tyr Arg Asp
            20                  25                  30

<210> SEQ ID NO 130
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Leu Pro Val Cys Gly Glu Thr Cys Val Thr Gly Ser Cys Tyr Thr
1               5                   10                  15

Pro Gly Cys Thr Cys Ser Trp Pro Val Cys Thr Arg Asn
            20                  25

<210> SEQ ID NO 131
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Leu Pro Ile Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 132
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gly Leu Pro Thr Cys Gly Glu Thr Cys Phe Gly Gly Thr Cys Asn Thr
1               5                   10                  15

Pro Gly Cys Thr Cys Asp Ser Ser Trp Pro Ile Cys Thr His Asn
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gly Leu Pro Thr Cys Gly Glu Thr Cys Phe Gly Gly Thr Cys Asn Thr
1               5                   10                  15

Pro Gly Cys Thr Cys Asp Pro Trp Pro Val Cys Thr His Asn
            20                  25                  30

<210> SEQ ID NO 134
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

Asp Ile Phe Cys Gly Glu Thr Cys Ala Phe Ile Pro Cys Ile Thr His
1               5                   10                  15
Val Pro Gly Thr Cys Ser Cys Lys Ser Lys Val Cys Tyr Phe Asn
            20                  25                  30

<210> SEQ ID NO 135
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Leu Pro Val Cys Gly Glu Thr Cys Val Gly Gly Thr Cys Asn Thr
1               5                   10                  15
Pro Gly Cys Thr Cys Ser Trp Asp Lys Cys Thr Arg Asn
            20                  25

<210> SEQ ID NO 136
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Leu Pro Val Cys Gly Glu Thr Cys Val Gly Gly Thr Cys Asn Thr
1               5                   10                  15
Pro Gly Cys Thr Cys Ser Lys Asn Lys Cys Thr Arg Asn
            20                  25

<210> SEQ ID NO 137
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Any unnatural amino acid

<400> SEQUENCE: 137

Gly Ile Pro Cys Gly Xaa Ser Cys Val Trp Ile Pro Cys Ile Ser Ser
1               5                   10                  15
Ala Ile Gly Cys Ser Cys Lys Ser Lys Val Cys Tyr Arg Asn
            20                  25                  30

<210> SEQ ID NO 138
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Any unnatural amino acid
<220> FEATURE:
<221> NAME/KEY: MOD_RES

```
<222> LOCATION: (25)..(25)
<223> OTHER INFORMATION: Any unnatural amino acid

<400> SEQUENCE: 138

Gly Ile Pro Cys Gly Glu Ser Cys Val Trp Ile Pro Cys Ile Ser Ser
1               5                   10                  15

Ala Ile Gly Cys Ser Cys Xaa Ser Xaa Val Cys Tyr Arg Asn
            20                  25                  30

<210> SEQ ID NO 139
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Any unnatural amino acid

<400> SEQUENCE: 139

Gly Ile Pro Cys Gly Glu Ser Cys Val Trp Ile Pro Cys Ile Ser Ser
1               5                   10                  15

Ala Ile Gly Cys Ser Cys Lys Ser Lys Val Cys Tyr Xaa Asn
            20                  25                  30

<210> SEQ ID NO 140
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Any unnatural amino acid
<220> FEATURE:
<221> NAME/KEY: MOD_RES
<222> LOCATION: (25)..(25)
<223> OTHER INFORMATION: Any unnatural amino acid
<220> FEATURE:
<221> NAME/KEY: MOD_RES
<222> LOCATION: (29)..(29)
<223> OTHER INFORMATION: Any unnatural amino acid

<400> SEQUENCE: 140

Gly Ile Pro Cys Gly Glu Ser Cys Val Trp Ile Pro Cys Ile Ser Ser
1               5                   10                  15

Ala Ile Gly Cys Ser Cys Xaa Ser Xaa Val Cys Tyr Xaa Asn
            20                  25                  30

<210> SEQ ID NO 141
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25
```

```
<210> SEQ ID NO 142
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 143
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Leu Pro Val Cys Gly Glu Thr Cys Phe Gly Gly Thr Cys Asn Thr
1               5                   10                  15

Pro Gly Cys Ser Cys Thr Trp Pro Ile Cys Thr Arg Asp
            20                  25

<210> SEQ ID NO 144
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Leu Pro Val Cys Gly Glu Thr Cys Phe Gly Gly Thr Cys Asn Thr
1               5                   10                  15

Pro Gly Cys Ser Cys Thr Trp Pro Ile Cys Thr Arg Asp
            20                  25

<210> SEQ ID NO 145
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gly Ser Val Phe Asn Cys Gly Glu Thr Cys Val Leu Gly Thr Cys Tyr
1               5                   10                  15

Thr Pro Gly Cys Thr Cys Asn Thr Tyr Arg Val Cys Thr Lys Asp
            20                  25                  30

<210> SEQ ID NO 146
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gly Leu Pro Thr Cys Gly Glu Thr Cys Phe Gly Gly Thr Cys Asn Thr
```

```
                1               5                  10                  15
Pro Gly Cys Ser Cys Ser Ser Trp Pro Ile Cys Thr Arg Asp
            20                  25                  30
```

<210> SEQ ID NO 147
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

```
Gly Leu Pro Thr Cys Gly Glu Thr Cys Phe Gly Gly Thr Cys Asn Thr
1               5                   10                  15
Pro Gly Cys Ser Cys Ser Ser Trp Pro Ile Cys Thr Arg Asp
            20                  25                  30
```

<210> SEQ ID NO 148
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

```
Gly Leu Pro Val Cys Gly Glu Thr Cys Phe Gly Gly Thr Cys Asn Thr
1               5                   10                  15
Pro Gly Cys Ser Cys Thr Asp Pro Ile Cys Thr Arg Asp
            20                  25
```

<210> SEQ ID NO 149
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

```
Gly Ser Leu Cys Gly Asp Thr Cys Phe Val Leu Gly Cys Asn Asp Ser
1               5                   10                  15
Ser Cys Ser Cys Asn Tyr Pro Ile Cys Val Lys Asp
            20                  25
```

<210> SEQ ID NO 150
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

```
Gly Leu Pro Val Cys Gly Glu Thr Cys Phe Gly Gly Thr Cys Asn Thr
1               5                   10                  15
Pro Gly Cys Ala Cys Asp Pro Trp Pro Val Cys Thr Arg Asp
            20                  25                  30
```

<210> SEQ ID NO 151
<211> LENGTH: 30
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 151

Gly Leu Pro Val Cys Gly Glu Ser Cys Phe Gly Gly Thr Cys Asn Thr
1               5                   10                  15

Pro Gly Cys Ala Cys Asp Pro Trp Pro Val Cys Thr Arg Asp
            20                  25                  30

<210> SEQ ID NO 152
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Leu Pro Val Cys Gly Glu Ser Cys Phe Gly Gly Ser Cys Tyr Thr
1               5                   10                  15

Pro Gly Cys Ser Cys Thr Trp Pro Ile Cys Thr Arg Asp
            20                  25

<210> SEQ ID NO 153
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gly Ile Pro Cys Ala Glu Ser Cys Val Tyr Ile Pro Cys Thr Ile Thr
1               5                   10                  15

Ala Leu Leu Gly Cys Lys Cys Gln Asp Lys Val Cys Tyr Asp
            20                  25                  30

<210> SEQ ID NO 154
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gly Ile Pro Cys Ala Glu Ser Cys Val Tyr Ile Pro Cys Thr Ile Thr
1               5                   10                  15

Ala Leu Leu Gly Cys Lys Cys Lys Asp Gln Val Cys Tyr Asn
            20                  25                  30

<210> SEQ ID NO 155
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Cys Gly Glu Thr Cys Val Gly Gly Thr Cys Asn Thr Pro Gly Cys Thr
1               5                   10                  15

Cys Ser Trp Pro Val Cys Arg Arg Lys Arg Arg Arg
            20                  25
```

<210> SEQ ID NO 156
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Cys Gly Glu Thr Cys Arg Arg Lys Arg Arg Cys Asn Thr Pro Gly
1               5                   10                  15

Cys Thr Cys Ser Trp Pro Val Cys Thr Arg Asn Gly Leu Pro Val
            20                  25                  30

<210> SEQ ID NO 157
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Cys Gly Glu Thr Cys Val Gly Gly Thr Cys Asn Thr Arg Arg Lys Arg
1               5                   10                  15

Arg Arg Gly Cys Thr Cys Ser Trp Pro Val Cys Thr Arg Asn Gly Leu
            20                  25                  30

Pro Val

<210> SEQ ID NO 158
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Cys Gly Glu Thr Cys Val Gly Gly Thr Cys Asn Thr Pro Gly Cys Thr
1               5                   10                  15

Cys Arg Arg Lys Arg Arg Arg Val Cys Thr Arg Asn Gly Leu Pro Val
            20                  25                  30

<210> SEQ ID NO 159
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Cys Gly Glu Thr Cys Val Gly Gly Thr Cys Asn Thr Pro Gly Cys Thr
1               5                   10                  15

Cys Arg Arg Lys Arg Arg Arg Cys Thr Arg Asn Gly Leu Pro Val
            20                  25                  30

<210> SEQ ID NO 160
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 160

Cys Gly Glu Thr Cys Val Gly Gly Thr Cys Arg Arg Lys Arg Arg Arg
1               5                   10                  15

Cys Thr Cys Ser Trp Pro Val Cys Thr Arg Asn Gly Leu Pro Val
                20                  25                  30

<210> SEQ ID NO 161
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gly Val Pro Cys Ala Glu Ser Cys Val Tyr Ile Pro Cys Ile Ser Thr
1               5                   10                  15

Val Leu Gly Cys Ser Cys Ser Asn Gln Val Cys Tyr Arg Asn
                20                  25                  30

<210> SEQ ID NO 162
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gly Phe Ile Pro Cys Gly Glu Thr Cys Ile Trp Asp Lys Thr Cys His
1               5                   10                  15

Ala Ala Gly Cys Ser Cys Ser Val Ala Asn Ile Cys Val Arg Asn
                20                  25                  30

<210> SEQ ID NO 163
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gly Ala Asp Gly Phe Cys Gly Glu Ser Cys Tyr Val Ile Pro Cys Ile
1               5                   10                  15

Ser Tyr Leu Val Gly Cys Ser Cys Asp Thr Ile Glu Lys Val Cys Lys
                20                  25                  30

Arg Asn

<210> SEQ ID NO 164
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Gly Gly Thr Ile Phe Asp Cys Gly Glu Thr Cys Phe Leu Gly Thr Cys
1               5                   10                  15

Tyr Thr Pro Gly Cys Ser Cys Gly Asn Tyr Gly Phe Cys Tyr Gly Thr
                20                  25                  30

Asn
```

<210> SEQ ID NO 165
<211> LENGTH: 33
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 165

Gly Gly Thr Ile Phe Asp Cys Gly Glu Ser Cys Phe Leu Gly Thr Cys
1               5                   10                  15

Tyr Thr Ala Gly Cys Ser Cys Gly Asn Trp Gly Leu Cys Tyr Gly Thr
            20                  25                  30

Asn

<210> SEQ ID NO 166
<211> LENGTH: 33
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 166

Gly Gly Thr Ile Phe Asp Cys Gly Glu Thr Cys Phe Leu Gly Thr Cys
1               5                   10                  15

Tyr Thr Ala Gly Cys Ser Cys Gly Asn Trp Gly Leu Cys Tyr Gly Thr
            20                  25                  30

Asn

<210> SEQ ID NO 167
<211> LENGTH: 30
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 167

Gly Val Pro Cys Gly Glu Ser Cys Val Phe Ile Pro Cys Ile Thr Gly
1               5                   10                  15

Val Ile Gly Cys Ser Cys Ser Ser Asn Val Cys Tyr Leu Asn
            20                  25                  30

<210> SEQ ID NO 168
<211> LENGTH: 30
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 168

Gly Ile Pro Cys Ala Glu Ser Cys Val Trp Ile Pro Cys Thr Val Thr
1               5                   10                  15

Ala Leu Val Gly Cys Ser Cys Ser Asp Lys Val Cys Tyr Asn
            20                  25                  30

<210> SEQ ID NO 169
<211> LENGTH: 29
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 169

Gly Leu Pro Val Cys Gly Glu Thr Cys Phe Gly Gly Thr Cys Asn Thr
1               5                   10                  15

Pro Gly Cys Ser Cys Ser Tyr Pro Ile Cys Thr Arg Asn
            20                  25

<210> SEQ ID NO 170
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Leu Pro Val Cys Gly Glu Thr Cys Phe Gly Gly Thr Cys Asn Thr
1               5                   10                  15

Pro Gly Cys Thr Cys Ser Tyr Pro Ile Cys Thr Arg Asn
            20                  25

<210> SEQ ID NO 171
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Leu Pro Val Cys Gly Glu Thr Cys Ala Phe Gly Ser Cys Tyr Thr
1               5                   10                  15

Pro Gly Cys Ser Cys Ser Trp Pro Val Cys Thr Arg Asn
            20                  25

<210> SEQ ID NO 172
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Leu Pro Val Cys Gly Glu Thr Cys Phe Gly Gly Arg Cys Asn Thr
1               5                   10                  15

Pro Gly Cys Thr Cys Ser Tyr Pro Ile Cys Thr Arg Asn
            20                  25

<210> SEQ ID NO 173
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gly Ile Pro Cys Ala Glu Ser Cys Val Trp Ile Pro Cys Thr Val Thr
1               5                   10                  15

Ala Leu Ile Gly Cys Gly Cys Ser Asn Lys Val Cys Tyr Asn
            20                  25                  30
```

<210> SEQ ID NO 174
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gly Thr Ile Pro Cys Gly Glu Ser Cys Val Phe Ile Pro Cys Leu Thr
1               5                   10                  15

Ser Ala Leu Gly Cys Ser Cys Lys Ser Lys Val Cys Tyr Lys Asn
            20                  25                  30

<210> SEQ ID NO 175
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gly Thr Phe Pro Cys Gly Glu Ser Cys Val Phe Ile Pro Cys Leu Thr
1               5                   10                  15

Ser Ala Ile Gly Cys Ser Cys Lys Ser Lys Val Cys Tyr Lys Asn
            20                  25                  30

<210> SEQ ID NO 176
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gly Leu Leu Pro Cys Ala Glu Ser Cys Val Tyr Ile Pro Cys Leu Thr
1               5                   10                  15

Thr Val Ile Gly Cys Ser Cys Lys Ser Lys Val Cys Tyr Lys Asn
            20                  25                  30

<210> SEQ ID NO 177
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gly Ile Pro Cys Gly Glu Ser Cys Val Trp Ile Pro Cys Leu Thr Ser
1               5                   10                  15

Thr Val Gly Cys Ser Cys Lys Ser Lys Val Cys Tyr Arg Asn
            20                  25                  30

<210> SEQ ID NO 178
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

```
Gly Thr Phe Pro Cys Gly Glu Ser Cys Val Trp Ile Pro Cys Ile Ser
1               5                   10                  15

Lys Val Ile Gly Cys Ala Cys Ser Lys Val Cys Tyr Lys Asn
            20                  25                  30

<210> SEQ ID NO 179
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gly Ile Pro Cys Gly Glu Ser Cys Val Trp Ile Pro Cys Leu Thr Ser
1               5                   10                  15

Ala Val Gly Cys Pro Cys Lys Ser Lys Val Cys Tyr Arg Asn
            20                  25                  30

<210> SEQ ID NO 180
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gly Ile Pro Cys Gly Glu Ser Cys Val Tyr Leu Pro Cys Phe Thr Ala
1               5                   10                  15

Pro Leu Gly Cys Ser Cys Ser Ser Lys Val Cys Tyr Arg Asn
            20                  25                  30

<210> SEQ ID NO 181
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gly Ile Pro Cys Gly Glu Ser Cys Val Trp Ile Pro Cys Leu Thr Ala
1               5                   10                  15

Thr Ile Gly Cys Ser Cys Lys Ser Lys Val Cys Tyr Arg Asn
            20                  25                  30

<210> SEQ ID NO 182
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Ile Pro Cys Ala Glu Ser Cys Val Tyr Leu Pro Cys Val Thr Ile
1               5                   10                  15

Val Ile Gly Cys Ser Cys Lys Asp Lys Val Cys Tyr Asn
            20                  25

<210> SEQ ID NO 183
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 183

Gly Ile Pro Cys Ala Glu Ser Cys Val Trp Ile Pro Cys Thr Val Thr
1               5                   10                  15

Ala Leu Leu Gly Cys Ser Cys Lys Asp Lys Val Cys Tyr Asn
            20                  25                  30

<210> SEQ ID NO 184
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gly Arg Leu Cys Gly Glu Arg Cys Val Ile Glu Arg Thr Arg Ala Trp
1               5                   10                  15

Cys Arg Thr Val Gly Cys Ile Cys Ser Leu His Thr Leu Glu Cys Val
            20                  25                  30

Arg Asn

<210> SEQ ID NO 185
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Leu Pro Val Cys Gly Glu Thr Cys Val Gly Gly Thr Cys Asn Thr
1               5                   10                  15

Pro Gly Cys Gly Cys Ser Trp Pro Val Cys Thr Arg Asn
            20                  25

<210> SEQ ID NO 186
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Leu Pro Val Cys Gly Glu Thr Cys Val Gly Gly Thr Cys Asn Thr
1               5                   10                  15

Pro Gly Cys Ala Cys Ser Trp Pro Val Cys Thr Arg Asn
            20                  25

<210> SEQ ID NO 187
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Gly Ser Ile Pro Cys Gly Glu Ser Cys Val Tyr Ile Pro Cys Ile Ser
1               5                   10                  15
```

Ser Leu Leu Gly Cys Ser Cys Lys Ser Lys Val Cys Tyr Lys Asn
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Gly Ile Pro Cys Ala Glu Ser Cys Val Tyr Ile Pro Cys Leu Thr Ser
1               5                   10                  15

Ala Ile Gly Cys Ser Cys Lys Ser Lys Val Cys Tyr Arg Asn
            20                  25                  30

<210> SEQ ID NO 189
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Ile Pro Cys Gly Glu Ser Cys Val Tyr Leu Pro Cys Phe Thr Thr
1               5                   10                  15

Ile Ile Gly Cys Lys Cys Gln Gly Lys Val Cys Tyr His
            20                  25

<210> SEQ ID NO 190
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gly Ser Ile Pro Cys Gly Glu Ser Cys Val Phe Ile Pro Cys Ile Ser
1               5                   10                  15

Ser Val Val Gly Cys Ser Cys Lys Asn Lys Val Cys Tyr Lys Asn
            20                  25                  30

<210> SEQ ID NO 191
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gly Thr Ile Pro Cys Gly Glu Ser Cys Val Phe Ile Pro Cys Leu Thr
1               5                   10                  15

Ser Ala Ile Gly Cys Ser Cys Lys Ser Lys Val Cys Tyr Lys Asn
            20                  25                  30

<210> SEQ ID NO 192
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Gly Ser Ile Pro Cys Gly Glu Ser Cys Val Tyr Ile Pro Cys Ile Ser
1               5                   10                  15

Ser Leu Leu Gly Cys Ser Cys Glu Ser Lys Val Cys Tyr Lys Asn
            20                  25                  30

<210> SEQ ID NO 193
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gly Ser Ile Pro Cys Gly Glu Ser Cys Val Phe Ile Pro Cys Ile Ser
1               5                   10                  15

Ser Ile Val Gly Cys Ser Cys Lys Ser Lys Val Cys Tyr Lys Asn
            20                  25                  30

<210> SEQ ID NO 194
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gly Ile Pro Cys Gly Glu Ser Cys Val Phe Ile Pro Cys Leu Thr Ser
1               5                   10                  15

Ala Ile Gly Cys Ser Cys Lys Ser Lys Val Cys Tyr Arg Asn
            20                  25                  30

<210> SEQ ID NO 195
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Gly Val Pro Cys Gly Glu Ser Cys Val Trp Ile Pro Cys Leu Thr Ser
1               5                   10                  15

Ile Val Gly Cys Ser Cys Lys Asn Asn Val Cys Thr Leu Asn
            20                  25                  30

<210> SEQ ID NO 196
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gly Val Ile Pro Cys Gly Glu Ser Cys Val Phe Ile Pro Cys Ile Ser
1               5                   10                  15

Ser Val Leu Gly Cys Ser Cys Lys Asn Lys Val Cys Tyr Arg Asn
            20                  25                  30

<210> SEQ ID NO 197

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gly His Pro Thr Cys Gly Glu Thr Cys Leu Gly Thr Cys Tyr Thr
1               5                   10                  15

Pro Gly Cys Thr Cys Lys Arg Pro Val Cys Tyr Lys Asn
            20                  25

<210> SEQ ID NO 198
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gly Ser Ala Ile Leu Cys Gly Glu Ser Cys Thr Leu Gly Glu Cys Tyr
1               5                   10                  15

Thr Pro Gly Cys Thr Cys Ser Trp Pro Ile Cys Thr Lys Asn
            20                  25                  30

<210> SEQ ID NO 199
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly His Pro Ile Cys Gly Glu Thr Cys Val Gly Asn Lys Cys Tyr Thr
1               5                   10                  15

Pro Gly Cys Thr Cys Thr Trp Pro Val Cys Tyr Arg Asn
            20                  25

<210> SEQ ID NO 200
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Gly Ser Ile Pro Cys Gly Glu Gly Cys Val Phe Ile Pro Cys Ile Ser
1               5                   10                  15

Ser Ile Val Gly Cys Ser Cys Lys Ser Lys Val Cys Tyr Lys Asn
            20                  25                  30

<210> SEQ ID NO 201
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Gly Ile Pro Cys Gly Glu Gly Cys Val Tyr Leu Pro Cys Phe Thr Ala
1               5                   10                  15
```

Pro Leu Gly Cys Ser Cys Ser Ser Lys Val Cys Tyr Arg Asn
            20                  25                  30

<210> SEQ ID NO 202
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gly Ile Pro Cys Gly Glu Ser Cys Val Trp Ile Pro Cys Leu Thr Ala
1               5                   10                  15

Ala Ile Gly Cys Ser Cys Ser Ser Lys Val Cys Tyr Arg Asn
            20                  25                  30

<210> SEQ ID NO 203
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gly Val Pro Cys Gly Glu Ser Cys Val Trp Ile Pro Cys Leu Thr Ser
1               5                   10                  15

Ala Ile Gly Cys Ser Cys Lys Ser Val Cys Tyr Arg Asn
            20                  25                  30

<210> SEQ ID NO 204
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gly Ile Pro Cys Gly Glu Ser Cys Val Leu Ile Pro Cys Ile Ser Ser
1               5                   10                  15

Val Ile Gly Cys Ser Cys Lys Ser Lys Val Cys Tyr Arg Asn
            20                  25                  30

<210> SEQ ID NO 205
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Gly Val Ile Pro Cys Gly Glu Ser Cys Val Phe Ile Pro Cys Ile Ser
1               5                   10                  15

Ser Val Ile Gly Cys Ser Cys Lys Ser Lys Val Cys Tyr Arg Asn
            20                  25                  30

<210> SEQ ID NO 206
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 206

Gly Ala Gly Cys Ile Glu Thr Cys Tyr Thr Phe Pro Cys Ile Ser Glu
1               5                   10                  15

Met Ile Asn Cys Ser Cys Lys Asn Ser Arg Cys Gln Lys Asn
            20                  25                  30

<210> SEQ ID NO 207
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Gly Ile Pro Cys Gly Glu Ser Cys Val Trp Ile Pro Cys Ile Ser Ser
1               5                   10                  15

Ala Ile Gly Cys Ser Cys Lys Asn Lys Val Cys Tyr Arg Lys
            20                  25                  30

<210> SEQ ID NO 208
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Gly Ile Pro Cys Gly Glu Ser Cys Val Trp Ile Pro Cys Ile Ser Gly
1               5                   10                  15

Ala Ile Gly Cys Ser Cys Lys Ser Lys Val Cys Tyr Arg Asn
            20                  25                  30

<210> SEQ ID NO 209
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Thr Ile Pro Cys Ala Glu Ser Cys Val Trp Ile Pro Cys Thr Val Thr
1               5                   10                  15

Ala Leu Leu Gly Cys Ser Cys Lys Asp Lys Val Cys Tyr Asn
            20                  25                  30

<210> SEQ ID NO 210
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Leu Pro Ile Cys Gly Glu Thr Cys Thr Leu Gly Thr Cys Tyr Thr
1               5                   10                  15

Val Gly Cys Thr Cys Ser Trp Pro Ile Cys Thr Arg Asn
            20                  25

```
<210> SEQ ID NO 211
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ala Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 212
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Ala Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 213
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Leu Ala Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 214
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Leu Pro Ala Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 215
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gly Leu Pro Val Cys Ala Glu Thr Cys Val Gly Gly Thr Cys Asn Thr
```

```
                1               5                  10                  15
Pro Gly Cys Thr Cys Ser Trp Pro Val Cys Thr Arg Asn
            20                  25
```

<210> SEQ ID NO 216
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

```
Gly Leu Pro Val Cys Gly Ala Thr Cys Val Gly Gly Thr Cys Asn Thr
1               5                  10                  15
Pro Gly Cys Thr Cys Ser Trp Pro Val Cys Thr Arg Asn
            20                  25
```

<210> SEQ ID NO 217
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Gly Leu Pro Val Cys Gly Glu Ala Cys Val Gly Gly Thr Cys Asn Thr
1               5                  10                  15
Pro Gly Cys Thr Cys Ser Trp Pro Val Cys Thr Arg Asn
            20                  25
```

<210> SEQ ID NO 218
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Gly Leu Pro Val Cys Gly Glu Thr Cys Ala Gly Gly Thr Cys Asn Thr
1               5                  10                  15
Pro Gly Cys Thr Cys Ser Trp Pro Val Cys Thr Arg Asn
            20                  25
```

<210> SEQ ID NO 219
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

```
Gly Leu Pro Val Cys Gly Glu Thr Cys Val Ala Gly Thr Cys Asn Thr
1               5                  10                  15
Pro Gly Cys Thr Cys Ser Trp Pro Val Cys Thr Arg Asn
            20                  25
```

<210> SEQ ID NO 220
<211> LENGTH: 29
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 220

Gly Leu Pro Val Cys Gly Glu Thr Cys Val Gly Ala Thr Cys Asn Thr
1               5                   10                  15

Pro Gly Cys Thr Cys Ser Trp Pro Val Cys Thr Arg Asn
            20                  25

<210> SEQ ID NO 221
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Leu Pro Val Cys Gly Glu Thr Cys Val Gly Gly Ala Cys Asn Thr
1               5                   10                  15

Pro Gly Cys Thr Cys Ser Trp Pro Val Cys Thr Arg Asn
            20                  25

<210> SEQ ID NO 222
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Leu Pro Val Cys Gly Glu Thr Cys Val Gly Gly Thr Cys Ala Thr
1               5                   10                  15

Pro Gly Cys Thr Cys Ser Trp Pro Val Cys Thr Arg Asn
            20                  25

<210> SEQ ID NO 223
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Leu Pro Val Cys Gly Glu Thr Cys Val Gly Gly Thr Cys Asn Ala
1               5                   10                  15

Pro Gly Cys Thr Cys Ser Trp Pro Val Cys Thr Arg Asn
            20                  25

<210> SEQ ID NO 224
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Leu Pro Val Cys Gly Glu Thr Cys Val Gly Gly Thr Cys Asn Thr
1               5                   10                  15

Ala Gly Cys Thr Cys Ser Trp Pro Val Cys Thr Arg Asn
            20                  25
```

<210> SEQ ID NO 225
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Leu Pro Val Cys Gly Glu Thr Cys Val Gly Gly Thr Cys Asn Thr
1               5                   10                  15

Pro Ala Cys Thr Cys Ser Trp Pro Val Cys Thr Arg Asn
            20                  25

<210> SEQ ID NO 226
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Leu Pro Val Cys Gly Glu Thr Cys Val Gly Gly Thr Cys Asn Thr
1               5                   10                  15

Pro Gly Cys Ala Cys Ser Trp Pro Val Cys Thr Arg Asn
            20                  25

<210> SEQ ID NO 227
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Leu Pro Val Cys Gly Glu Thr Cys Val Gly Gly Thr Cys Asn Thr
1               5                   10                  15

Pro Gly Cys Thr Cys Ala Trp Pro Val Cys Thr Arg Asn
            20                  25

<210> SEQ ID NO 228
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Leu Pro Val Cys Gly Glu Thr Cys Val Gly Gly Thr Cys Asn Thr
1               5                   10                  15

Pro Gly Cys Thr Cys Ser Ala Pro Val Cys Thr Arg Asn
            20                  25

<210> SEQ ID NO 229
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Leu Pro Val Cys Gly Glu Thr Cys Val Gly Gly Thr Cys Asn Thr
1               5                   10                  15

Pro Gly Cys Thr Cys Ser Trp Ala Val Cys Thr Arg Asn
            20                  25

<210> SEQ ID NO 230
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gly Leu Pro Val Cys Gly Glu Thr Cys Val Gly Gly Thr Cys Asn Thr
1               5                   10                  15

Pro Gly Cys Thr Cys Ser Trp Pro Ala Cys Thr Arg Asn
            20                  25

<210> SEQ ID NO 231
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gly Leu Pro Val Cys Gly Glu Thr Cys Val Gly Gly Thr Cys Asn Thr
1               5                   10                  15

Pro Gly Cys Thr Cys Ser Trp Pro Val Cys Ala Arg Asn
            20                  25

<210> SEQ ID NO 232
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Ala Asn
            20                  25

<210> SEQ ID NO 233
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Ala
            20                  25

<210> SEQ ID NO 234
<211> LENGTH: 31
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 234

Gly Val Ile Pro Cys Gly Glu Ser Cys Val Phe Ile Pro Cys Ile Ser
1               5                   10                  15

Thr Val Ile Gly Cys Ser Cys Lys Asn Lys Val Cys Tyr Arg Asn
            20                  25                  30

<210> SEQ ID NO 235
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gly Val Pro Cys Ala Glu Ser Cys Val Trp Ile Pro Cys Thr Val Thr
1               5                   10                  15

Ala Leu Leu Gly Cys Ser Cys Lys Asp Lys Val Cys Tyr Leu Asn
            20                  25                  30

<210> SEQ ID NO 236
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Ile Pro Cys Gly Glu Ser Cys His Ile Pro Cys Val Thr Ser Ala
1               5                   10                  15

Ile Gly Cys Ser Cys Arg Asn Arg Ser Cys Met Arg Asn
            20                  25

<210> SEQ ID NO 237
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gly Ser Gln Ser Cys Gly Glu Ser Cys Val Leu Ile Pro Cys Ile Ser
1               5                   10                  15

Gly Val Ile Gly Cys Ser Cys Ser Ser Met Ile Cys Tyr Phe Asn
            20                  25                  30

<210> SEQ ID NO 238
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Gly Ile Pro Cys Gly Glu Ser Cys Val Phe Ile Pro Cys Leu Thr Ala
1               5                   10                  15

Ala Ile Gly Cys Ser Cys Arg Ser Lys Val Cys Tyr Arg Asn
            20                  25                  30
```

<210> SEQ ID NO 239
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Leu Pro Val Cys Gly Glu Thr Cys Val Gly Gly Thr Cys Asn Thr
1               5                   10                  15

Pro Gly Cys Ser Cys Ser Ile Pro Val Cys Thr Arg Asn
            20                  25

<210> SEQ ID NO 240
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Leu Pro Val Cys Gly Glu Thr Cys Val Gly Gly Thr Cys Asn Thr
1               5                   10                  15

Pro Gly Cys Ser Cys Ser Trp Pro Val Cys Phe Arg Asp
            20                  25

<210> SEQ ID NO 241
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gly Ala Pro Val Cys Gly Glu Thr Cys Phe Gly Gly Thr Cys Asn Thr
1               5                   10                  15

Pro Gly Cys Thr Cys Asp Pro Trp Pro Val Cys Thr Asn Asp
            20                  25                  30

<210> SEQ ID NO 242
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Leu Pro Val Cys Gly Glu Thr Cys Val Gly Gly Thr Cys Asn Thr
1               5                   10                  15

Pro Tyr Cys Thr Cys Ser Trp Pro Val Cys Thr Arg Asp
            20                  25

<210> SEQ ID NO 243
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

```
Gly Leu Pro Val Cys Gly Glu Thr Cys Val Gly Gly Thr Cys Asn Thr
1               5                   10                  15

Glu Tyr Cys Thr Cys Ser Trp Pro Val Cys Thr Arg Asp
            20                  25
```

<210> SEQ ID NO 244
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

```
Gly Leu Pro Val Cys Gly Glu Thr Cys Val Gly Gly Thr Cys Asn Thr
1               5                   10                  15

Pro Tyr Cys Phe Cys Ser Trp Pro Val Cys Thr Arg Asp
            20                  25
```

<210> SEQ ID NO 245
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

```
Gly Ile Pro Cys Gly Glu Ser Cys Val Trp Ile Pro Cys Ile Ser Gly
1               5                   10                  15

Ala Ile Gly Cys Ser Cys Lys Ser Lys Val Cys Tyr Lys Asn
            20                  25                  30
```

<210> SEQ ID NO 246
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

```
Gly Ile Pro Cys Gly Glu Ser Cys Val Trp Ile Pro Cys Ile Ser Ser
1               5                   10                  15

Ala Ile Gly Cys Ser Cys Lys Asn Lys Val Cys Phe Lys Asn
            20                  25                  30
```

<210> SEQ ID NO 247
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

```
Gly Ser Ile Pro Ala Cys Gly Glu Ser Cys Phe Arg Gly Lys Cys Tyr
1               5                   10                  15

Thr Pro Gly Cys Ser Cys Ser Lys Tyr Pro Leu Cys Ala Lys Asp
            20                  25                  30
```

<210> SEQ ID NO 248
<211> LENGTH: 31
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 248

Gly Ser Ile Pro Ala Cys Gly Glu Ser Cys Phe Lys Gly Trp Cys Tyr
1               5                   10                  15

Thr Pro Gly Cys Ser Cys Ser Lys Tyr Pro Leu Cys Ala Lys Asp
            20                  25                  30

<210> SEQ ID NO 249
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Gly Ser Phe Pro Cys Gly Glu Ser Cys Val Phe Ile Pro Cys Ile Ser
1               5                   10                  15

Ala Ile Ala Gly Cys Ser Cys Lys Asn Lys Val Cys Tyr Lys Asn
            20                  25                  30

<210> SEQ ID NO 250
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gly Ile Pro Cys Gly Glu Ser Cys Val Phe Ile Pro Cys Ile Thr Ala
1               5                   10                  15

Ala Ile Gly Cys Ser Cys Lys Thr Lys Val Cys Tyr Arg Asn
            20                  25                  30

<210> SEQ ID NO 251
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Gly Val Ile Pro Cys Gly Glu Ser Cys Val Phe Ile Pro Cys Ile Ser
1               5                   10                  15

Ala Val Leu Gly Cys Ser Cys Lys Ser Lys Val Cys Tyr Arg Asn
            20                  25                  30

<210> SEQ ID NO 252
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Gly Ile Pro Cys Gly Glu Thr Cys Val Phe Met Pro Cys Ile Ser Gly
1               5                   10                  15

Pro Met Gly Cys Ser Cys Lys His Met Val Cys Tyr Arg Asn
```

-continued

```
                 20                  25                  30

<210> SEQ ID NO 253
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Gly Val Ile Pro Cys Gly Glu Ser Cys Val Phe Ile Pro Cys Ile Ser
1               5                   10                  15

Ser Val Leu Gly Cys Ser Cys Lys Asn Lys Val Cys Tyr Arg Asn
                 20                  25                  30

<210> SEQ ID NO 254
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Gly Ser Ala Phe Gly Cys Gly Glu Thr Cys Val Lys Gly Lys Cys Asn
1               5                   10                  15

Thr Pro Gly Cys Val Cys Ser Trp Pro Val Cys Lys Lys Asn
                 20                  25                  30

<210> SEQ ID NO 255
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ala Pro Cys Gly Glu Ser Cys Val Phe Ile Pro Cys Ile Ser Ala Val
1               5                   10                  15

Leu Gly Cys Ser Cys Lys Ser Lys Val Cys Tyr Arg Asn
                 20                  25

<210> SEQ ID NO 256
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Gly Val Pro Cys Gly Glu Ser Cys Val Trp Val Pro Cys Thr Val Thr
1               5                   10                  15

Ala Leu Met Gly Cys Ser Cys Val Arg Glu Val Cys Arg Lys Asp
                 20                  25                  30

<210> SEQ ID NO 257
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 257

Gly Ile Pro Cys Ala Glu Ser Cys Val Trp Ile Pro Cys Thr Val Thr
1               5                   10                  15

Lys Met Leu Gly Cys Ser Cys Lys Asp Lys Val Cys Tyr Asn
            20                  25                  30

<210> SEQ ID NO 258
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Gly Gly Ser Ile Pro Cys Ile Glu Thr Cys Val Trp Thr Gly Cys Phe
1               5                   10                  15

Leu Val Pro Gly Cys Ser Cys Lys Ser Asp Lys Lys Cys Tyr Leu Asn
            20                  25                  30

<210> SEQ ID NO 259
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gly Gly Ser Val Pro Cys Ile Glu Thr Cys Val Trp Thr Gly Cys Phe
1               5                   10                  15

Leu Val Pro Gly Cys Ser Cys Lys Ser Asp Lys Lys Cys Tyr Leu Asn
            20                  25                  30

<210> SEQ ID NO 260
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Gly Asp Ile Pro Leu Cys Gly Glu Thr Cys Phe Glu Gly Gly Asn Cys
1               5                   10                  15

Arg Ile Pro Gly Cys Thr Cys Val Trp Pro Phe Cys Ser Lys Asn
            20                  25                  30

<210> SEQ ID NO 261
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Gly Leu Pro Thr Cys Gly Glu Thr Cys Phe Gly Gly Thr Cys Asn Thr
1               5                   10                  15

Pro Gly Cys Thr Cys Asp Pro Phe Pro Val Cys Thr His Asp
            20                  25                  30

<210> SEQ ID NO 262
<211> LENGTH: 29

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Ile Pro Val Cys Gly Glu Thr Cys Val Gly Gly Thr Cys Asn Thr
1               5                   10                  15

Pro Gly Cys Ser Cys Ser Trp Pro Val Cys Thr Arg Asn
            20                  25

<210> SEQ ID NO 263
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gly Leu Pro Ile Cys Gly Glu Thr Cys Val Gly Gly Thr Cys Asn Thr
1               5                   10                  15

Pro Gly Cys Ser Cys Ser Trp Pro Val Cys Thr Arg Asn
            20                  25

<210> SEQ ID NO 264
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gly Ile Ala Cys Gly Glu Ser Cys Val Phe Leu Gly Cys Phe Ile Pro
1               5                   10                  15

Gly Cys Ser Cys Lys Ser Lys Val Cys Tyr Phe Asn
            20                  25

<210> SEQ ID NO 265
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Ile Pro Cys Gly Glu Thr Cys Val Ala Phe Gly Cys Trp Ile Pro
1               5                   10                  15

Gly Cys Ser Cys Lys Asp Lys Leu Cys Tyr Tyr Asp
            20                  25

<210> SEQ ID NO 266
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Lys Leu Cys Gly Glu Thr Cys Phe Lys Phe Lys Cys Tyr Thr Pro Gly
1               5                   10                  15
```

Cys Ser Cys Ser Tyr Phe Pro Cys Lys
            20                  25

<210> SEQ ID NO 267
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Gly Ile Pro Cys Gly Glu Ser Cys Val Phe Ile Pro Cys Thr Val Thr
1               5                   10                  15

Ala Leu Leu Gly Cys Ser Cys Gln Asn Lys Val Cys Tyr Arg Asp
            20                  25                  30

<210> SEQ ID NO 268
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Gly Val Ile Pro Cys Gly Glu Ser Cys Val Phe Ile Pro Cys Ile Ser
1               5                   10                  15

Ser Val Leu Gly Cys Ser Cys Lys Asn Lys Val Cys Tyr Arg Asp
            20                  25                  30

<210> SEQ ID NO 269
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Gly Val Ile Pro Cys Gly Glu Ser Cys Val Phe Ile Pro Cys Ile Thr
1               5                   10                  15

Ala Ala Val Gly Cys Ser Cys Lys Asn Lys Val Cys Tyr Arg Asp
            20                  25                  30

<210> SEQ ID NO 270
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gly Leu Pro Val Cys Gly Glu Thr Cys Ala Gly Gly Thr Cys Asn Thr
1               5                   10                  15

Pro Gly Cys Ser Cys Ser Trp Pro Ile Cys Thr Arg Asn
            20                  25

<210> SEQ ID NO 271
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Gly Leu Pro Val Cys Gly Glu Thr Cys Ala Gly Gly Thr Cys Asn Thr
1               5                   10                  15

Pro Gly Cys Ser Cys Thr Trp Pro Ile Cys Thr Arg Asn
            20                  25

<210> SEQ ID NO 272
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gly Leu Pro Val Cys Gly Glu Thr Cys Ala Gly Arg Cys Asn Thr
1               5                   10                  15

Pro Gly Cys Ser Cys Ser Trp Pro Val Cys Thr Arg Asn
            20                  25

<210> SEQ ID NO 273
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Gly Leu Pro Val Cys Gly Glu Thr Cys Phe Gly Gly Thr Cys Asn Thr
1               5                   10                  15

Pro Gly Cys Thr Cys Asp Pro Trp Pro Val Cys Thr Arg Asn
            20                  25                  30

<210> SEQ ID NO 274
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Gly Leu Pro Val Cys Gly Glu Thr Cys Phe Gly Gly Thr Cys Asn Thr
1               5                   10                  15

Pro Gly Cys Ser Cys Asp Pro Trp Pro Val Cys Thr Arg Asn
            20                  25                  30

<210> SEQ ID NO 275
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Gly Leu Pro Ile Cys Gly Glu Thr Cys Phe Gly Gly Thr Cys Asn Thr
1               5                   10                  15

Pro Gly Cys Ile Cys Asp Pro Trp Pro Val Cys Thr Arg Asp
            20                  25                  30

<210> SEQ ID NO 276

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Gly Ser His Cys Gly Glu Thr Cys Phe Phe Gly Cys Tyr Lys Pro
1               5                   10                  15

Gly Cys Ser Cys Asp Glu Leu Arg Gln Cys Tyr Lys Asn
            20                  25

<210> SEQ ID NO 277
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Gly Val Pro Cys Gly Glu Ser Cys Val Phe Ile Pro Cys Leu Thr Ala
1               5                   10                  15

Val Val Gly Cys Ser Cys Ser Asn Lys Val Cys Tyr Leu Asn
            20                  25                  30

<210> SEQ ID NO 278
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Gly Leu Pro Val Cys Gly Glu Thr Cys Phe Gly Gly Thr Cys Asn Thr
1               5                   10                  15

Pro Gly Cys Ala Cys Asp Pro Trp Pro Val Cys Thr Arg Asn
            20                  25                  30

<210> SEQ ID NO 279
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Gly Val Pro Cys Ala Glu Ser Cys Val Trp Ile Pro Cys Thr Val Thr
1               5                   10                  15

Ala Leu Leu Gly Cys Ser Cys Lys Asp Lys Val Cys Tyr Leu Asp
            20                  25                  30

<210> SEQ ID NO 280
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Gly Ile Pro Cys Ala Glu Ser Cys Val Trp Ile Pro Cys Thr Val Thr
1               5                   10                  15
```

Ala Leu Leu Gly Cys Ser Cys Lys Asp Lys Val Cys Tyr Leu Asn
            20                  25                  30

<210> SEQ ID NO 281
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Gly Ile Pro Cys Ala Glu Ser Cys Val Trp Ile Pro Cys Thr Val Thr
1               5                   10                  15

Ala Leu Leu Gly Cys Ser Cys Lys Asp Lys Val Cys Tyr Leu Asp
            20                  25                  30

<210> SEQ ID NO 282
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Gly Ile Pro Cys Gly Glu Ser Cys Val Phe Ile Pro Cys Ile Ser Ser
1               5                   10                  15

Val Val Gly Cys Ser Cys Lys Ser Lys Val Cys Tyr Leu Asp
            20                  25                  30

<210> SEQ ID NO 283
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Gly Leu Pro Cys Gly Glu Ser Cys Val Phe Ile Pro Cys Ile Thr Thr
1               5                   10                  15

Val Val Gly Cys Ser Cys Lys Asn Lys Val Cys Tyr Asn Asn
            20                  25                  30

<210> SEQ ID NO 284
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Gly Leu Pro Cys Gly Glu Ser Cys Val Phe Ile Pro Cys Ile Thr Thr
1               5                   10                  15

Val Val Gly Cys Ser Cys Lys Asn Lys Val Cys Tyr Asn Asp
            20                  25                  30

<210> SEQ ID NO 285
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 285

Gly Thr Val Pro Cys Gly Glu Ser Cys Val Phe Ile Pro Cys Ile Thr
1               5                   10                  15

Gly Ile Ala Gly Cys Ser Cys Lys Asn Lys Val Cys Tyr Ile Asn
            20                  25                  30

<210> SEQ ID NO 286
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Gly Thr Val Pro Cys Gly Glu Ser Cys Val Phe Ile Pro Cys Ile Thr
1               5                   10                  15

Gly Ile Ala Gly Cys Ser Cys Lys Asn Lys Val Cys Tyr Ile Asp
            20                  25                  30

<210> SEQ ID NO 287
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

His Glu Pro Cys Gly Glu Ser Cys Val Phe Ile Pro Cys Ile Thr Thr
1               5                   10                  15

Val Val Gly Cys Ser Cys Lys Asn Lys Val Cys Tyr Asn
            20                  25

<210> SEQ ID NO 288
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

His Glu Pro Cys Gly Glu Ser Cys Val Phe Ile Pro Cys Ile Thr Thr
1               5                   10                  15

Val Val Gly Cys Ser Cys Lys Asn Lys Val Cys Tyr Asp
            20                  25

<210> SEQ ID NO 289
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Gly Leu Pro Thr Cys Gly Glu Thr Cys Thr Leu Gly Thr Cys Tyr Val
1               5                   10                  15

Pro Asp Cys Ser Cys Ser Trp Pro Ile Cys Met Lys Asn
            20                  25

```
<210> SEQ ID NO 290
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gly Ser Ala Phe Cys Gly Glu Thr Cys Val Leu Gly Thr Cys Tyr Thr
1               5                   10                  15

Pro Asp Cys Ser Cys Thr Ala Leu Val Cys Leu Lys Asn
                20                  25

<210> SEQ ID NO 291
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Gly Ile Pro Cys Gly Glu Ser Cys Val Phe Ile Pro Cys Ile Thr Gly
1               5                   10                  15

Ile Ala Gly Cys Ser Cys Lys Ser Lys Val Cys Tyr Arg Asn
                20                  25                  30

<210> SEQ ID NO 292
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gly Ile Pro Cys Gly Glu Ser Cys Val Phe Ile Pro Cys Ile Thr Ala
1               5                   10                  15

Ala Ile Gly Cys Ser Cys Lys Ser Lys Val Cys Tyr Arg Asn
                20                  25                  30

<210> SEQ ID NO 293
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Gly Ile Pro Cys Gly Glu Ser Cys Val Phe Ile Pro Cys Ile Ser Thr
1               5                   10                  15

Val Ile Gly Cys Ser Cys Lys Asn Lys Val Cys Tyr Arg Asn
                20                  25                  30

<210> SEQ ID NO 294
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Gly Ile Pro Cys Gly Glu Ser Cys Val Phe Ile Pro Cys Thr Val Thr
```

```
                1               5                  10                  15
Ala Leu Leu Gly Cys Ser Cys Lys Asp Lys Val Cys Tyr Lys Asn
             20                  25                  30

<210> SEQ ID NO 295
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Gly Val Pro Ile Cys Gly Glu Ser Cys Val Gly Thr Cys Asn Thr
1               5                  10                  15

Pro Gly Cys Ser Cys Ser Trp Pro Val Cys Thr Thr Asn
             20                  25

<210> SEQ ID NO 296
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Gly Leu Pro Ile Cys Gly Glu Thr Cys Val Gly Thr Cys Asn Thr
1               5                  10                  15

Pro Gly Cys Phe Cys Thr Trp Pro Val Cys Thr Arg Asn
             20                  25

<210> SEQ ID NO 297
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gly Leu Pro Val Cys Gly Glu Thr Cys Phe Thr Gly Ser Cys Tyr Thr
1               5                  10                  15

Pro Gly Cys Ser Cys Asn Trp Pro Val Cys Asn Arg Asn
             20                  25

<210> SEQ ID NO 298
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gly Leu Pro Val Cys Gly Glu Thr Cys Val Gly Thr Cys Asn Thr
1               5                  10                  15

Pro Gly Cys Ser Cys Ser Trp Pro Val Cys Phe Arg Asn
             20                  25

<210> SEQ ID NO 299
<211> LENGTH: 31
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 299

Gly Leu Thr Pro Cys Gly Glu Ser Cys Val Trp Ile Pro Cys Ile Ser
1               5                   10                  15

Ser Val Val Gly Cys Ala Cys Lys Ser Lys Val Cys Tyr Lys Asp
            20                  25                  30

<210> SEQ ID NO 300
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Gly Thr Arg Cys Gly Glu Thr Cys Phe Val Leu Pro Cys Trp Ser Ala
1               5                   10                  15

Lys Phe Gly Cys Tyr Cys Gln Lys Gly Phe Cys Tyr Arg Asn
            20                  25                  30

<210> SEQ ID NO 301
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Gly Gly Val Cys Pro Lys Ile Leu Gln Arg Cys Arg Arg Asp Ser Asp
1               5                   10                  15

Cys Pro Gly Ala Cys Ile Cys Arg Gly Asn Gly Tyr Cys Ser Ser Gly
            20                  25                  30

<210> SEQ ID NO 302
<211> LENGTH: 485
<212> TYPE: PRT
<213> ORGANISM: Homo sapiens

<400> SEQUENCE: 302

Met Arg Lys Arg Ala Pro Gln Ser Glu Met Ala Pro Ala Gly Val Ser
1               5                   10                  15

Leu Arg Ala Thr Ile Leu Cys Leu Leu Ala Trp Ala Gly Leu Ala Ala
            20                  25                  30

Gly Asp Arg Val Tyr Ile His Pro Phe His Leu Val Ile His Asn Glu
        35                  40                  45

Ser Thr Cys Glu Gln Leu Ala Lys Ala Asn Ala Gly Lys Pro Lys Asp
    50                  55                  60

Pro Thr Phe Ile Pro Ala Pro Ile Gln Ala Lys Thr Ser Pro Val Asp
65                  70                  75                  80

Glu Lys Ala Leu Gln Asp Gln Leu Val Leu Val Ala Ala Lys Leu Asp
                85                  90                  95

Thr Glu Asp Lys Leu Arg Ala Ala Met Val Gly Met Leu Ala Asn Phe
            100                 105                 110

Leu Gly Phe Arg Ile Tyr Gly Met His Ser Glu Leu Trp Gly Val Val
        115                 120                 125

His Gly Ala Thr Val Leu Ser Pro Thr Ala Val Phe Gly Thr Leu Ala
    130                 135                 140

```
Ser Leu Tyr Leu Gly Ala Leu Asp His Thr Ala Asp Arg Leu Gln Ala
145                 150                 155                 160

Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
            180                 185                 190

Ala Gln Gly Arg Ala Asp Ser Gln Ala Gln Leu Leu Leu Ser Thr Val
            195                 200                 205

Val Gly Val Phe Thr Ala Pro Gly Leu His Leu Lys Gln Pro Phe Val
    210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Thr Gly Ala Ser Val
            260                 265                 270

Asp Ser Thr Leu Ala Phe Asn Thr Tyr Val His Phe Gln Gly Lys Met
            275                 280                 285

Lys Gly Phe Ser Leu Leu Ala Glu Pro Gln Glu Phe Trp Val Asp Asn
    290                 295                 300

Ser Thr Ser Val Ser Val Pro Met Leu Ser Gly Met Gly Thr Phe Gln
305                 310                 315                 320

His Trp Ser Asp Ile Gln Asp Asn Phe Ser Val Thr Gln Val Ser Phe
                325                 330                 335

Thr Glu Ser Ala Cys Leu Leu Leu Ile Gln Pro His Tyr Ala Ser Asp
            340                 345                 350

Leu Asp Lys Val Glu Gly Leu Thr Phe Gln Gln Asn Ser Leu Asn Trp
            355                 360                 365

Met Lys Lys Leu Ser Pro Arg Thr Ile His Leu Thr Met Pro Gln Leu
    370                 375                 380

Val Leu Gln Gly Ser Tyr Asp Leu Gln Asp Leu Leu Ala Gln Ala Glu
385                 390                 395                 400

Leu Pro Ala Ile Leu His Thr Glu Leu Asn Leu Gln Lys Leu Ser Asn
                405                 410                 415

Asp Arg Ile Arg Val Gly Glu Val Leu Asn Ser Ile Phe Phe Glu Leu
            420                 425                 430

Glu Ala Asp Glu Arg Glu Pro Thr Glu Ser Thr Gln Gln Leu Asn Lys
            435                 440                 445

Pro Glu Val Leu Glu Val Thr Leu Asn Arg Pro Phe Leu Phe Ala Val
    450                 455                 460

Tyr Asp Gln Ser Ala Thr Ala Leu His Phe Leu Gly Arg Val Ala Asn
465                 470                 475                 480

Pro Leu Ser Thr Ala
            485
```

PROTEOLICALLY RESISTANT CYCLOTIDES WITH ANGIOTENSIN 1-7 LIKE ACTIVITY

CROSS-REFERENCE TO RELATED APPLICATION

This application is a Continuation of U.S. application Ser. No. 15/422,376, filed Feb. 1, 2017, which claims priority under 35 U.S.C. § 119(e) to U.S. Provisional Patent Application No. 62/290,329, filed Feb. 2, 2016, the entire contents of each of which are hereby incorporated by reference into the present disclosure.

STATEMENT OF GOVERNMENT SUPPORT

This invention was made with government support under Grant Nos. R01-GM090323, R01-GM113363, and R01-GM085006 awarded by National Institutes of Health (NIH). The government has certain rights in the invention.

FIELD OF DISCLOSURE

This disclosure relates generally to the field of therapeutic cyclic peptides, specifically for use in cancer treatment.

BACKGROUND

Modulation of the renin-angiotensin system (RAS) by angiotensin-(1-7) (AT1-7) is recently emerged as an attractive and novel chemotherapeutic and chemopreventive treatment for lung cancer. AT1-7 is a component of the renin-angiotensin system (RAS) with vasodilator, antiproliferative and anti-angiogenic properties. Recent studies have shown that AT1-7 is able to reduce serum-stimulated growth of human lung cancer cells both in vitro and in vivo through activation of the unique AT1-7 receptor, MAS1. In results with human lung adenocarcinoma xenografts, AT1-7 was able to inhibit tumor growth through reduction in cyclooxygenase-2 (COX-2) activity and production of pro-inflammatory prostaglandins. In contrast, AT1-7 had no effect on cyclooxygenase 1 (COX-1) activity in the same xenograft tumor. All these suggest that selective activation of the MAS1 receptor may represent a novel treatment for lung cancer through reduction of COX-2 activity. Unfortunately, AT1-7 has a limited clinical potential due to its unfavorable pharmacokinetic profile.

SUMMARY

Cyclotides are small globular microproteins typically ranging from 28 to 37 amino acids with a unique head-to-tail cyclized backbone topology that is stabilized by three disulfide bonds. The number and positions of cysteine residues are conserved throughout the family, forming the cyclic cystine-knot (CCK) motif that acts as a highly stable and versatile framework on which hyper-variable loops are arranged. This cyclic cystine-knot (CCK) framework provides an extremely rigid molecular scaffold with exceptional to resistance to thermal, chemical and biological degradation. Cyclotides can be considered as natural combinatorial peptide libraries structurally constrained by the cystine-knot scaffold and head-to-tail cyclization but in which hypermutation of essentially all residues is permitted with the exception of the strictly conserved cysteines that comprise the knot.

Naturally-occurring cyclotides have shown to possess various pharmacologically-relevant activities, and have been reported to be able to cross mammalian cell membranes to antagonize intracellular protein-protein interactions in animal models. The main features of cyclotides are a remarkable stability due to the CCK framework, a small size making them readily accessible to chemical synthesis, and an excellent tolerance to sequence variations. Altogether, these features make the cyclotide scaffold an excellent molecular framework for the design of novel peptide-based therapeutics making them ideal substrates for molecular grafting of biological peptide epitopes.

The peptide AT1-7 is a hormone that in general counteracts the angiotensin II through its own signaling pathway involving the MAS receptor. Studies in animal models show that AT1-7 has ample therapeutic potential in cardiovascular disease, and more recently in lung cancer chemotherapy and chemoprevention. Despite its potential therapeutic value, AT1-7 does not offer ideal prospects for clinical use due to its poor pharmacodynamics and pharmacokinetic properties, mostly due to its rapid degradation in plasma.

Disclosed herein for the first time is the design and synthesis engineered cyclotides with similar biological activity to that of angiotensin polypeptides, e.g., the peptide AT1-7. The engineered cyclotide is able to fold correctly and shows high resistance to degradation by human serum therefore providing a promising new peptide-based lead for the treatment of cancer and myocardial infarction.

In one aspect, described herein are the design and synthesis of a novel cyclotide able to activate the unique receptor of angiotensin-(1-7) (AT1-7), the MAS1 receptor. This was accomplished by grafting an AT1-7 peptide analog onto loop 6 of cyclotide MCoTI-I using isopeptide bonds to preserve the α-amino and C-terminal carboxylate groups of AT1-7, which are required for activity. The resulting cyclotide construct was able to adopt a cyclotide-like conformation and showed similar activity to that of AT1-7. This cyclotide also showed high stability in human serum thereby providing a promising lead compound for the design of a novel type of peptide based in the treatment of cancer and myocardial infarction.

Additional advantages and other features of the present disclosure will be set forth in part in the description which follows and in part will become apparent to those having ordinary skill in the art upon examination of the following or may be learned from the practice of the disclosure. The advantages of the disclosure may be realized and obtained as particularly pointed out in the appended claims.

As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows design of grafted cyclotide MCo-AT1-7 to activate the receptor MAS1. The upper part of the panel shows the primary and tertiary structures of the cyclotide MCoTI-I (structure is based on a homology model using the solution structure of MCoTI-II as template (PDB: 1IB9)), and the primary structure of peptide angiotensin 1-7 (AT1-7). The cyclized polypeptide is stabilized by three-disulfide bonds between cysteines as shown as lines connecting residues 4 and 21, 11 and 23, and 17 and 29. The lower part of the figure shows the strategy used to graft an AT1-7-derived peptide onto the loop 6 of cyclotide MCoTI-I. The AT1-7-derived peptide was linked to the cyclotide backbone through the side-side chains of the N- and C-terminal residues forming two isopeptide bonds. The sequences corresponding to the AT1-7-derived peptides are shown linked at the carboxy terminal end to residue 1 of MCoTI-I and at the amino terminal end to residue 32. Residue X represents L-2,3-diaminopropionic acid.

FIG. 2A shows analytical High Performance Liquid Chromatography (HPLC) traces of for the linear thioester precursor, GSH-induced cyclization/folding crude after 24 hours and purified cyclotide. An asterisk indicates the desired peptide. FIG. 2B shows an analytical HPLC trace and an electrospray mass spectrometry (ES-MS) characterization of pure MCo-AT1-7. The molecular weight is 4234.2+/−0.6 Da and the expected average molecular weight is 4234.9 Da.

FIG. 7 shows stability of cyclotides MCo-AT1-7 and MCoTI-I; and peptides AT1-7 and reduced linear MCo-AT1-7 precursor to human serum at 37° C. Undigested peptides were quantified by HPLC-MS/MS.

FIGS. 8A-8B show the MCo-AT1-7 fold is similar to that of MCoTI-I. FIG. 8A shows the amide protons from the 1H{1H}-NOESY spectrum of MCo-AT1-7 are well dispersed (from 6.5 ppm to 9.8 ppm) and exhibit a large number of cross-peaks, which is indicative of a well-structured protein. FIG. 8B shows overlay of the 1H{1H}-NOESY spectra of MCo-AT1-7 (black) and MCoTI-I (gray) shows that these two spectra are very similar; chemical shift differences of amide and/or alpha protons of the proteins are less than 0.2 ppm.

DETAILED DESCRIPTION

Figure 2A:
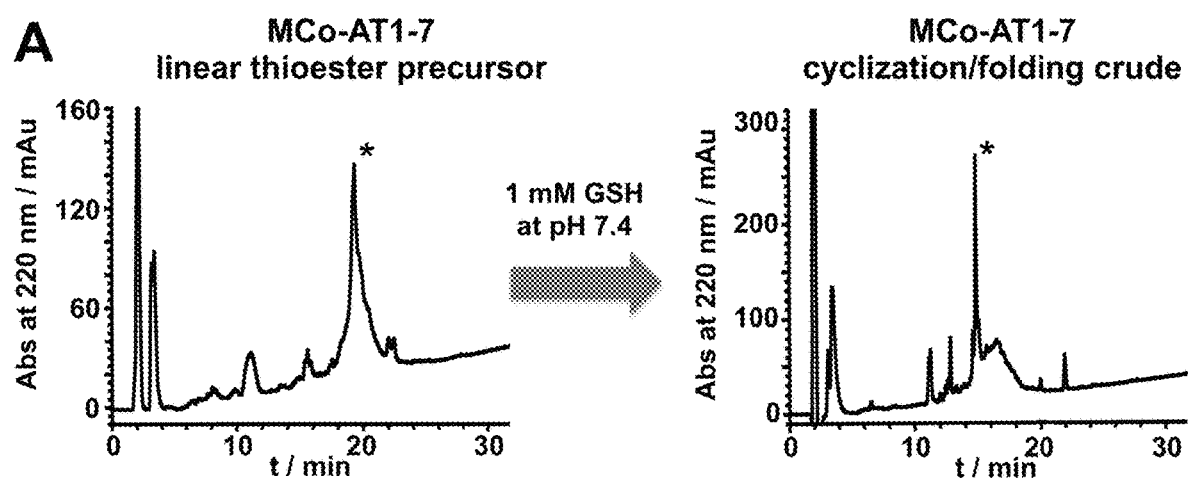
FIGS. 2A-2B show chemical synthesis and characterization of cyclotide MCo-AT1-7.

This disclosure references various publications, patents and published patent specifications by an identifying citation or an Arabic number. The full citations for the disclosures referenced by an Arabic number are found immediately preceding the claims. The disclosures of these publications, patents and published patent specifications are hereby incorporated by reference into the present disclosure in their entirety to more fully describe the state of the art to which this invention pertains.

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, $3^{rd}$ edition (Cold Spring Harbor Laboratory Press (2002)); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Harlow and Lane, eds. (1999) Using Antibodies, A Laboratory Manual; Animal Cell Culture (R. I. Freshney, ed. (1987)); Zigova, Sanberg and Sanchez-Ramos, eds. (2002) Neural Stem Cells.

Definitions

All numerical designations, e.g., pH, temperature, time, concentration, and molecular weight, including ranges, are approximations which are varied (+) or (−) by increments of 0.1 or 1 where appropriate. It is to be understood, although not always explicitly stated that all numerical designations are preceded by the term "about". The term "about" also includes the exact value "X" in addition to minor increments of "X" such as "X+0.1 or 1" or "X−0.1 or 1," where appropriate. It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

As used in the specification and claims, the singular form "a", "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to proteins, polypeptides, cells, nucleic acids, such as DNA or RNA, refers to molecules separated from other proteins, polypeptides, cells, nucleic acids, such as DNA or RNA, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together. A recombinant polynucleotide is a polynucleotide created or replicated using techniques (chemical or using host cells) other than by a cell in its native environment.

A "subject," "individual" or "patient" is used interchangeably herein and refers to a vertebrate, for example a primate, a mammal or preferably a human. Mammals include, but are not limited to equines, canines, bovines, ovines, murines, rats, simians, humans, farm animals, sport animals and pets.

"Cells," "host cells" or "recombinant host cells" are terms used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

"Amplify" "amplifying" or "amplification" of a polynucleotide sequence includes methods such as traditional cloning methodologies, PCR, ligation amplification (or ligase chain reaction, LCR) or other amplification methods. These methods are known and practiced in the art. See, e.g., U.S. Pat. Nos. 4,683,195 and 4,683,202 and Innis et al. (1990) Mol. Cell Biol. 10(11):5977-5982 (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "genotype" refers to the specific allelic composition of an entire cell, a certain gene or a specific polynucleotide region of a genome, whereas the term "phenotype" refers to the detectable outward manifestations of a specific genotype.

As used herein, the term "gene" or "recombinant gene" refers to a nucleic acid molecule comprising an open reading frame and including at least one exon and (optionally) an intron sequence. A gene may also refer to a polymorphic or a mutant form or allele of a gene.

"Homology" or "identity" or "similarity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+SwissProtein+SPupdate+ PIR. Details of these programs can be found at the following Internet address: http://www.ncbi.nlm.nih.gov/blast/Blast.cgi, last accessed on May 21, 2008. Biologically equivalent polynucleotides are those having the above-noted specified percent homology and encoding a polypeptide having the same or similar biological activity.

In one aspect, the term "equivalent" as it refers to polypeptides, proteins, or polynucleotides refers to polypeptides, oligopeptides, proteins, or polynucleotides, respectively having a sequence having a certain degree of homology or identity with the reference sequence of the polypeptides, proteins, or polynucleotides (or complement thereof when referring to polynucleotides). A homolog of a double stranded nucleic acid is intended to include nucleic acids having a nucleotide sequence that has a certain degree of homology with or with the complement thereof. In one aspect, homologs of nucleic acids are capable of hybridizing to the nucleic acid or complement thereof. In one aspect, an equivalent has at least 70%, or at least 75% or at least 80%, or at least 85%, or at least 90%, or at least 95%, or at least 97%, or at least 98%, sequence identity to the reference polynucleotide or polypeptide. The term "equivalent" may also refer to a cyclotide equivalent that comprises a polypeptide that maintains a cysteine-knot scaffold and head-to-tail cyclization but in which hypermutation of essentially all residues is permitted with the exception of the strictly conserved cysteines that comprise the knot.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

As used herein, the term "oligonucleotide" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The terms "polypeptide," "oligopeptide," "protein," and "peptide" are used interchangeably and refer to a polymer of amino acids of any length, held together by amide bonds. Polypeptides can have any primary, secondary, tertiary, or quaternary structure and may perform any function, known or unknown. A polypeptide can comprise standard amino acids, modified amino acids, unnatural amino acids, enantiomers, and analogs thereof. If present, modifications to the amino acids can be imparted before or after assembly, synthesis, or translation of the polypeptide. A polypeptide can be further modified by conjugation with a labeling component.

As used herein, the term "carrier" encompasses any of the standard carriers, such as a phosphate buffered saline solution, buffers, water, and emulsions, such as an oil/water or water/oil emulsion, and various types of wetting agents. The compositions also can include stabilizers and preservatives. For examples of carriers, stabilizers and adjuvants, see Sambrook and Russell (2001), supra. Those skilled in the art will know many other suitable carriers for binding polynucleotides, or will be able to ascertain the same by use of routine experimentation. In one aspect of the invention, the carrier is a buffered solution such as, but not limited to, a PCR buffer solution.

A "gene delivery vehicle" is defined as any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection, sometimes called transduction), transfection, transformation or various other protein-based or lipid-based gene delivery complexes) as well as techniques facilitating the delivery of "naked" polynucleotides (such as electroporation, "gene gun" delivery and various other techniques used for the introduction of polynucleotides). Unless otherwise specified, the term transfected, transduced or transformed may be used interchangeably herein to indicate the presence of exogenous polynucleotides or the expressed polypeptide therefrom in a cell. The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A cell that "stably expresses" an exogenous polypeptide is one that continues to express a polypeptide encoded by an exogenous gene introduced into the cell either after replication if the cell is dividing or for longer than a day, up to about a week, up to about two weeks, up to three weeks, up to four weeks, for several weeks, up to a month, up to two months, up to three months, for several months, up to a year or more.

The term "express" refers to the production of a gene product. When used in reference to a cancer cell or a tumor cell, "express" may also refer to an increased or abnormal level of production of a gene product by the cancer or tumor cell relative to normal cells.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

A "gene product" or alternatively a "gene expression product" refers to the RNA generated when a gene is transcribed or the amino acid (e.g., peptide or polypeptide) generated when a gene is transcribed and translated.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, a "vector" is a vehicle for transferring genetic material into a cell. Examples of such include, but are not limited to plasmids and viral vectors. A viral vector is a virus that has been modified to transduct genetic material into a cell. A plasmid vector is made by splicing a DNA construct into a plasmid. As is apparent to those of skill in the art, the appropriate regulatory elements are included in the vectors to guide replication and/or expression of the genetic material in the selected host cell.

A "viral vector" is defined as a recombinantly produced virus or viral particle that comprises a polynucleotide to be delivered into a host cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying et al. (1999) Nat. Med. 5(7):823-827.

In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. Retroviruses carry their genetic information in the form of RNA; however, once the virus infects a cell, the RNA is reverse-transcribed into the DNA form which integrates into the genomic DNA of the infected cell. The integrated DNA form is called a provirus. As used herein, retroviral vector refers to a viral particle capable of introducing exogenous nucleic acid into a cell through a viral or viral-like entry mechanism. A "lentiviral vector" is a type of retroviral vector well-known in the art that has certain advantages in transducing nondividing cells as compared to other retroviral vectors. See, Trono D. (2002) Lentiviral Vectors, New York: Spring-Verlag Berlin Heidelberg.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., a cell surface marker found on stem cells.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmic vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacteria produces proteins to confer its antibiotic resistance, it can also be induced to produce large amounts of proteins from the inserted gene. This is a cheap and easy way of mass-producing a gene or the protein it then codes for.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. A eukaryotic host, including, for example, yeast, higher plant, insect and mammalian cells. Non-limiting examples include simian, bovine, ovine, porcine, murine, rats, canine, equine, feline, avian, reptilian and human.

"Prokaryotic cells" that usually lack a nucleus or any other membrane-bound organelles and are divided into two domains, bacteria and archaea. Additionally, instead of having chromosomal DNA, these cells' genetic information is in a circular loop called a plasmid. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to prokaryotic Cyanobacteria, bacillus bacteria, *E. coli* bacterium, and *Salmonella* bacterium.

The term "propagate" means to grow a cell or population of cells. The term "growing" also refers to the proliferation of cells in the presence of supporting media, nutrients, growth factors, support cells, or any chemical or biological compound necessary for obtaining the desired number of cells or cell type.

The term "culturing" refers to the in vitro propagation of cells or organisms on or in media of various kinds. It is understood that the descendants of a cell grown in culture may not be completely identical (i.e., morphologically, genetically, or phenotypically) to the parent cell.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels are described and exemplified herein.

A "primer" is a short polynucleotide, generally with a free 3'—OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in MacPherson et al. (1991) PCR: A Practical Approach, IRL Press at Oxford University Press. All processes of producing replicate copies of a polynucleotide, such as PCR or gene cloning, are collectively referred to herein as "replication." A primer can also be used as a probe in hybridization reactions, such as Southern or Northern blot analyses. Sambrook et al., supra. The primers may optionally contain detectable labels and are exemplified and described herein.

As used herein, the term "detectable label" intends a directly or indirectly detectable compound or composition (other than a naturally occurring polynucleotide in its natural environment) that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluoresecence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6$^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Attachment of the fluorescent label may be either directly to the cellular component or compound or alternatively, can be via a linker. Suitable binding pairs for use in indirectly linking the fluorescent label to the intermediate include, but are not limited to, antigens/antibodies, e.g., rhodamine/anti-rhodamine, biotin/avidin and biotin/strepavidin.

As used herein, the term "purification marker" refers to at least one marker useful for purification or identification. A non-exhaustive list of this marker includes His, lacZ, GST, maltose-binding protein, NusA, BCCP, c-myc, CaM, FLAG, GFP, YFP, cherry, thioredoxin, poly(NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa fluors, FITC, TRITC or any other fluorescent dye or hapten.

The phrase "solid support" refers to non-aqueous surfaces such as "culture plates" "gene chips" or "microarrays." Such gene chips or microarrays can be used for diagnostic and therapeutic purposes by a number of techniques known to one of skill in the art. In one technique, oligonucleotides are attached and arrayed on a gene chip for determining the DNA sequence by the hybridization approach, such as that outlined in U.S. Pat. Nos. 6,025,136 and 6,018,041. The polynucleotides of this invention can be modified to probes, which in turn can be used for detection of a genetic sequence. Such techniques have been described, for example, in U.S. Pat. Nos. 5,968,740 and 5,858,659. A probe also can be attached or affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Various "gene chips" or "microarrays" and similar technologies are known in the art. Examples of such include, but are not limited to, LabCard (ACLARA Bio Sciences Inc.); GeneChip (Affymetric, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.); a thermal jet spotting system (Hewlett Packard Company); Hyseq HyChip (Hyseq, Inc.); BeadArray (Illumina, Inc.); GEM (Incyte Microarray Systems); a high-throughput microarry system that can dispense from 12 to 64 spots onto multiple glass slides (Intelligent Bio-Instruments); Molecular Biology Workstation and NanoChip (Nanogen, Inc.); a microfluidic glass chip (Orchid Biosciences, Inc.); BioChip Arrayer with four PiezoTip piezoelectric drop-on-demand tips (Packard Instruments, Inc.); Flex-Jet (Rosetta Inpharmatic, Inc.); MALDI-TOF mass spectrometer (Sequnome); ChipMaker 2 and ChipMaker 3 (TeleChem International, Inc.); and GenoSensor (Vysis, Inc.) as identified and described in Heller (2002) Annu. Rev. Biomed. Eng. 4:129-153. Examples of "gene chips" or a "microarrays" are also described in U.S. Patent Publication Nos.: 2007/0111322; 2007/0099198; 2007/0084997; 2007/0059769 and 2007/0059765 and U.S. Pat. Nos. 7,138,506; 7,070,740 and 6,989,267.

In one aspect, "gene chips" or "microarrays" containing probes or primers homologous to a polynucleotide described herein are prepared. A suitable sample is obtained from the patient, extraction of genomic DNA, RNA, protein or any combination thereof is conducted and amplified if necessary. The sample is contacted to the gene chip or microarray panel under conditions suitable for hybridization of the gene(s) or gene product(s) of interest to the probe(s) or primer(s) contained on the gene chip or microarray. The probes or primers may be detectably labeled thereby identifying the sequence(s) of interest. Alternatively, a chemical or biological reaction may be used to identify the probes or primers which hybridized with the DNA or RNA of the gene(s) of interest. The genotypes or phenotype of the patient is then determined with the aid of the aforementioned apparatus and methods.

A "solid tumor" is an abnormal mass of tissue that usually does not contain cysts or liquid areas. Solid tumors can be benign or malignant. Different types of solid tumors are named for the type of cells that form them. Examples of solid tumors include sarcomas, carcinomas, and lymphomas. As used herein, "cancer" may refer both to precancerous cells as well as cancerous cells of a tumor such as a solid tumor.

The term "lung cancer" refers to a type of cancer that develops in the lung. The peptides of the present disclosure are useful for treatment of both primary lung cancers (carcinomas) and cancers that metastasized to the lung. Lung cancers include, but are not limited to small-cell lung carcinoma and non-small-cell lung carcinoma. MAS1 mRNA and protein have been detected in the lung cancer cell lines SK-LU-1, SK-MES-1, and A549 lung cancer cell lines. See Gallagher et al., Inhibition of human lung cancer cell growth by angiotensin-(1-7), Carcinogenesis 2004, 25(11):20145-52.

The term "breast cancer" refers to a type of cancer that develops in the breast. The peptides of the present disclosure are useful for treatment of breast cancers of any stage, including those positive for estrogen receptor, progesterone receptor, and/or HER2, as well as breast cancers "triple negative" for such receptors.

MAS1 refers to a proto-oncogene, its mRNA expression product, and its protein expression product (Accession Number NP_002368.1). The MAS1 gene encodes a class I seven-transmembrane G-protein-coupled receptor. The encoded protein is a receptor for angiotensin-(1-7) and preferentially couples to the Gq protein, activating the phospholipase C signaling pathway. The encoded protein may play a role in multiple processes including hypotension, smooth muscle relaxation and cardioprotection by mediating the effects of angiotensin-(1-7). The published protein sequence comprises (SEQ ID NO: 1):

MDGSNVTSFVVEEPTNISTGRNASVGNAHRQIPIVHWVIMSISPVGFV

ENGILLWFLCFRMRRNPFTVYITHLSIADISLLFCIFILSIDYALDYE

LSSGHYYTIVTLSVTFLFGYNTGLYLLTAISVERCLSVLYPIWYRCHR

-continued

PKYQSALVCALLWALSCLVTTMEYVMCIDREEESHSRNDCRAVIIFIA

ILSFLVFTPLMLVSSTILVVKIRKNTWASHSSKLYIVIMVTIIIFLIF

AMPMRLLYLLYYEYWSTFGNLHHISLLFSTINSSANPFIYFFVGSSKK

KRFKESLKVVLTRAFKDEMQPRRQKDNCNTVTVETVV.

MAS1 protein has been detected in many types of cancers, including breast cancer, carcinoid, cervical cancer, colorectal cancer, endometrial cancer, glioma, head and neck cancer, liver cancer, lung cancer, lymphoma, melanoma, ovarian cancer, pancreatic cancer, prostate cancer, renal cancer, skin cancer, stomach cancer, testicular cancer, thyroid cancer, and urothelial cancer (see, e.g. the Human Protein Atlas described in Ponten et al., The Human Protein Atlas as a proteomic resource for biomarker discovery, Journal of Internal Medicine 2011, November; 270(5): 428-46; Gallagher et al., Inhibition of human lung cancer cell growth by angiotensin-(1-7), Carcinogenesis 2004, 25(11):20145-52; Luo et al., Expression of MAS1 in breast cancer, Cancer Science 2015, September; 106(9): 1240-48).

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present disclosure for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. Studies in animal models generally may be used for guidance regarding effective dosages for treatment of diseases. In general, one will desire to administer an amount of the compound that is effective to achieve a serum level commensurate with the concentrations found to be effective in vitro. Thus, where a compound is found to demonstrate in vitro activity, for example as noted in the Tables discussed below one can extrapolate to an effective dosage for administration in vivo. These considerations, as well as effective formulations and administration procedures are well known in the art and are described in standard textbooks.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

"Suppressing" or "inhibiting" tumor growth indicates a growth state that is curtailed compared to growth without any therapy. Tumor cell growth can be assessed by any means known in the art, including, but not limited to, measuring tumor size, determining whether tumor cells are proliferating using a $^3$H-thymidine incorporation assay, or counting tumor cells. "Suppressing" means any or all of the following states: slowing, delaying, and "suppressing" tumor growth indicates a growth state that is curtailed when stopping tumor growth, as well as tumor shrinkage.

A "control" is an alternative subject or sample used in an experiment for comparison purpose. A control can be "positive" or "negative".

Cyclotides are small globular microproteins (ranging from 28 to 37 amino acids) with a unique head-to-tail cyclized backbone, which is stabilized by disulfide bonds forming a cystine-knot motif. This cyclic cystine-knot (CCK) framework provides a rigid molecular platform with exceptional stability towards physical, chemical and biological degradation. These microproteins can be considered natural combinatorial peptide libraries structurally constrained by the cystine-knot scaffold and head-to-tail cyclization, but in which hypermutation of essentially all residues is permitted with the exception of the strictly conserved cysteines that comprise the knot. Furthermore, naturally occurring cyclotides have shown to possess various pharmacologically relevant activities, and have been reported to cross cell membranes. Altogether, these features make the cyclotide scaffold an excellent molecular framework for the design of novel peptide-based therapeutics, making them ideal substrates for molecular grafting of biological peptide epitopes.

Descriptive Embodiments

This disclosure provides a cyclotide comprising, or consisting essentially of, or yet further consisting of, a cyclotide backbone and an peptide comprising an angiotensin polypeptide or an equivalent thereof. In one aspect, the angiotensin polypeptide comprises, or consists essentially of, or yet further consists of a polypeptide of the group of an angiotensinl-1-7 polypeptide, an angiotensin 1-4 polypeptide, or an angiotensin 1-5 polypeptide, or an equivalent of each thereof. Non-limiting examples of the angiotensin polypeptide is a polypeptide from the group of SEQ ID NO: 11, SEQ ID NO: 12, SEQ ID NO: 13 (XRVIE), wherein X is the amino acid L-2,3-diaminopropionic acid, SEQ ID NO:

14 (XRVYIHE), wherein X is the amino acid L-2,3-diaminopropionic acid, SEQ ID NO: 15, SEQ ID NO: 16, or an equivalent of each thereof. Non-limiting examples of the cyclotide backbone is a polypeptide from the group of SEQ ID NO: 2, SEQ ID NO: 3, SEQ ID NO: 4, SEQ ID NO: 5, or SEQ ID NOS: 21 to 300, or an equivalent of each thereof, wherein the equivalent comprises a polypeptide that maintains a cystine-knot scaffold and head-to-tail cyclization but in which hypermutation of essentially all residues is permitted with the exception of the strictly conserved cysteines that comprise the knot.

In another aspect, the cyclotide comprises, or alternatively consists essentially of, or yet further consists of an angiotensin-(1-7) (AT1-7) (amino acid sequence DRVYIHP, SEQ ID NO: 11) peptide grafted to a cyclotide backbone. In a further aspect, provided herein is a cyclotide from the group of SEQ ID NO: 17, SEQ ID NO: 18, SEQ ID NO: 19, SEQ ID NO: 20, or an equivalent of each thereof, wherein the equivalent comprises a polypeptide that maintains a cystine-knot scaffold and head-to-tail cyclization but in which hypermutation of essentially all residues is permitted with the exception of the strictly conserved cysteines that comprise the knot.

Cyclotides are small globular microproteins (ranging from 28 to 37 amino acids) with a unique head-to-tail cyclized backbone, which is stabilized by disulfide bonds forming a cystine-knot motif. This cyclic cystine-knot (CCK) framework provides a rigid molecular platform with exceptional stability towards physical, chemical and biological degradation. These microproteins can be considered natural combinatorial peptide libraries structurally constrained by the cystine-knot scaffold and head-to-tail cyclization, but in which hypermutation of essentially all residues is permitted with the exception of the strictly conserved cysteines that comprise the knot. Furthermore, naturally occurring cyclotides have shown to possess various pharmacologically relevant activities, and have been reported to cross cell membranes. Altogether, these features make the cyclotide scaffold an excellent molecular framework for the design of novel peptide-based therapeutics, making them ideal substrates for molecular grafting of biological peptide epitopes.

The construction of the cyclotide is known in the art and has been described previously (see WO 2011/005598, which is incorporated herein for all purposes). Synthesis of peptides useful in the methods and compositions of the disclosure are also described herein and known in the art.

The preparation of a cyclotide may also entail the generation of a linear peptide that contains the desired cyclotide in a linear form, flanked by two peptide fragments that have affinity to each other so as to be capable of bringing two ends of the linear cyclotide together, facilitating cyclization. Accordingly, the present disclosure provides a polypeptide precursor for generating a cyclotide.

In one embodiment, the angiotensin peptide is grafted into loop 6 of the cyclotide. The cyclotide comprises a molecular framework comprising a sequence of amino acids forming a cyclic backbone wherein the cyclic backbone comprises sufficient disulfide bonds to confer knotted topology on the molecular framework or part thereof. Examples of cyclic backbone polypeptides are now in the art and described herein.

Reference herein to a "cyclotide backbone" includes a molecule comprising a sequence of amino acid residues or analogues thereof without free amino and carboxy termini. The cyclic backbone of the disclosure comprises sufficient disulfide bonds, or chemical equivalents thereof, to confer a knotted topology on the three-dimensional structure of the cyclic backbone. The term "cyclotide" as used herein refers to a peptide comprising a cyclic cystine knot motif defined by a cyclic backbone, at least two but preferably at least three disulfide bonds and associated beta strands in a particular knotted topology. The knotted topology involves an embedded ring formed by at least two backbone disulfide bonds and their connecting backbone segments being threaded by a third disulfide bond. However, a disulfide bond may be replaced or substituted by a mimic of a disulfide bond such as 1,4-disubstituted 1,2,3-triazoles introduced through copper(I)-catalyzed azide-alkyne cycloaddition (CuAAC) or 1,5-disubstituted 1,2,3-triazoles introduced through a ruthenium(II)-catalyzed method (RuAAC), or another form of bonding such as an amide bond, thioethers, diselenide bond, triazoles, hydrocarbon-based bridges, ionic bonds, hydrogen bonds, or hydrophobic bonds. In some embodiments, a cyclotide backbone comprises between about 20 and about 100, between about 25 and about 50, between about 27 and about 42, between about 30 and about 40, between about 32 and about 38, or between about 28 and 37 amino acid residues.

In some embodiments, the cyclotide backbone is comprised of, or alternatively consists essentially of MCoTI-I. The sequence of MCoTI-I is described FIG. 1. In one aspect, MCoTI-I comprises the sequence GGVCPKILQRCRRDSDCPGACICRGNGYCGSGSD (SEQ ID NO: 3), or an equivalent thereof. In another aspect, the sequence comprises GGBCPKILQRCRRDSDCPGACICRGAGYCGSGSD (SEQ ID NO: 2), or an equivalent thereof. In some aspects, two residues are removed from the carboxy terminal end so that the sequence of MCoTI-I comprises or consists essentially of GGBCPKILQRCRRDSDCPGACICRGAGYCGSG (SEQ ID NO: 4) or GGVCPKILQRCRRDSDCPGACICRGNGYCGSG (SEQ ID NO: 5). In further aspect, residue B in the above sequences represents asparagine or aspartic acid.

Additional cyclotides useful in the peptides, methods, and compositions described herein are known in the art and non-limiting examples include, the cyclotides listed in Table 1 below. In some embodiments, the cyclotide backbone is derived from, comprises, or alternatively consists essentially of one or more of the sequences listed in Table 1 (SEQ ID NOS: 21-300). In some aspects, residue X in the amino acid sequences of Table 1 represents one or more unnatural amino acids.

TABLE 1

| Parental Cyclotide | SEQ ID NO: | Cyclotide Backbone Sequence |
|---|---|---|
| kalata_B1 | 21 | GLPVCGETCVGGTCNTPGCTCSWPVCTRN |
| cycloviolacin_O1 | 22 | GIPCAESCVYIPCTVTALLGCSCSNRVCYN |
| kalata_B2 | 23 | GLPVCGETCFGGTCNTPGCSCTWPICTRD |

TABLE 1-continued

| Parental Cyclotide | SEQ ID NO: | Cyclotide Backbone Sequence |
|---|---|---|
| Palicourein | 24 | GDPTFCGETCRVIPVCTYSAALGCTCDDRSDGLCKRN |
| vhr1 | 25 | GIPCAESCVWIPCTVTALLGCSCSNKVCYN |
| tricyclon_A | 26 | GGTIFDCGESCFLGTCYTKGCSCGEWKLCYGTN |
| circulin_A | 27 | GIPCGESCVWIPCISAALGCSCKNKVCYRN |
| N-KB1-C | 28 | GLPVCGETCVGGTCNTPGCTCSWPVCTRN |
| Ac-KB1-C | 29 | GLPVCGETCVGGTCNTPGCTCSWPVCTRN |
| N-KB1-Am | 30 | GLPVCGETCVGGTCNTPGCTCSWPVCTRN |
| Ac-KB1-Am | 31 | GLPVCGETCVGGTCNTPGCTCSWPVCTRN |
| Ac-[desGly]-KB1-Am | 32 | LPVCGETCVGGTCNTPGCTCSWPVCTRN |
| kalata_b1-1 | 33 | TCVGGTCNTPGCTCSWPVCTRNLPVCG |
| kalata_b1-2 | 34 | GTCNTPGCTCSWPVCTRNGLPVCGETCVG |
| kalata_b1-3 | 35 | GCTCSWPVCTRNGLPVCGETCVGGTCN |
| kalata_b1-4 | 36 | CSWPVCTRNGLPVCGETCVGGTCNTPGC |
| kalata_b1-5 | 37 | VCTRNGLPVCGETCVGGTCNTPGCTCS |
| kalata_b1-6a | 38 | VCGETCVGGTCNTPGCTCSWPVCT |
| kalata_b1-6b | 39 | RNGLPVCGETCVGGTCNTPGCTCSWPVCT |
| cycloviolacin_O2 | 40 | GIPCGESCVWIPCISSAIGCSCKSKVCYRN |
| des(24-28)kB1 | 41 | VCGETCVGGTCNTPGCTCSWPVCT |
| [Ala1,15]kB1 | 42 | GLPVAGETCVGGTCNTPGATCSWPVCTRN |
| kalata_B6 | 43 | GLPTCGETCFGGTCNTPGCSCSSWPICTRN |
| kalata_B3 | 44 | GLPTCGETCFGGTCNTPGCTCDPWPICTRD |
| kalata_B7 | 45 | GLPVCGETCTLGTCYTQGCTCSWPICKRN |
| cycloviolacin_O8 | 46 | GTLPCGESCVWIPCISSVVGCSCKSKVCYKN |
| cycloviolacin_O11 | 47 | GTLPCGESCVWIPCISAVVGCSCKSKVCYKN |
| kalata_B4 | 48 | GLPVCGETCVGGTCNTPGCTCSWPVCTRD |
| vodo_M | 49 | GAPICGESCFTGKCYTVQCSCSWPVCTRN |
| cyclopsychotride_A | 50 | SIPCGESCVFIPCTVTALLGCSCKSKVCYKN |
| cycloviolacin_H1 | 51 | GIPCGESCVYIPCLTSAIGCSCKSKVCYRN |
| cycloviolacin_O9 | 52 | GIPCGESCVWIPCLTSAVGCSCKSKVCYRN |
| vico_A | 53 | GSIPCAESCVYIPCFTGIAGCSCKNKVCYYN |
| vitri_A | 54 | GIPCGESCVWIPCITSAIGCSCKSKVCYRN |
| kalata_S | 55 | GLPVCGETCVGGTCNTPGCSCSWPVCTRN |
| cycloviolacin_O12 | 56 | GLPICGETCVGGTCNTPGCSCSWPVCTRN |
| vodo_N | 57 | GLPVCGETCTLGKCYTAGCSCSWPVCYRN |
| vico_B | 58 | GSIPCAESCVYIPCITGIAGCSCKNKVCYYN |
| kalata_B1_IIa | 59 | GLPVCGETCVGGTCNTPGCTCSWPVCTRN |
| Hypa_A | 60 | GIPCAESCVYIPCTITALLGCSCKNKVCYN |
| circulin_B | 61 | GVIPCGESCVFIPCISTLLGCSCKNKVCYRN |

TABLE 1-continued

| Parental Cyclotide | SEQ ID NO: | Cyclotide Backbone Sequence |
|---|---|---|
| circulin_C | 62 | GIPCGESCVFIPCITSVAGCSCKSKVCYRN |
| circulin_D | 63 | KIPCGESCVWIPCVTSIFNCKCENKVCYHD |
| circulin_E | 64 | KIPCGESCVWIPCLTSVFNCKCENKVCYHD |
| circulin_F | 65 | AIPCGESCVWIPCISAAIGCSCKNKVCYR |
| cycloviolacin_O4 | 66 | GIPCGESCVWIPCISSAIGCSCKNKVCYRN |
| cycloviolacin_O3 | 67 | GIPCGESCVWIPCLTSAIGCSCKSKVCYRN |
| cycloviolacin_O5 | 68 | GTPCGESCVWIPCISSAVGCSCKNKVCYKN |
| cycloviolacin_O6 | 69 | GTLPCGESCVWIPCISAAVGCSCKSKVCYKN |
| cycloviolacin_O7 | 70 | SIPCGESCVWIPCTITALAGCKCKSKVCYN |
| cycloviolacin_O10 | 71 | GIPCGESCVYIPCLTSAVGCSCKSKVCYRN |
| kalata_B5 | 72 | GTPCGESCVYIPCISGVIGCSCTDKVCYLN |
| varv_peptide_B | 73 | GLPVCGETCFGGTCNTPGCSCDPWPMCSRN |
| varv_peptide_C | 74 | GVPICGETCVGGTCNTPGCSCSWPVCTRN |
| varv_peptide_D | 75 | GLPICGETCVGGSCNTPGCSCSWPVCTRN |
| varv_peptide_F | 76 | GVPICGETCLGTCYTAGCSCSWPVCTRN |
| varv_peptide_G | 77 | GVPVCGETCFGGTCNTPGCSCDPWPVCSRN |
| varv_peptide_H | 78 | GLPVCGETCFGGTCNTPGCSCETWPVCSRN |
| cycloviolin_A | 79 | GVIPCGESCVFIPCISAAIGCSCKNKVCYRN |
| cycloviolin_B | 80 | GTACGESCYVLPCFTVGCTCTSSQCFKN |
| cycloviolin_C | 81 | GIPCGESCVFIPCLTTVAGCSCKNKVCYRN |
| cycloviolin_D | 82 | GFPCGESCVFIPCISAAIGCSCKNKVCYRN |
| violapeptide_1 | 83 | GLPVCGETCVGGTCNTPGCSCSRPVCTXN |
| vhl-1 | 84 | SISCGESCAMISFCFTEVIGCSCKNKVCYLN |
| Vontr_Protein | 85 | ALETQKPNHLEEALVAFAKKGNLGGLP |
| hcf-1 | 86 | GIPCGESCHYIPCVTSAIGCSCRNRSCMRN |
| htf-1 | 87 | GIPCGDSCHYIPCVTSTIGCSCTNGSCMRN |
| Oantr_protein | 88 | GVKSSETTLMFLKEMQLKLP |
| vhl-2 | 89 | GLPVCGETCFTGTCYTNGCTCDPWPVCTRN |
| cycloviolacin_H3 | 90 | GLPVCGETCFGGTCNTPGCICDPWPVCTRN |
| cycloviolacin_H2 | 91 | SAIACGESCVYIPCFIPGCSCRNRVCYLN |
| Hyfl_A | 92 | SISCGESCVYIPCTVTALVGCTCKDKVCYLN |
| Hyfl_B | 93 | GSPIQCAETCFIGKCYTEELGCTCTAFLCMKN |
| Hyfl_C | 94 | GSPRQCAETCFIGKCYTEELGCTCTAFLCMKN |
| Hyfl_D | 95 | GSVPCGESCVYIPCFTGIAGCSCKSKVCYYN |
| Hyfl_E | 96 | GEIPCGESCVYLPCFLPNCYCRNHVCYLN |
| Hyfl_F | 97 | SISCGETCTTFNCWIPNCKCNHHDKVCYWN |
| Hyfl_G_(partial) | 98 | CAETCVVLPCFIVPGCSCKSSVCYFN |
| Hyfl_H_(partial) | 99 | CAETCIYIPCFTEAVGCKCKDKVCYKN |
| Hyfl_I | 100 | GIPCGESCVFIPCISGVIGCSCKSKVCYRN |

TABLE 1-continued

| Parental Cyclotide | SEQ ID NO: | Cyclotide Backbone Sequence |
|---|---|---|
| Hyfl_J | 101 | GIACGESCAYFGCWIPGCSCRNKVCYFN |
| Hyfl_K | 102 | GTPCGESCVYIPCFTAVVGCTCKDKVCYLN |
| Hyfl_L | 103 | GTPCAESCVYLPCFTGVIGCTCKDKVCYLN |
| Hyfl_N_(partial) | 105 | CGETCVILPCISAALGCSCKDTVCYKN |
| Hyfl_O_(partial) | 106 | CGETCVIFPCISAAFGCSCKDTVCYKN |
| Hyfl_P | 107 | GSVPCGESCVWIPCISGIAGCSCKNKVCYLN |
| Hymo_A_(partial) | 108 | CGETCLFIPCIFSVVGCSCSSKVCYRN |
| Hymo_B_(partial) | 109 | CGETCVTGTCYTPGCACDWPVCKRD |
| Hyst_A_(partial) | 110 | CGETCIWGRCYSENIGCHCGFGICTLN |
| Hyve_A_(partial) | 111 | CGETCLFIPCLTSVFGCSCKNRGCYKI |
| Hyca_A_(partial) | 112 | CGETCVVDTRCYTKKCSCAWPVCMRN |
| Hyde_A_(partial) | 113 | CVWIPCISAAIGCSCKSKVCYRN |
| Hyen_A_(partial) | 114 | CGESCVYIPCTVTALLGCSCKDKVCYKN |
| Hyen_B_(partial) | 115 | CGETCKVTKRCSGQGCSCLKGRSCYD |
| Hyep_A_(partial) | 116 | CGETCVVLPCFIVPGCSCKSSVCYFN |
| Hyep_B_(partial) | 117 | CGETCIYIPCFTEAVGCKCKDKVCYKN |
| tricyclon_B | 118 | GGTIFDCGESCFLGTCYTKGCSCGEWKLCYGEN |
| kalata_B8 | 119 | GSVLNCGETCLLGTCYTTGCTCNKYRVCTKD |
| cycloviolacin_H4 | 120 | GIPCAESCVWIPCTVTALLGCSCSNNVCYN |
| cycloviolacin_O13 | 121 | GIPCGESCVWIPCISAAIGCSCKSKVCYRN |
| violacin_A | 122 | SAISCGETCFKFKCYTPRCSCSYPVCK |
| cycloviolacin_O14 | 123 | GSIPACGESCFKGKCYTPGCSCSKYPLCAKN |
| cycloviolacin_O15 | 124 | GLVPCGETCFTGKCYTPGCSCSYPICKKN |
| cycloviolacin_O16 | 125 | GLPCGETCFTGKCYTPGCSCSYPICKKIN |
| cycloviolacin_O17 | 126 | GIPCGESCVWIPCISAAIGCSCKNKVCYRN |
| cycloviolacin_O18 | 127 | GIPCGESCVYIPCTVTALAGCKCKSKVCYN |
| cycloviolacin_O19 | 128 | GTLPCGESCVWIPCISSVVGCSCKSKVCYKD |
| cycloviolacin_O20 | 129 | GIPCGESCVWIPCLTSAIGCSCKSKVCYRD |
| cycloviolacin_O21 | 130 | GLPVCGETCVTGSCYTPGCTCSWPVCTRN |
| cycloviolacin_O22 | 131 | GLPICGETCVGGTCNTPGCTCSWPVCTRN |
| cycloviolacin_O23 | 132 | GLPTCGETCFGGTCNTPGCTCDSSWPICTHN |
| cycloviolacin_O24 | 133 | GLPTCGETCFGGTCNTPGCTCDPWPVCTHN |
| cycloviolacin_O25 | 134 | DIFCGETCAFIPCITHVPGTCSCKSKVCYFN |
| [P20D,V21K]-kalata_B1 | 135 | GLPVCGETCVGGTCNTPGCTCSWDKCTRN |
| [W19K,_P20N,_V21K]-kalata_B1 | 136 | GLPVCGETCVGGTCNTPGCTCSKNKCTRN |
| [Glu(Me)]cyO2 | 137 | GIPCGXSCVWIPCISSAIGCSCKSKVCYRN |
| [Lys(Ac)]2cyO2 | 138 | GIPCGESCVWIPCISSAIGCSCKSXSVCYRN |
| [Arg(CHD)]cyO2 | 139 | GIPCGESCVWIPCISSAIGCSCKSKVCYXN |

TABLE 1-continued

| Parental Cyclotide | SEQ ID NO: | Cyclotide Backbone Sequence |
|---|---|---|
| ([Lys(Ac)]2[Arg(CHD)]) cyO2 | 140 | GIPCGESCVWIPCISSAIGCSCXSXVCYXN |
| kalata_B1_oia | 141 | GLPVCGETCVGGTCNTPGCTCSWPVCTRN |
| kalata_B1_nfk | 142 | GLPVCGETCVGGTCNTPGCTCSWPVCTRN |
| kalata_B2_nfk | 143 | GLPVCGETCFGGTCNTPGCSCTWPICTRD |
| kalata_B2_kyn | 144 | GLPVCGETCFGGTCNTPGCSCTWPICTRD |
| kalata_B9 | 145 | GSVFNCGETCVLGTCYTPGCTCNTYRVCTKD |
| kalata_B10 | 146 | GLPTCGETCFGGTCNTPGCSCSSWPICTRD |
| kalata_B10_oia | 147 | GLPTCGETCFGGTCNTPGCSCSSWPICTRD |
| kalata_B11 | 148 | GLPVCGETCFGGTCNTPGCSCTDPICTRD |
| kalata_B12 | 149 | GSLCGDTCFVLGCNDSSCSCNYPICVKD |
| kalata_B13 | 150 | GLPVCGETCFGGTCNTPGCACDPWPVCTRD |
| kalata_B14 | 151 | GLPVCGESCFGGTCNTPGCACDPWPVCTRD |
| kalata_B15 | 152 | GLPVCGESCFGGSCYTPGCSCTWPICTRD |
| kalata_B16 | 153 | GIPCAESCVYIPCTITALLGCKCQDKVCYD |
| kalata_B17 | 154 | GIPCAESCVYIPCTITALLGCKCKDQVCYN |
| Amrad_5 | 155 | CGETCVGGTCNTPGCTCSWPVCRRKRRR |
| Amrad_9 | 156 | CGETCRRKRRRCNTPGCTCSWPVCTRNGLPV |
| Amrad_11 | 157 | CGETCVGGTCNTRRKRRRGCTCSWPVCTRNGLPV |
| Amrad_17 | 158 | CGETCVGGTCNTPGCTCRRKRRRVCTRNGLPV |
| Amrad_7 | 159 | CGETCVGGTCNTPGCTCRRKRRRCTRNGLPV |
| Amrad_8 | 160 | CGETCVGGTCRRKRRRCTCSWPVCTRNGLPV |
| kalata_B18 | 161 | GVPCAESCVYIPCISTVLGCSCSNQVCYRN |
| PS-1 | 162 | GFIPCGETCIWDKTCHAAGCSCSVANICVRN |
| CD-1 | 163 | GADGFCGESCYVIPCISYLVGCSCDTIEKVCKRN |
| cycloviolacin_Y1 | 164 | GGTIFDCGETCFLGTCYTPGCSCGNYGFCYGTN |
| cycloviolacin_Y2 | 165 | GGTIFDCGESCFLGTCYTAGCSCGNWGLCYGTN |
| cycloviolacin_Y3 | 166 | GGTIFDCGETCFLGTCYTAGCSCGNWGLCYGTN |
| cycloviolacin_Y4 | 167 | GVPCGESCVFIPCITGVIGCSCSSNVCYLN |
| cycloviolacin_Y5 | 168 | GIPCAESCVWIPCTVTALVGCSCSDKVCYN |
| vibi_A | 169 | GLPVCGETCFGGTCNTPGCSCSYPICTRN |
| vibi_B | 170 | GLPVCGETCFGGTCNTPGCTCSYPICTRN |
| vibi_C | 171 | GLPVCGETCAFGSCYTPGCSCSWPVCTRN |
| vibi_D | 172 | GLPVCGETCFGGRCNTPGCTCSYPICTRN |
| vibi_E | 173 | GIPCAESCVWIPCTVTALIGCGCSNKVCYN |
| vibi_F | 174 | GTIPCGESCVFIPCLTSALGCSCKSKVCYKN |
| vibi_G | 175 | GTFPCGESCVFIPCLTSAIGCSCKSKVCYKN |
| vibi_H | 176 | GLLPCAESCVYIPCLTTVIGCSCKSKVCYKN |
| vibi_I | 177 | GIPCGESCVWIPCLTSTVGCSCKSKVCYRN |

TABLE 1-continued

| Parental Cyclotide | SEQ ID NO: | Cyclotide Backbone Sequence |
|---|---|---|
| vibi_J | 178 | GTFPCGESCVWIPCISKVIGCACKSKVCYKN |
| vibi_K | 179 | GIPCGESCVWIPCLTSAVGCPCKSKVCYRN |
| Viba_2 | 180 | GIPCGESCVYLPCFTAPLGCSCSSKVCYRN |
| Viba_5 | 181 | GIPCGESCVWIPCLTATIGCSCKSKVCYRN |
| Viba_10 | 182 | GIPCAESCVYLPCVTIVIGCSCKDKVCYN |
| Viba_12 | 183 | GIPCAESCVWIPCTVTALLGCSCKDKVCYN |
| Viba_14 | 184 | GRLCGERCVIERTRAWCRTVGCICSLHTLECVRN |
| Viba_17 | 185 | GLPVCGETCVGGTCNTPGCGCSWPVCTRN |
| Viba_15 | 186 | GLPVCGETCVGGTCNTPGCACSWPVCTRN |
| mram_1 | 187 | GSIPCGESCVYIPCISSLLGCSCKSKVCYKN |
| mram_2 | 188 | GIPCAESCVYIPCLTSAIGCSCKSKVCYRN |
| mram_3 | 189 | GIPCGESCVYLPCFTTIIGCKCQGKVCYH |
| mram_4 | 190 | GSIPCGESCVFIPCISSVVGCSCKNKVCYKN |
| mram_5 | 191 | GTIPCGESCVFIPCLTSAIGCSCKSKVCYKN |
| mram_6 | 192 | GSIPCGESCVYIPCISSLLGCSCESKVCYKN |
| mram_7 | 193 | GSIPCGESCVFIPCISSIVGCSCKSKVCYKN |
| mram_8 | 194 | GIPCGESCVFIPCLTSAIGCSCKSKVCYRN |
| mram_9 | 195 | GVPCGESCVWIPCLTSIVGCSCKNNVCTLN |
| mram_10 | 196 | GVIPCGESCVFIPCISSVLGCSCKNKVCYRN |
| mram_11 | 197 | GHPTCGETCLLGTCYTPGCTCKRPVCYKN |
| mram_12 | 198 | GSAILCGESCTLGECYTPGCTCSWPICTKN |
| mram_13 | 199 | GHPICGETCVGNKCYTPGCTCTWPVCYRN |
| mram_14 | 200 | GSIPCGEGCVFIPCISSIVGCSCKSKVCYKN |
| Viba_1 | 201 | GIPCGEGCVYLPCFTAPLGCSCSSKVCYRN |
| Viba_3 | 202 | GIPCGESCVWIPCLTAAIGCSCSSKVCYRN |
| Viba_4 | 203 | GVPCGESCVWIPCLTSAIGCSCKSSVCYRN |
| Viba_6 | 204 | GIPCGESCVLIPCISSVIGCSCKSKVCYRN |
| Viba_7 | 205 | GVIPCGESCVFIPCISSVIGCSCKSKVCYRN |
| Viba_8 | 206 | GAGCIETCYTFPCISEMINCSCKNSRCQKN |
| Viba_9 | 207 | GIPCGESCVWIPCISSAIGCSCKNKVCYRK |
| Viba_11 | 208 | GIPCGESCVWIPCISGAIGCSCKSKVCYRN |
| Viba_13 | 209 | TIPCAESCVWIPCTVTALLGCSCKDKVCYN |
| Viba_16 | 210 | GLPICGETCTLGTCYTVGCTCSWPICTRN |
| [G1A]kalata_B1 | 211 | ALPVCGETCVGGTCNTPGCTCSWPVCTRN |
| [L2A]kalata_B1 | 212 | GAPVCGETCVGGTCNTPGCTCSWPVCTRN |
| [P3A]kalata_B1 | 213 | GLAVCGETCVGGTCNTPGCTCSWPVCTRN |
| [V4A]kalata_B1 | 214 | GLPACGETCVGGTCNTPGCTCSWPVCTRN |
| [G6A]kalata_B1 | 215 | GLPVCAETCVGGTCNTPGCTCSWPVCTRN |

TABLE 1-continued

| Parental Cyclotide | SEQ ID NO: | Cyclotide Backbone Sequence |
|---|---|---|
| [E7A]kalata_B1 | 216 | GLPVCGATCVGGTCNTPGCTCSWPVCTRN |
| [T8A]kalata_B1 | 217 | GLPVCGEACVGGTCNTPGCTCSWPVCTRN |
| [V10A]kalata_B1 | 218 | GLPVCGETCAGGTCNTPGCTCSWPVCTRN |
| [G11A]kalata_B1 | 219 | GLPVCGETCVAGTCNTPGCTCSWPVCTRN |
| [G12A]kalata_B1 | 220 | GLPVCGETCVGATCNTPGCTCSWPVCTRN |
| [T13A]kalata_B1 | 221 | GLPVCGETCVGGACNTPGCTCSWPVCTRN |
| [N15A]kalata_B1 | 222 | GLPVCGETCVGGTCATPGCTCSWPVCTRN |
| [T16A]kalata_B1 | 223 | GLPVCGETCVGGTCNAPGCTCSWPVCTRN |
| [P17A]kalata_B1 | 224 | GLPVCGETCVGGTCNTAGCTCSWPVCTRN |
| [G18A]kalata_B1 | 225 | GLPVCGETCVGGTCNTPACTCSWPVCTRN |
| [T20A]kalata_B1 | 226 | GLPVCGETCVGGTCNTPGCACSWPVCTRN |
| [S22A]kalata_B1 | 227 | GLPVCGETCVGGTCNTPGCTCAWPVCTRN |
| [W23A]kalata_B1 | 228 | GLPVCGETCVGGTCNTPGCTCSAPVCTRN |
| [P24A]kalata_B1 | 229 | GLPVCGETCVGGTCNTPGCTCSWAVCTRN |
| [V25A]kalata_B1 | 230 | GLPVCGETCVGGTCNTPGCTCSWPACTRN |
| [T27A]kalata_B1 | 231 | GLPVCGETCVGGTCNTPGCTCSWPVCARN |
| [R28A]kalata_B1 | 232 | GLPVCGETCVGGTCNTPGCTCSWPVCTAN |
| [N29A]kalata_B1 | 233 | GLPVCGETCVGGTCNTPGCTCSWPVCTRA |
| Cter_A | 234 | GVIPCGESCVFIPCISTVIGCSCKNKVCYRN |
| Cter_B | 235 | GVPCAESCVWIPCTVTALLGCSCKDKVCYLN |
| hcf-1_variant | 236 | GIPCGESCHIPCVTSAIGCSCRNRSCMRN |
| Vpl-1 | 237 | GSQSCGESCVLIPCISGVIGCSCSSMICYFN |
| Vpf-1 | 238 | GIPCGESCVFIPCLTAAIGCSCRSKVCYRN |
| cO31 | 239 | GLPVCGETCVGGTCNTPGCSCSIPVCTRN |
| cO28 | 240 | GLPVCGETCVGGTCNTPGCSCSWPVCFRD |
| cO32 | 241 | GAPVCGETCFGGTCNTPGCTCDPWPVCTND |
| cO33 | 242 | GLPVCGETCVGGTCNTPYCTCSWPVCTRD |
| cO34 | 243 | GLPVCGETCVGGTCNTEYCTCSWPVCTRD |
| cO35 | 244 | GLPVCGETCVGGTCNTPYCFCSWPVCTRD |
| cO29 | 245 | GIPCGESCVWIPCISGAIGCSCKSKVCYKN |
| cO30 | 246 | GIPCGESCVWIPCISSAIGCSCKNKVCFKN |
| cO26 | 247 | GSIPACGESCFRGKCYTPGCSCSKYPLCAKD |
| cO27 | 248 | GSIPACGESCFKGWCYTPGCSCSKYPLCAKD |
| Globa_F | 249 | GSFPCGESCVFIPCISAIAGCSCKNKVCYKN |
| Globa_A | 250 | GIPCGESCVFIPCITAAIGCSCKTKVCYRN |
| Globa_B | 251 | GVIPCGESCVFIPCISAVLGCSCKSKVCYRN |
| Globa_D | 252 | GIPCGETCVFMPCISGPMGCSCKHMVCYRN |
| Globa_G | 253 | GVIPCGESCVFIPCISSVLGCSCKNKVCYRN |
| Globa_E | 254 | GSAFGCGETCVKGKCNTPGCVCSWPVCKKN |

TABLE 1-continued

| Parental Cyclotide | SEQ ID NO: | Cyclotide Backbone Sequence |
|---|---|---|
| Globa_C | 255 | APCGESCVFIPCISAVLGCSCKSKVCYRN |
| Glopa_D | 256 | GVPCGESCVWVPCTVTALMGCSCVREVCRKD |
| Glopa_E | 257 | GIPCAESCVWIPCTVTKMLGCSCKDKVCYN |
| Glopa_A | 258 | GGSIPCIETCVWTGCFLVPGCSCKSDKKCYLN |
| Glopa_B | 259 | GGSVPCIETCVWTGCFLVPGCSCKSDKKCYLN |
| Glopa_C | 260 | GDIPLCGETCFEGGNCRIPGCTCVWPFCSKN |
| Co36 | 261 | GLPTCGETCFGGTCNTPGCTCDPFPVCTHD |
| cycloviolacin_T1 | 262 | GIPVCGETCVGGTCNTPGCSCSWPVCTRN |
| cycloviolacin_T2 | 263 | GLPICGETCVGGTCNTPGCSCSWPVCTRN |
| psyle_A | 264 | GIACGESCVFLGCFIPGCSCKSKVCYFN |
| psyle_B | 265 | GIPCGETCVAFGCWIPGCSCKDKLCYYD |
| psyle_C | 266 | KLCGETCFKFKCYTPGCSCSYFPCK |
| psyle_D | 267 | GIPCGESCVFIPCTVTALLGCSCQNKVCYRD |
| psyle_E | 268 | GVIPCGESCVFIPCISSVLGCSCKNKVCYRD |
| psyle_F | 269 | GVIPCGESCVFIPCITAAVGCSCKNKVCYRD |
| vaby_A | 270 | GLPVCGETCAGGTCNTPGCSCSWPICTRN |
| vaby_B | 271 | GLPVCGETCAGGTCNTPGCSCTWPICTRN |
| vaby_C | 272 | GLPVCGETCAGGRCNTPGCSCSWPVCTRN |
| vaby_D | 273 | GLPVCGETCFGGTCNTPGCTCDPWPVCTRN |
| vaby_E | 274 | GLPVCGETCFGGTCNTPGCSCDPWPVCTRN |
| Oak6_cyclotide_2 | 275 | GLPICGETCFGGTCNTPGCICDPWPVCTRD |
| Oak7_cyclotide | 276 | GSHCGETCFFFGCYKPGCSCDELRQCYKN |
| Oak8_cyclotide | 277 | GVPCGESCVFIPCLTAVVGCSCSNKVCYLN |
| Oak6_cyclotide_1 | 278 | GLPVCGETCFGGTCNTPGCACDPWPVCTRN |
| Cter_C | 279 | GVPCAESCVWIPCTVTALLGCSCKDKVCYLD |
| Cter_D | 280 | GIPCAESCVWIPCTVTALLGCSCKDKVCYLN |
| Cter_E | 281 | GIPCAESCVWIPCTVTALLGCSCKDKVCYLD |
| Cter_F | 282 | GIPCGESCVFIPCISSVVGCSCKSKVCYLD |
| Cter_G | 283 | GLPCGESCVFIPCITTVVGCSCKNKVCYNN |
| Cter_H | 284 | GLPCGESCVFIPCITTVVGCSCKNKVCYND |
| Cter_I | 285 | GTVPCGESCVFIPCITGIAGCSCKNKVCYIN |
| Cter_J | 286 | GTVPCGESCVFIPCITGIAGCSCKNKVCYID |
| Cter_K | 287 | HEPCGESCVFIPCITTVVGCSCKNKVCYN |
| Cter_L | 288 | HEPCGESCVFIPCITTVVGCSCKNKVCYD |
| Cter_M | 289 | GLPTCGETCTLGTCYVPDCSCSWPICMKN |
| Cter_N | 290 | GSAFCGETCVLGTCYTPDCSCTALVCLKN |
| Cter_O | 291 | GIPCGESCVFIPCITGIAGCSCKSKVCYRN |
| Cter_P | 292 | GIPCGESCVFIPCITAAIGCSCKSKVCYRN |

TABLE 1-continued

| Parental Cyclotide | SEQ ID NO: | Cyclotide Backbone Sequence |
|---|---|---|
| Cter_Q | 293 | GIPCGESCVFIPCISTVIGCSCKNKVCYRN |
| Cter_R | 294 | GIPCGESCVFIPCTVTALLGCSCKDKVCYKN |
| yitri_B | 295 | GVPICGESCVGGTCNTPGCSCSWPVCTTN |
| yitri_C | 296 | GLPICGETCVGGTCNTPGCFCTWPVCTRN |
| yitri_D | 297 | GLPVCGETCFTGSCYTPGCSCNWPVCNRN |
| yitri_E | 298 | GLPVCGETCVGGTCNTPGCSCSWPVCFRN |
| yitri_F | 299 | GLTPCGESCVWIPCISSVVGCACKSKVCYKD |
| hedyotide_B1 | 300 | GTRCGETCFVLPCWSAKFGCYCQKGFCYRN |

In some embodiments, a peptide derived from, comprising, alternatively consisting essentially of, or yet further consisting of angiotensinogen (SEQ ID NO: 6; GenBank accession numbers: BC011519 (mRNA), AAH11519.1 (protein)) is grafted between the termini of the cyclotide backbone. In one embodiment, the peptide comprises or consists essentially of angiotensin I: DRVYIHPFHL (SEQ ID NO: 7) or an equivalent thereof. In another embodiment, the peptide comprises or consists essentially of angiotensin II: DRVYIHPF (SEQ ID NO: 8) or an equivalent thereof. In another embodiment, the peptide comprises or consists essentially of angiotensin III: RVYIHPF (SEQ ID NO: 9) or an equivalent thereof. In another embodiment, the peptide comprises or consists essentially of angiotensin IV: VYIHPF (SEQ ID NO: 10) or an equivalent thereof. In another embodiment, the peptide comprises or consists essentially of angiotensin (1-7) (AT1-7): DRVYIHP (SEQ ID NO: 11) or an equivalent thereof. Nonlimiting examples of equivalents of AT1-7 include DRVYIP (SEQ ID NO: 12), XRVYIE (SEQ ID NO: 13), and XRVYIHE (SEQ ID NO: 14). In another embodiment, the peptide comprises or consists essentially of angiotensin-(1-5) (AT1-5): DRVYI (SEQ ID NO: 15) or an equivalent thereof. In another embodiment, the peptide comprises or consists essentially of angiotensin (1-4) (AT1-5): DRVY (SEQ ID NO: 16) or an equivalent thereof. As used herein, the phrase "grafted between" in this context means that the AT1-7 peptide is covalently attached to the carboxy and amino termini of the cyclotide backbone. In one aspect, residue X in the above sequences represents L-2,3-diaminopropionic acid (L-Dap). In other aspects, residue X represents one or more unnatural amino acids.

In one embodiment, the cyclotide incorporates one or more unnatural amino acids. "Unnatural amino acids" are non-proteinogenic amino acids that either occur naturally or are chemically synthesized. While unnatural amino acids are not on the standard 20-amino acid list, they can be incorporated into a protein sequence. Non-limiting examples of unnatural amino acids include L-2,3-diaminopropionic acid, DL-2,3-diaminopropionic acid, 2,4-diaminobutyric acid, p-methyxyphenylalanine, p-azidophenylalanine, L-(7-hydroxycoumarin-4-yl)ethylglycine, acetyl-2-naphthyl alanine, 2-naphthyl alanine, 3-pyridyl alanine, 4-chloro phenyl alanine, alloisoleucine, Z-alloisoleucine dcha salt, allothreonine, 4-Iodo-phenylalanine, L-benzothienyl-D-alanine OH.

In some aspects, the cyclotide comprises at least an unnatural amino acid residue but retains six cysteine residues that form three disulfide bonds in a cyclized cyclotide. In one aspect, the unnatural amino acid comprises one or more selected from L-2,3-diaminopropionic acid (L-Dap), p-methyxyphenylalanine, p-azidophenylalanine or L-(7-hydroxycoumarin-4-yl)ethylglycine.

In one aspect, the amino acid sequence of the cyclotide with the grafted AT1-7 peptide comprises or consists essentially of

```
                                    (MCo-AT 1-7, SEQ ID NO: 17)
GGVCPKILQRCRRDSDCPGACICRGNGYCGSGDRVYIHP
``` or an equivalent thereof. In another aspect, the amino acid sequence of the cyclotide with the grafted AT1-7 peptide comprises or consists essentially of GGVCPKILQRCRRDSDCPGACICRGNGYCGSGDRVYIP (MCo-AT1-7, SEQ ID NO: 18) or an equivalent thereof. In one aspect the amino acid sequence of the cyclotide with the grafted AT1-7 peptide comprises or consists essentially of GGVCPKILQRCRRDSDCPGACICRGNGYCGSGXRVYIE (MCo-AT1-7, SEQ ID NO: 19) or an equivalent thereof. In one aspect, the amino acid sequence of the cyclotide with the grafted AT1-7 peptide comprises or consists essentially of

```
                                     (MCo-AT1-7, SEQ ID NO: 20)
GGVCPKILQRCRRDSDCPGACICRGNGYCGSGXRVYIHE
``` or an equivalent thereof. In one aspect, residue X in the above sequences represents L-2,3-diaminopropionic acid (L-Dap). In other aspects, residue X represents one or more unnatural amino acids. In further aspect, residue B in the above sequences represents asparagine or aspartic acid.

In a further aspect, the cyclotides, peptides, and polypeptides of the present disclosure further comprise, or alternatively consist essentially of, or yet further consist of one or more labels or purification markers. In some aspects, the label is detectable and comprises one or more of a fluorescent label, a phosphorescent label, an enzymatic label, a chemical label, or a radiolabel. In some aspects, the label comprises a radiolabel such as $^{32}P$, $^{35}P$, $^{35}S$, or $^{125}I$. In other aspects, the label comprises a biotin label, a digoxigenin label, an alkaline phosphatase label, a horse radish peroxidase label, or a fluorescent moiety. In other aspects, the cyclotides, peptides and polypeptides of the present disclosure further comprise, or alternatively consist essentially of, or yet further consist of a purification marker such as an epitope tag (e.g. a histidine tag, FLAG tag, Myc tag, or V5 tag). In a yet further aspect the cyclotides, peptides, and polypeptides of the present disclosure further comprise, or alternatively consist essentially of, or yet further consist of, a carrier, such as a pharmaceutically acceptable carrier.

Further provided is a plurality of cyclotides as described herein, wherein the amino acid sequences of the plurality are the same or different from each other, that are optionally labeled or comprise a purification marker. In a further aspect, the cyclotide or plurality of cyclotides further comprises a pharmaceutically acceptable carrier. The cyclotide or plurality thereof can be combined with a therapeutic agent.

In another aspect, this disclosure provides an isolated polynucleotide encoding one or more of the isolated peptides and/or cyclotides described above, alone or in a replication or expression vector, e.g., a viral vector or a plasmid. The polynucleotide units further contain the necessary regulatory element operatively linked to the coding sequences for expression of the polynucleotide in a host cell. Thus, this disclosure also provides an isolated host cell comprising the recombinant peptide as described above or the recombinant polynucleotide, or vector containing same, also as described above. The isolated host cell is a prokaryotic or a eukaryotic cell. In one particular aspect, the host cell is an *E. coli* cell. The polynucleotides or peptide can also be chemically synthesized using methods known in the art and described herein.

Further provided is a method for recombinantly producing the peptides of this disclosure by growing an isolated host cell as described above under conditions that favor the expression of the polynucleotide. In one aspect, the peptides are isolated from the host cells. The peptides and polynucleotide can also be chemically synthesized.

"Host cell" refers not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Examples of such include, eukaryotic cells and prokaryotic cells such as *E. coli* cells. Examples of eukaryotic cells are provided herein and include, but are not limited to cells from plants, fungi, and animals, e.g., murines, rats, rabbit, simians, bovines, ovine, porcine, canines, feline, farm animals, sport animals, pets, equine, and primate, particularly human. In some aspects, the host cell is a yeast cell such as *Saccharomyces cerevisiae*. The cells can be cultured cells or they can be primary cells. Cultured cell lines can be purchased from vendors such as the American Type Culture Collection (ATCC), U.S.A.

In a further aspect, the polynucleotides, vectors and/or host cells further comprise a label. In a yet further aspect the polynucleotides, vectors and/or host cells further comprise, or alternatively consist essentially of, or yet further consists of, a carrier, such as a pharmaceutically acceptable carrier.

Compositions

Compositions are further provided. The compositions comprise a carrier and one or more of an isolated polynucleotide of the disclosure, an isolated polypeptide of the disclosure, an antibody, a gene delivery vehicle of the disclosure or an isolated host cell of the disclosure. The carriers can be one or more of a solid support or a pharmaceutically acceptable carrier. The compositions can further comprise an adjuvant or other components suitable for administrations as vaccines. In one aspect, the compositions are formulated with one or more pharmaceutically acceptable excipients, diluents, carriers and/or adjuvants. In addition, embodiments of the compositions of the present disclosure include one or more of an isolated polypeptide of the disclosure, an isolated polynucleotide of the disclosure, a vector of the disclosure, an isolated host cell of the disclosure, or an antibody of the disclosure, formulated with one or more pharmaceutically acceptable auxiliary substances.

Pharmaceutical formulations and unit dose forms suitable for oral administration are particularly useful in the treatment of chronic conditions, infections, and therapies in which the patient self-administers the drug. In one aspect, the formulation is specific for pediatric administration.

The disclosure provides pharmaceutical formulations in which the one or more of an isolated peptide of the disclosure, an isolated polynucleotide of the disclosure, a vector of the disclosure, an isolated host cell of the disclosure, can be formulated into preparations for administration in accordance with the disclosure by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives or other anticancer agents. For intravenous administration, suitable carriers include physiological saline, or phosphate buffered saline (PBS). In all cases, a composition for parenteral administration must be sterile and should be fluid to the extent that easy syringeability exists.

Aerosol formulations provided by the disclosure can be administered via inhalation and can be propellant or non-propellant based. For example, embodiments of the pharmaceutical formulations of the disclosure comprise a peptide of the disclosure formulated into pressurized acceptable propellants such as dichlorodifluoromethane, propane, nitrogen and the like. For administration by inhalation, the compounds can be delivered in the form of an aerosol spray from a pressurized container or dispenser which contains a suitable propellant, e.g., a gas such as carbon dioxide, or a nebulizer. A non-limiting example of a non-propellant is a pump spray that is ejected from a closed container by means of mechanical force (i.e., pushing down a piston with one's finger or by compression of the container, such as by a compressive force applied to the container wall or an elastic force exerted by the wall itself (e.g. by an elastic bladder)).

Suppositories of the disclosure can be prepared by mixing a compound of the disclosure with any of a variety of bases such as emulsifying bases or water-soluble bases. Embodiments of this pharmaceutical formulation of a compound of the disclosure can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compounds of the disclosure. Similarly, unit dosage forms for injection or intravenous administration may comprise a compound of the disclosure in a composition as a solution in sterile water, normal saline or another pharmaceutically acceptable carrier.

Embodiments of the pharmaceutical formulations of the disclosure include those in which one or more of an isolated polypeptide of the disclosure, an isolated polynucleotide of the disclosure, a vector of the disclosure, an isolated host cell of the disclosure, or an antibody of the disclosure is formulated in an injectable composition. Injectable pharmaceutical formulations of the disclosure are prepared as liquid solutions or suspensions; or as solid forms suitable for solution in, or suspension in, liquid vehicles prior to injection. The preparation may also be emulsified or the active ingredient encapsulated in liposome vehicles in accordance with other embodiments of the pharmaceutical formulations of the disclosure.

In an embodiment, one or more of an isolated polypeptide of the disclosure, an isolated polynucleotide of the disclosure, a gene delivery vehicle or vector of the disclosure, or an isolated host cell of the disclosure is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of a compound of the disclosure can be accomplished using any of a variety of refillable, pump systems. Pumps provide consistent, controlled release over time. In some embodiments, a compound of the disclosure is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT Publication No. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like. A further exemplary device that can be adapted for the present disclosure is the Synchromed infusion pump (Medtronic).

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

Suitable excipient vehicles for a peptide of the disclosure are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Compositions of the present disclosure include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. After administration, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the peptide (as well as combination compositions) is delivered in a controlled release system. For example, a peptide of the disclosure may be administered using intravenous infusion, an implantable osmotic pump, a transdermal patch, liposomes, or other modes of administration. In one embodiment, a pump may be used (Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials are used. In yet another embodiment a controlled release system is placed in proximity of the therapeutic target, i.e., the liver, thus requiring only a fraction of the systemic dose.

In another embodiment, the compositions of the present disclosure (as well as combination compositions separately or together) include those formed by impregnation of a peptide described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

The cyclotides of this disclosure are useful in a variety of in vitro and in vivo methods. In one aspect, the cyclotide is administered to a subject in need thereof for the treatment of lung cancer, breast cancer, and other cancers or tumors that express MAS1. The cyclotides also can be used for vasodilation, anti-proliferative properties and anti-angiogenic properties. The cyclotides also are able to reduce serum-stimulated growth of human lung cancer cells both in vitro and in vivo through activation of the unique AT1-7 receptor, MAS1. Thus, another aspect, the cyclotides are useful to activate MAS1 in vitro and in vivo.

The disclosed above methods comprising contacting the cell or tissue with an effective amount of one or more of: the cyclotide as described herein, the isolated polynucleotide described herein or the host cell described herein. The activation of the MAS1, vasodilation, anti-proliferation of cells, and anti-angiogenic properties, and reduction of the growth of lung cancer cells or tumors can be detected by methods known in the art and described herein. The activation of downstream targets of AT1-7 receptor may also be tested to determine the activation of MAS1. The contacting of the cell or tissue may be in vitro in tissue culture or in vivo in a subject.

A further method aspect relates to a method for reducing or inhibiting metastasis, angiogenesis, treating myocardial infarction and/or inhibiting tumor growth in a subject in need thereof comprising administering an effective amount of one or more of: the polypeptide as described herein, the isolated cyclotide, the polynucleotide described herein or the host cell as described herein to the subject. Inhibition or metastasis, angiogenesis, and tumor growth may be demonstrated by assays known in the art. For example, the inhibition may be demonstrated by the reduction of pro-angiogenic or pro-metastatic markers, the increase in anti-angiogenic or anti-metastatic factors, the reduction in tumor size, or the lack of new tumor growth.

Also provided is a method for promoting tumor cell death, e.g., lung or breast tumor death, in an animal, e.g., mammal in need thereof comprising administering an effective amount of one or more of: the polypeptide as described herein, the isolated polynucleotide described herein or the host cell described herein to the subject. Cell death of a tumor can be measured by a reduction in tumor growth or an increase in markers for cell death, necrosis, or apoptosis.

The compositions can be administered to an animal or mammal by a treating veterinarian or to a human patient by a treating physician.

Having described the general concepts of this invention, the following illustrative examples are provided.

Experimental Examples

In order to produce a novel cyclotide with MAS1 agonistic activity, the cyclotide MCoTI-I was used as molecular cyclotide backbone or scaffold (FIG. 1). MCoTI-cyclotides are found in the dormant seeds of the plant *Momordica cochinchinensis*, and are potent trypsin inhibitors (Ki about 25 pM). Natively folded MCoTI-cyclotides can be easily produced by standard recombinant methods as well as by chemical synthesis, and can also be easily engineered to incorporate novel biological functions. In addition, MCoTI-cyclotides show very little toxicity to human cells (IC50>100 µM) and therefore represent a desirable molecular scaffold for engineering new compounds with unique biological properties.

To engineer the cyclotide MCoTI-I to have AT1-7 activity, a derivative of the peptide AT1-7 peptide was grafted onto the cyclotide scaffold using loop 6 (FIG. 1). This loop has been shown previously to be more disordered in solution [9] and amenable to sequence variation. The peptide was grafted using the side-chains of residues 1 and 7. For this purpose the original residues at Asp1 and Pro7 in the AT1-7 peptide were replaced by diaminopropionic acid and glutamic acid, respectively. These positions have been shown to tolerate mutations in angiotensin-peptides without affecting their biological activity. For example Asp1 and Pro7 have been replaced by glutamine and cysteine without negatively affecting the biological activity of the corresponding angiotensin-derived peptides. The AT1-7 derived peptide was grafted into the cyclotide backbone between residues Gly1 and Ser32 using the β-amino and γ-carboxylic groups through the creation of two isopeptide bonds (FIG. 1). This allowed keeping the native positive and negative charged groups at the N- and C-terminal of the grafted AT1-7 derivative. The resulting grafted cyclotide was called MCo-AT1-7 (FIG. 1).

Figure 2B:
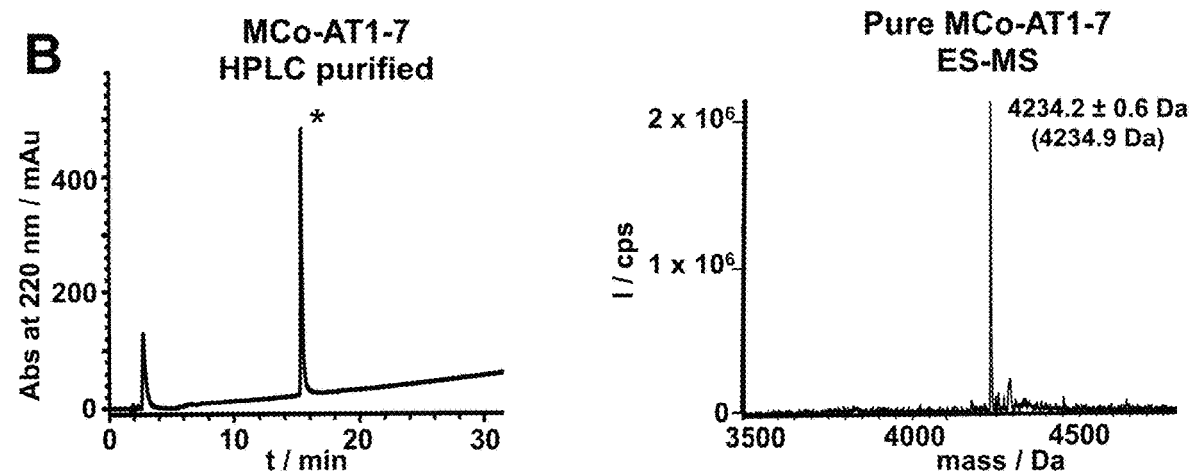
Figure 3:
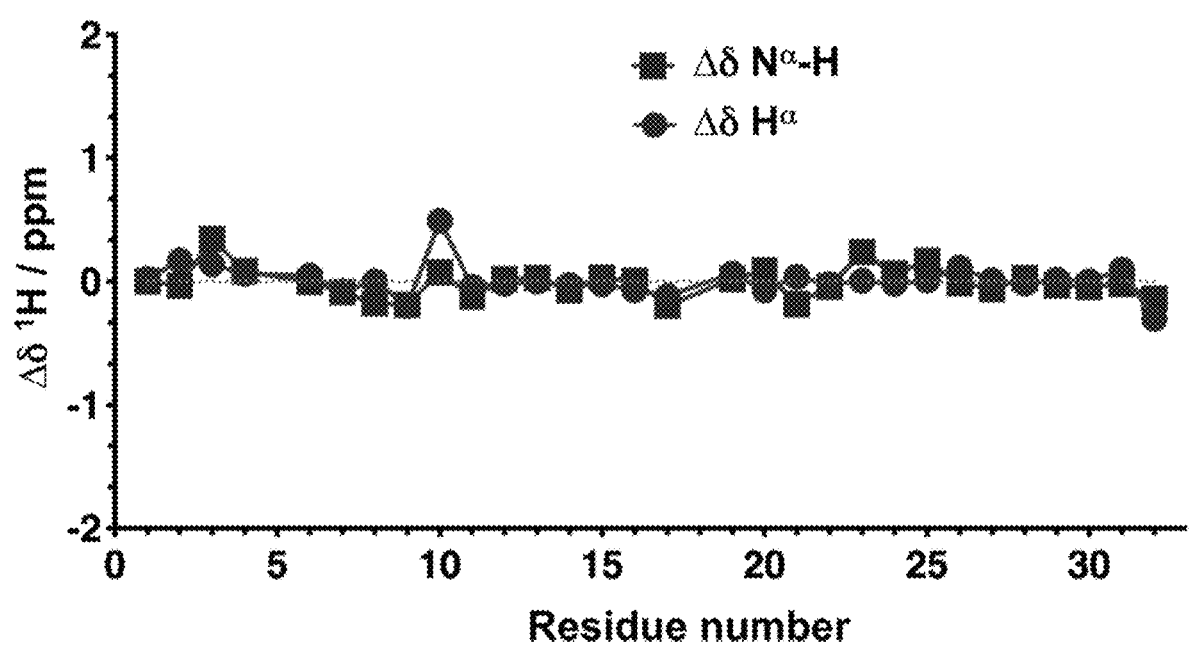
FIG. 3 shows proton nuclear magnetic resonance (1H-NMR) characterization of folded cyclotide MCo-AT1-7. Chemical shifts differences of the backbone, Nα-H and Hα protons between the common sequence (residues 1 through 32) of MCoTI-I and MCo-AT1-7.

Cyclotide MCo-AT1-7 was chemically synthesized using Fmoc-based solid-phase peptide synthesis on a sulfonamide resin. Activation of the sulfonamide linker with iodoacetonitrile, followed by cleavage with ethyl mercaptoacetate and acidolytic deprotection, provided the fully deprotected linear peptide α-thioester (FIG. 2A). The corresponding peptide thioester precursor was efficiently cyclized and folded in a one-pot reaction using sodium phosphate buffer at pH 7.2 in the presence of 1 mM GSH. The cyclization/folding reaction was complete in 24 h (FIG. 2A). The cyclization/folding yields was estimated by HPLC to be about 35% (FIG. 2A). Folded MCo-AT1-7 was purified by reverse-phase HPLC and characterized by ES-MS confirming ≥95% purity (FIG. 2B). Cyclotide MCo-AT1-7 was also characterized by 1H-NMR indicating that adopts a native cyclotide fold (FIG. 3, and FIGS. 8A-8B, and Table 2).

TABLE 2

Tabulation of chemical shifts of backbone amide protons (δ$^1$H-Nα and δ$^1$Hα) protons of MCo-AT1-7 and their respective differences from cyclotide MCoTI-I.

| Residue* | δ $^1$H-Nα (ppm) | δ $^1$Hα (ppm) | Δδ $^1$H-Nα (ppm) | Δδ $^1$Hα (ppm) |
|---|---|---|---|---|
| G1 | 8.112 | 3.988 | 0.001 | 0.021 |
| G2 | 8.008 | 4.002 | −0.034 | 0.169 |
| V3 | 8.73 | 4.013 | 0.346 | 0.138 |
| C4 | 8.665 | 5.13 | 0.083 | 0.064 |
| P5 | N/A | — | N/A | — |
| K6 | 8.138 | 4.177 | −0.004 | 0.046 |
| I7 | 7.541 | 4.177 | −0.085 | −0.081 |
| L8 | 8.412 | 4.411 | −0.177 | 0 |
| Q9 | 8.602 | 4.267 | −0.187 | −0.195 |
| R10 | 8.601 | 4.689 | 0.075 | 0.491** |
| C11 | 8.185 | 4.71 | −0.12 | −0.043 |
| R12 | 9.289 | 4.303 | 0.018 | −0.019 |
| R13 | 7.987 | 4.645 | 0.028 | 0 |
| D14 | 9.065 | 3.956 | −0.071 | −0.029 |

TABLE 2-continued

Tabulation of chemical shifts of backbone amide protons ($\delta^1$H-N$\alpha$ and $\delta^1$H$\alpha$) protons of MCo-AT1-7 and their respective differences from cyclotide MCoTI-I.

| Residue* | $\delta^1$H-N$\alpha$ (ppm) | $\delta^1$H$\alpha$ (ppm) | $\Delta\delta^1$H-N$\alpha$ (ppm) | $\Delta\delta^1$H$\alpha$ (ppm) |
|---|---|---|---|---|
| S15 | 8.088 | 4.15 | 0.03 | −0.021 |
| D16 | 7.642 | 4.436 | 0.006 | −0.07 |
| C17 | 7.815 | 4.807 | −0.194 | −0.116 |
| P18 | N/A | — | N/A | — |
| G19 | 8.414 | 3.685 | 0.022 | 0.063 |
| A20 | 8.412 | 4.314 | 0.089 | −0.071 |
| C21 | 7.994 | 4.478 | −0.184 | 0.036 |
| I22 | 8.899 | 4.289 | −0.042 | −0.021 |
| C23 | 9.275 | 4.828 | 0.237 | 0.005 |
| R24 | 8.013 | 4.171 | 0.064 | −0.018 |
| G25 | 8.975 | 3.813 | 0.165 | 0.011 |
| N26 | 7.685 | 4.693 | −0.014 | 0.113 |
| G27 | 8.261 | 3.869 | −0.061 | 0.01 |
| Y28 | 7.202 | 5.127 | 0.028 | −0.017 |
| C29 | 8.668 | 5.29 | −0.033 | 0.015 |
| S30 | 9.685 | 3.842 | −0.043 | 0 |
| S31 | 8.672 | 4.468 | −0.02 | 0.095 |
| G32 | 8.9 | 4.008 | −0.141 | −0.302 |

*Sequence numbers are based on McoTI-I.
**A rather large chemical shift difference (~0.5 ppm) of R10 alpha proton between MCo-AT1-7 and MCoTI-I is possibly induced by the concomitant changes in C11-C23 disulfide bridge related to grafting.

Figure 4:
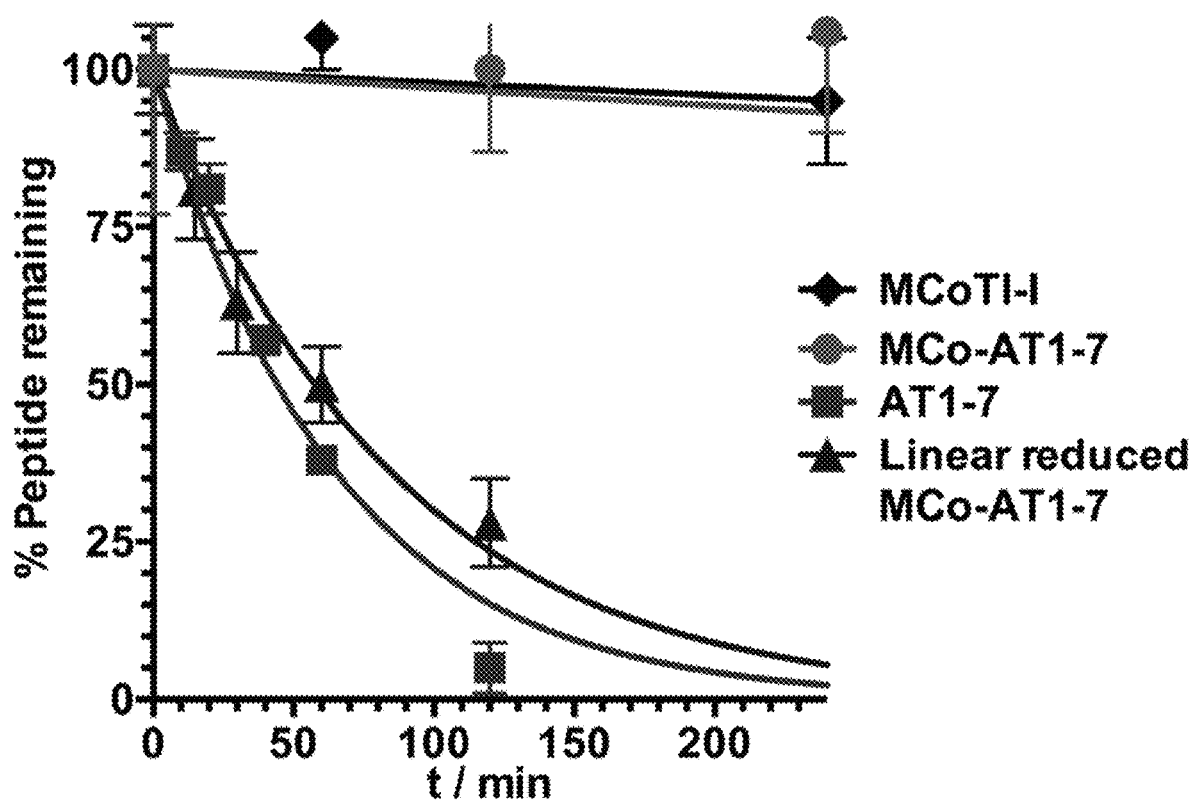
FIG. 4 shows stability of cyclotides MCo-AT1-7 and MCoTI-I, and peptide AT1-7 and reduced linear MCo-AT1-7 precursor to human serum at 37° C. Undigested peptides were quantified by HPLC-MS/MS.

The biological stability of cyclotide MCo-AT1-7 was compared to that of the empty scaffold (MCoTI-I) and the peptide AT1-7 (FIG. 4). This was accomplished by incubating the corresponding peptides in human serum at 37° C. The quantitative analysis of undigested polypeptides was performed using liquid chromatography coupled with tandem mass spectrometry (LC-MS/MS). Naturally occurring MCoTI-cyclotides present a very rigid structure, which makes them extremely stable to proteolytic degradation. Remarkably, cyclotide MCo-AT1-7 was only slightly less stable ($\tau_{1/2}$=39±5 h) than the parent cyclotide MCoTI-I ($\tau_{1/2}$=55±7 h) (FIGS. 4 and 7). In contrast, peptide AT1-7 was degraded considerably faster under the same conditions ($\tau_{1/2}$=44±3 min) (FIGS. 4 and 7). A linearized, reduced and alkylated version of MCo-AT1-7 (FIG. 6) was also rapidly degraded ($\tau_{1/2}$=57±5 min) (FIGS. 4 and 7) indicating the importance of the circular Cys-knot topology for proteolytic stability.

Figure 5:
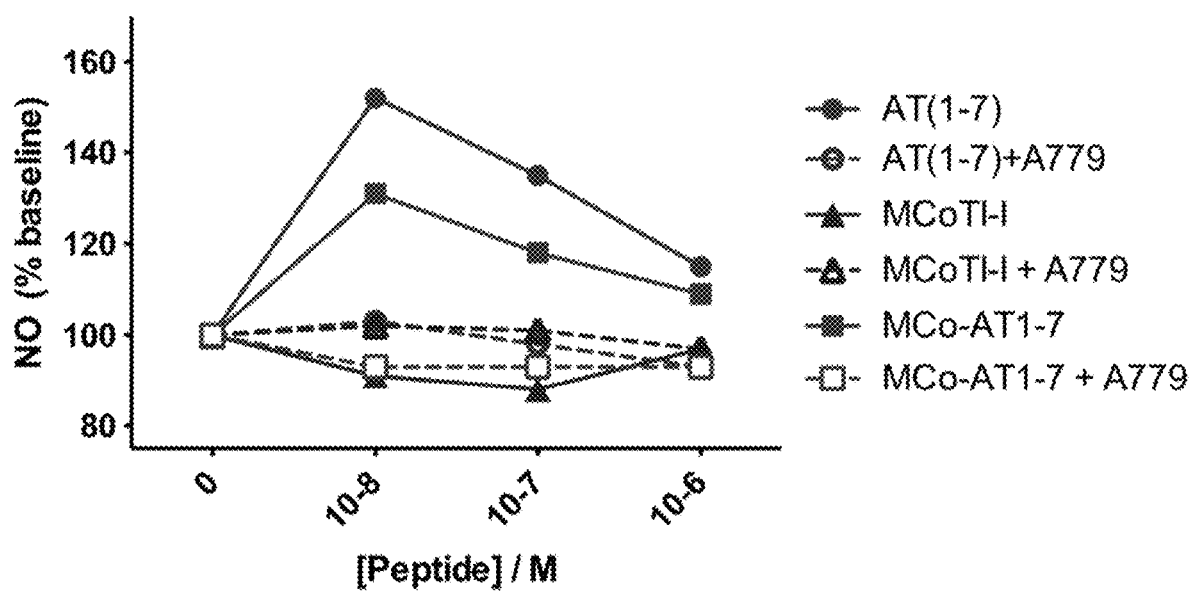
FIG. 5 shows biological activity of cyclotide MCo-AT1-7. MAS1 stably transfected CHO cells were tested using different concentrations of cyclotide MCo-AT1-7 and peptide AT1-7 in the absence or presence of MAS1 antagonist A779. The amount of intracellular NO was measured by fluorescence as described in the experimental section. Cyclotide MCoTI-I was used as negative control. The average of standard deviation of three experiments is shown.

Next, the ability of cyclotide MCo-AT1-7 to activate the MAS1 receptor was tested using CHO cells stably transfected with pTEJ-8 vector expressing recombinant human MAS1 in a cell-based fluorescence assay to detect the amount of NO release (FIG. 5). Cyclotide MCo-AT1-7 and peptide AT1-7 (used as positive control) were able to increase the intracellular concentration of NO in a dose dependent manner as measured by the level of fluorescence. The naturally-occurring cyclotide MCoTI-I did not show any increase in intracellular NO levels (FIG. 5). When the MAS1 activation biological assay was performed in the presence of the MAS1 peptide antagonist A779, no increase in the intracellular concentration of NO was detected therefore confirming the agonistic activity of the cyclotide MCo-AT1-7. A similar profile was obtained with the peptide AT1-7 (FIG. 5). The activity of the cyclotide MCo-AT1-7 was estimated to be about 90% of that of peptide AT1-7 at 10 nM in this assay.

In summary report here for the first time the design and synthesis of a novel cyclotide able to efficiently activate the MAS1 receptor. This was successfully accomplished by grafting an AT1-7-derived peptide onto loop 6 of the cyclotide MCoTI-I using the side-chains of the first and last residues of the grafted peptide through the formation of isopeptide bonds (FIG. 1). 1H-NMR studies also revealed that the grafting of the AT1-7-derived peptide using isopeptide bonds onto this loop did not affect the native cyclotide scaffold, indicating the tolerance of this loop for the grafting of peptide sequences using non-native peptide bonds. Cyclotide MCo-AT1-7 showed itself to be a potent MAS1 agonist, with similar activity to that of the peptide AT1-7. In addition, cyclotide MCo-AT1-7 showed a remarkable resistance to biological degradation in human serum, with a $\tau_{1/2}$ value of about 39 h. This value is similar to that of the cyclotide MCoTI-I and significantly higher that the half-life of the AT1-7 peptide ($\tau_{1/2}$ about 1 h).

These results show that engineered cyclotides hold great promise for the development of a novel type of peptide-based therapeutic able to efficiently target extracellular protein/protein interactions. The results demonstrate for the first time the design of an engineered cyclotide using isopeptide peptide bonds able to activate the MAS1 receptor with low nanomolar activity and very high serum stability, thereby providing a promising lead compound for the design of novel therapeutics for the treatment of cancer and myocardial infarction.

Materials and Methods

All chemicals involved in synthesis or analysis were obtained from Aldrich (Milwaukee, Wis.) or Novabiochem (San Diego, Calif.) unless otherwise indicated. Analytical HPLC was performed on a HP 1100 series instrument with 220 and 280 nm detection using a Vydac C18 column (5 micron, 4.6×150 mm) at a flow rate of 1 mL/min. Preparative and semipreparative HPLC were performed on a Waters Delta Prep system fitted with a Waters 2487 UV-visible detector using either a Vydac C18 column (15-20 µm, 50×250 mm) or a Vydac C18 (15-20 µm, 10×250 mm) at a flow rate of 50 or 5 mL/min, respectively. All runs used linear gradients of 0.1% aqueous trifluoroacetic acid (TFA) (solvent A) vs. 0.1% TFA, 90% acetonitrile in H2O (solvent B). Ultraviolet-visible (UV-vis) spectroscopy was carried out on an Agilent 8453 diode array spectrophotometer. Electrospray mass spectrometry (ES-MS) analysis was routinely applied to all compounds and components of reaction mixtures. ES-MS was performed on an Applied Biosystems API 3000 triple quadrupole electrospray mass spectrometer using Analyst 1.4.2. Calculated masses were obtained using Analyst 1.4.2.

Preparation of Fmoc-Tyr(tBu)-F

For all peptides synthesis, Fmoc-Tyr(tBu)-F was prepared using dimethylaminosulfur trifluoride (DAST) and immediately loaded to resin as described in Kluskens et al. J Pharmacolol Exp Ther 2009, 328, 849-854, incorporated herein by reference. Briefly, DAST (160 µL, 1.2 mmol) was added drop wise at 25° C. under nitrogen current to a stirred solution of Fmoc-Tyr(tBu)-OH (459.6 mg, 1 mmol) in 10 mL of dry dichloromethane (DCM), containing dry pyridine (81 µL, 1 mmol). After 20 minutes, the mixture was washed with ice-cold water (3×20 mL). The organic layer was separated and dried over anhydrous MgSO4. The solvent was removed under reduced pressure to give the corresponding Fmoc-amino acyl fluoride as yellowish oil that was immediately used.

Loading of 4-sulfamylbutyryl AM Resin with Fmoc-Tyr(tBu)-F

Loading of the first residue for all peptides was accomplished using Fmoc-Tyr(tBu)-F according to standard protocols (e.g. Contreras et al. J. Control. Release 2011, 155, 134-143). Briefly, 4-Sulfamylbutyryl AM resin (420 mg, 0.33 mmol) (Novabiochem) was swollen for 30 minutes with dry DCM and then drained. A solution of Fmoc-Tyr (tBu)-F (about 461 mg, 1 mmol) in dry DCM (2 mL) and di-isopropylethylamine (DIEA) (180 µL, 1 mmol) was added to the drained resin and reacted at 25° C. for 1 h. The resin was washed with dry DCM (5×5 mL), dried and kept at −20° C. until use.

Chemical Synthesis of Cyclotide MCo-AT1-7

Solid-phase synthesis of cyclotide MCo-AT1-7 was carried out on an automatic peptide synthesizer ABI433A (Applied Biosystems) using the Fast-Fmoc chemistry with 2-(1H-benzotriazol-1-yl)-1,1,3,3-tetramethyluronium hexafluorophosphate (HBTU)/diisopropylethylamine (DIEA) activation protocol at 0.1 mmole scale on a Fmoc-Tyr(tBu)-sulfamylbutyryl AM resin. Side-chain protection compatible with Fmoc-chemistry was employed as previously described for the synthesis of peptide a-thiesters by the Fmoc-protocol (see, e.g. Cavanagh et al. J. Magn. Res. 1992, 96, 670-678), except for the N-terminal Cys residue, which was introduced as Boc-Cys(Trt)-OH. Following chain assembly, the alkylation, thiolytic cleavage and side chain deprotection were performed as described in Contreras et al. J. Control. Release 2011, 155, 134-143. Briefly, about 100 mg of protected peptide resin were first alkylated two times with ICH2CN (174 µL, 2.4 mmol; previously filtered through basic alumina) and DIEA (82 µL, 0.46 mmol) in N-methylpyrrolidone (NMP) (2.2 mL) for 24 hours. The resin was then washed with NMP (3×5 mL) and DCM (3×5 mL). The alkylated peptide resin was cleaved from the resin with HSCH2CO2Et (200 µL, 1.8 mmol) in the presence of a catalytic amount of sodium thiophenolate (NaSPh, 3 mg, 22 µmol) in dimethylformamide (DMF):DCM (1:2 v/v, 1.2 mL) for 24 hours. The resin was then dried at reduced pressure. The sidechain protecting groups were removed by treating the dried resin with trifluoroacetic acid (TFA):H2O:triisopropylsilane (TIS) (95:3:2 v/v, 10 mL) for 3-4 h at room temperature. The resin was filtered and the linear peptide thioester was precipitated in cold Et2O. The crude material was dissolved in the minimal amount of H2O:MeCN (4:1) containing 0.1% TFA and characterized by HPLC and ES-MS [Expected mass: 4361.1 Da. Observed mass: 4360.0±0.7 Da] as the desired grafted MCoTI-I linear precursor α-thioester (FIG. 2). Cyclization and folding was accomplished by flash dilution of the linear α-thioester TFA crude to a final concentration of about 50 µM into freshly degassed 1 mM reduced glutathione (GSH), 0.1 M sodium phosphate buffer at pH 7.2 for 24 h (FIG. 2). The folded cyclotide was purified by semi-preparative HPLC using a linear gradient of 17-28% solvent B over 30 min. The purified cyclotide was characterized by HPLC and ES-MS confirming ≥95% purity (FIG. 2).

Chemical Synthesis of Linearized and S-Alkylated Cyclotide MCo-AT1-7

For the preparation of linearized and S-alkylated MCo-AT1-7, 20 mg of sulfonamide peptideresin was activated as described above and cleaved from the resin with propylamine in DMF (1:1, 0.8 mL) for 4 h. The resulting peptide was side deprotected and peptide collected by precipitation with diethyl ether as described above. The linear peptide was fully reduced with dithiothretol (40 mM, 300 µL) in freshly degassed 0.1 M Na2HPO4 buffer at pH 7.5 at 37° C. for 1 h followed by alkylation of all free cysteines with iodoacetamide (0.5 M, 200 µL) for 10 min at room temperature.

Figure 6:
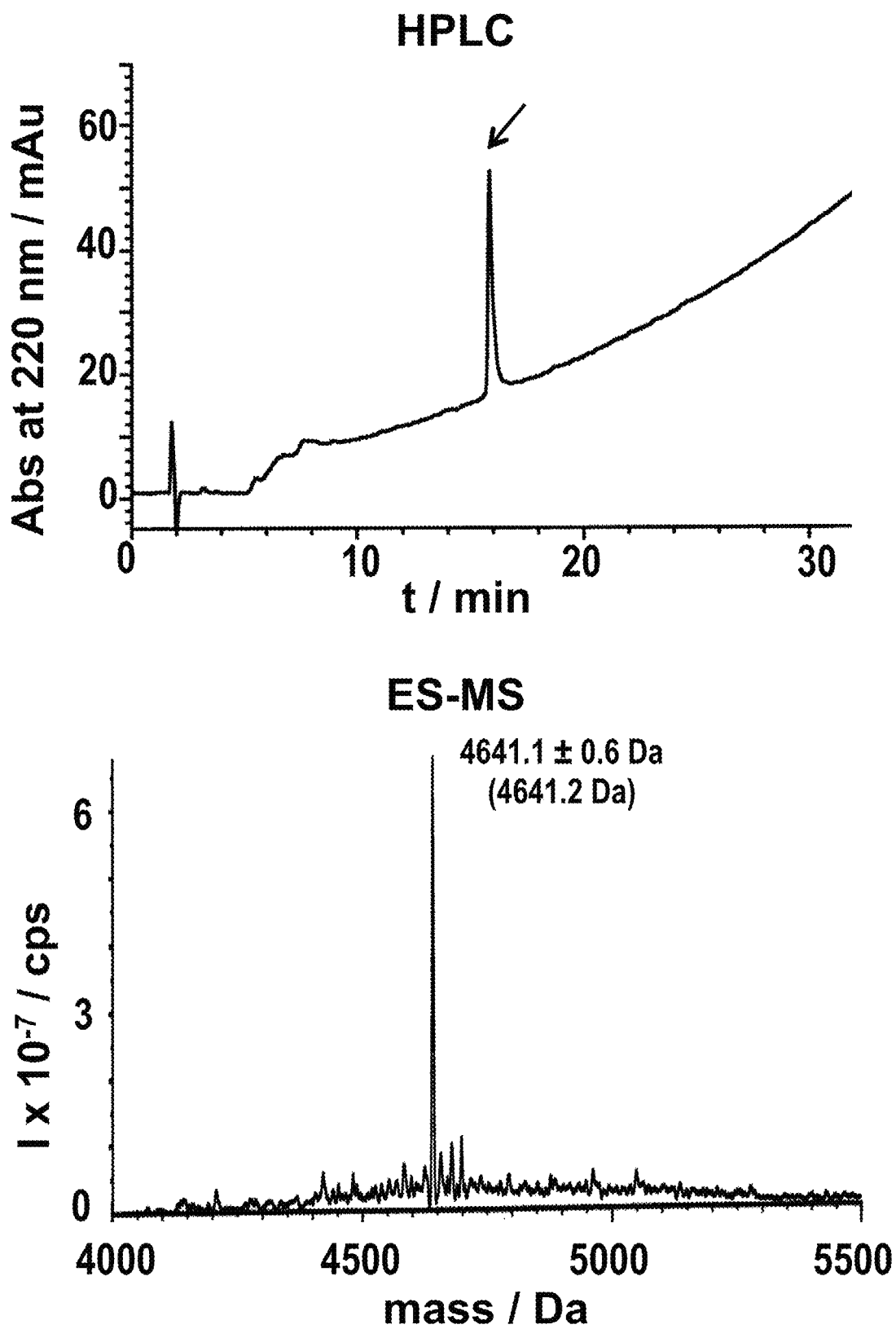
FIG. 6 shows analytical reverse-phase C18-HPLC trace and ES-MS (deconvoluted) of linear Salkylated MCo-AT1-7. HPLC analysis was performed using a linear gradient of 0-70% solvent B over 30 minutes.

The linear and fully reduced cyclotide precursor was purified by semi-preparative HPLC using a linear gradient of 15-35% solvent B over 30 min. The purified peptide was characterized by HPLC and ES-MS [Expected mass: 4641.2 Da. Observed mass: 4641.1±0.6 Da] (FIG. 6).

NMR Spectroscopy

NMR samples were prepared by dissolving cyclotides into 80 mM potassium phosphate pH 6.0 in 90% H$_2$O/10% $^2$H$_2$O (v/v) to a concentration of approximately 0.5 mM. All $^1$H NMR data were recorded on Bruker Avance II 700 MHz spectrometer equipped with the TXI cryoprobe. Data were acquired at 298 K, and 2,2-dimethyl-2-silapentane-5-sulfonate, DSS, was used as an internal reference. The carrier frequency was centered on the water signal, and the solvent was suppressed by using WATERGATE pulse sequence. $^1$H, $^1$HTOCSY (spin lock time 80 ms) and $^1$H, $^1$H-NOESY (mixing time 150 ms) spectra were collected using 4096 t$_2$ points and 256 t$_1$ of 64 transients. Spectra were processed using Topspin 2.1 (Bruker). Each 2D-data set was apodized by 90°-shifted sinebell-squared in all dimensions, andzero filled to 4096×512 points prior to Fourier transformation. Assignments for H$^\alpha$ (H—C$^\alpha$) and H' (H—N$^\alpha$) protons of folded MCo-AT1-7 (Table 2) were obtained using standard procedures.

Biological Activity of Cyclotide MCo-AT1-7

CHO cells stably transfected with pTEJ-8 vector expressing recombinant human MAS1 clone are grown to confluency. After washing, cells are incubated for a short time in 700 µL of supplemented Tyrode's salts containing 10 µM 2-phenyl-4,4,5,5-tetramethylimidazoline-1-oxyl-3-oxide (PTIO), 100 µM 2,3-diaminonaftalene (DAN), and 1 mM L-arginine. When using antagonist for competition assays, cells are exposed to MAS1 antagonist A779 (D-Ala$^7$-AT 1-7) at 0.1 µM for 15 min before addition of the cyclotides to be tested. Different concentrations of the cyclotides to be analyzed are added to the cell medium and the plates are agitated for 1 min before being placed into the incubator for 2 hours. After 2 hours, the cellular supernatants are transferred to opaque 96 well plates, and the amount of released NO is measured by fluorescence (λex=380 nm, λem=425 nm).

Serum Stability

Human serum was spun down at 15,000 rpm for 10 min to separate the lipid components. Peptides (about 15 µg dissolved in 15 µl PBS) were mixed with 150 µl human serum and incubated in a 37° C. water bath. Aliquot samples (15 µL) were taken at different time points and serum protein were precipitated with about 70% MeCN at 4° C. for 10 min. The supernatant was separated, lyophilized, dissolved in 5% MeCN in water containing 0.1% formic acid, and analyzed by HPLC-MS/MS.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains. Several aspects of the invention are listed below.

Cyclotide Treatment of Lung Cancer In Vitro

To test the effectiveness of the cyclotides and peptides disclosed herein in the treatment of cancer, human adenocarcinoma cell lines such as SK-LU-1 and A549, as well as non-small lung cancer cell lines such as SK-MES-1 will treated be treated with serum containing MCo-AT1-7 or a control MCo-TI-I cyclotide. Serum-stimulated growth of the cell lines treated with cyclotides will be compared. A MCo-AT1-7 dose and/or time specific reduction in growth or increase in cell death of one or more cell lines will indicate that the cyclotide has a significant inhibitory effect. Cells treated with an effective amount of MCo-AT1-7 may exhibit reduced DNA synthesis, reduced cell number, increased apoptosis, reduced metabolic activity, and/or a reduction in proliferation (as measured by cell cycle analysis) relative to cells treated with the control cyclotide.

For example, to measure the effect of MCo-AT1-7 on lung cancer cell proliferation, a growth assay will be performed. Cyclotides with AT1-7 grafts will be prepared according to methods disclosed herein. SK-LU-1, A549, and/or SK-MES-1 will be seeded into tissue culture plates in the presence of about 1% FBS. Every 12 or every 24 hours following initial plating, cells will be treated with about 100 pM, about 500 pM, about 1 nM, about 10 nM, about 20 nM, about 50 nM, about 100 nM, about 200 nM, about 500 nM, about 800 nM, about 1 µM, about 2 µM, about 10 µM MCo-AT1-7 or control cyclotide in phosphate-buffered saline or PBS alone. Cells will be removed and counted on days 0.5, 1, 1.5, 2, 3, 4, 6, 8, 10, 12, 14, 16, and 18 using trypsin with EDTA and a hemocytometer. Additionally, cells may be pre-treated with cyclotides in the growth medium for about 30 minutes, about an hour, about 2 hours, about 4 hours, about 6 hours, about 12 hours, about 24 hours, about 48 hours, or about 72 hours prior to the addition of serum in order to test chemopreventative effects of MCo-AT1-7. To measure cell death, dye uptake and/or Annexin V assays will be performed on harvested cells. Additionally, BrdU incorporation assays coupled with flow cytometry and/or immunofluorescence will used to measure cell proliferation in cells treated with cyclotides as described above. To measure the levels of DNA synthesis, a thymidine incorporation assay will be used on quiescent cells. Tritiated thymidine will be added to the growth medium of semi-confluent cells treated with serum and cyclotides as above. After about 4 hours of thymidine exposure, the level of incorporated thymidine will be determined by liquid scintillation spectrometry. The results of these in vitro studies will indicate that MCo-AT1-7 inhibits lung cancer cell growth and validate MCo-AT1-7 as a novel chemopreventive and/or chemotherapeutic treatment for lung cancer.

Cyclotide Treatment of Lung Cancer In Vivo

A human lung tumor xenograft model will be used to test the inhibitory effects of the MCo-AT1-7 on lung cancer in vivo. Actively proliferating human lung cancer cells (e.g. SK-LU-1, A549, and/or SK-MES-1) will be inoculated into athymic mice. The dose of cancer cells may vary by cell line but will be about $1\times10^2$ cells, about $1\times10^3$ cells, about $1\times10^4$ cells, about $1\times10^5$ cells, about $1\times10^6$ cells, about $1\times10^7$ cells, about $1\times10^8$ cells, or about $1\times10^9$ cells per mouse. After about 7 days, about 14 days, about 21 days, about 28 days, about 35 days, about 42 days, and/or about 48 days, mice will be treated with MCo-AT1-7 or a control MCo-TI-I cyclotide. The number of days prior to initiating cyclotide treatment may be determined based on a threshold minimum tumor size such (e.g. about 10 mm³, 100 mm³, or about 1000 mm³). The cyclotides will be prepared as disclosed herein. Cyclotides may be administered to the mice by any method in the art including, but not limited to, osmotic mini-pump (Durect Corp.), intravenous injection, intraarterial injection, intraperitoneal injection, or inhalation. The dose may vary by method of administration. Non limiting examples of an effective dose for delivery via an osmotic pump are about 100 ng/kg/hr, about 500 ng/kg/hr, about 1 µg/kg/hr, about 10 µg/kg/hr, about 20 µg/kg/hr, about 30 µg/kg/hr, about 50 µg/kg/hr, about 50 µg/kg/hr, 100 µg/kg/hr, or about 1 mg/kg/hr. The pump may also contain heparin (about 25 U/mL) or an equivalent anticoagulant. Chemotherapeutic agents such as cisplatin, carboplatin, paclitaxel, gemcitabine, or docetaxel may be co-administered with the cyclotides. The mice will be anesthetized by inhalation with isoflurane. Administration may occur over a period of about 1 hour, about 2 hours, about 4 hours, about 6 hours, about 8 hours, about 12 hours, or about 24 hours and may be repeated daily, every 2 days, every 3 days, every 4 days, every 5 days, every 6 days, every 7 days, or every 14 days. Inhibition of tumor growth will be determined by harvesting tumors from MCo-AT1-7 or control treated mice, measuring tumor size, and performing immunohistochemistry to assay for cancer biomarkers, proliferation/cell cycle markers, cell death markers, and/or human cell markers. Prior to sacrificing mice, the mice may be administered BrDU to perform cell cycle assays on the tumor cells. Tumors from mice treated with MCo-AT1-7 may be smaller in size, exhibit reduced proliferation, and/or exhibit increased cell death relative to control-treated mice.

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention such as for example, embodiments described in Appendix A attached hereto. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

1. Gallagher, P. E.; Cook, K.; Soto-Pantoja, D.; Menon, J.; Tallant, E. A. Angiotensin peptides and lung cancer. *Current cancer drug targets* 2011, 11, 394-404.
2. Menon, J.; Soto-Pantoja, D. R.; Callahan, M. F.; Cline, J. M.; Ferrario, C. M.; Tallant, E. A.; Gallagher, P. E. Angiotensin-(1-7) inhibits growth of human lung adenocarcinoma xenografts in nude mice through a reduction in cyclooxygenase-2. *Cancer Res* 2007, 67, 2809-2815.
3. Gallagher, P. E.; Tallant, E. A. Inhibition of human lung cancer cell growth by angiotensin-(1-7). *Carcinogenesis* 2004, 25, 2045-2052.
4. Tallant, E. A.; Clark, M. A. Molecular mechanisms of inhibition of vascular growth by angiotensin-(1-7). *Hypertension* 2003, 42, 574-579.
5. Tallant, E. A.; Diz, D. I.; Ferrario, C. M. State-of-the-art lecture. Antiproliferative actions of angiotensin-(1-7) in vascular smooth muscle. *Hypertension* 1999, 34, 950-957.

6. Craik, D. J.; Daly, N. L.; Bond, T.; Waine, C. Plant cyclotides: A unique family of cyclic and knotted proteins that defines the cyclic cystine knot structural motif. *J Mol Biol* 1999, 294, 1327-1336.
7. Daly, N. L.; Rosengren, K. J.; Craik, D. J. Discovery, structure and biological activities of cyclotides. *Adv Drug Deliv Rev* 2009, 61, 918-930.
8. Gould, A.; Ji, Y.; Aboye, T. L.; Camarero, J. A. Cyclotides, a novel ultrastable polypeptide scaffold for drug discovery. *Curr Pharm Des* 2011, 17, 4294-4307.
9. Puttamadappa, S. S.; Jagadish, K.; Shekhtman, A.; Camarero, J. A. Backbone dynamics of cyclotide mcoti-i free and complexed with trypsin. *Angew Chem Int EdEngl* 2010, 49, 7030-7034.
10. Puttamadappa, S. S.; Jagadish, K.; Shekhtman, A.; Camarero, J. A. Erratum in: Backbone dynamics of cyclotide mcoti-i free and complexed with trypsin. *Angew Chem Int Ed Engl* 2011, 50, 6948-6949.
11. Austin, J.; Kimura, R. H.; Woo, Y. H.; Camarero, J. A. In vivo biosynthesis of an ala-scan library based on the cyclic peptide sfti-1. *Amino Acids* 2010, 38, 1313-1322.
12. Huang, Y. H.; Colgrave, M. L.; Clark, R. J.; Kotze, A. C.; Craik, D. J. Lysine-scanning mutagenesis reveals an amendable face of the cyclotide kalata b1 for the optimization of nematocidal activity. *J Biol Chem* 2010, 285, 10797-10805.
13. Simonsen, S. M.; Sando, L.; Rosengren, K. J.; Wang, C. K.; Colgrave, M. L.; Daly, N. L.; Craik, D. J. Alanine scanning mutagenesis of the prototypic cyclotide reveals a cluster of residues essential for bioactivity. *J Biol Chem* 2008, 283, 9805-9813.
14. Garcia, A. E.; Camarero, J. A. Biological activities of natural and engineered cyclotides, a novel molecular scaffold for peptide-based therapeutics. *Curr Mol Pharmacol* 2010, 3, 153-163.
15. Contreras, J.; Elnagar, A. Y.; Hamm-Alvarez, S. F.; Camarero, J. A. Cellular uptake of cyclotide mcoti-i follows multiple endocytic pathways. *J Control Release* 2011, 155, 134-143.
16. Cascales, L.; Henriques, S. T.; Kerr, M. C.; Huang, Y. H.; Sweet, M. J.; Daly, N. L.; Craik, D. J. Identification and characterization of a new family of cell-penetrating peptides: Cyclic cell penetrating peptides. *J Biol Chem* 2011, 286, 36932-36943.
17. Ji, Y.; Majumder, S.; Millard, M.; Borra, R.; Bi, T.; Elnagar, A. Y.; Neamati, N.; Shekhtman, A.; Camarero, J. A. In vivo activation of the p53 tumor suppressor pathway by an engineered cyclotide. *J Am Chem Soc* 2013, 135, 11623-11633.
18. Henriques, S. T.; Craik, D. J. Cyclotides as templates in drug design. *Drug Discov Today* 2010, 15, 57-64.
19. Aboye, T. L.; Ha, H.; Majumder, S.; Christ, F.; Debyser, Z.; Shekhtman, A.; Neamati, N.; Camarero, J. A. Design of a novel cyclotide-based cxcr4 antagonist with anti-human immunodeficiency virus (hiv)-1 activity. *J Med Chem.* 2012, 55, 10729-10734.
20. Chan, L. Y.; Gunasekera, S.; Henriques, S. T.; Worth, N. F.; Le, S. J.; Clark, R. J.; Campbell, J. H.; Craik, D. J.; Daly, N. L. Engineering pro-angiogenic peptides using stable, disulfiderich cyclic scaffolds. *Blood* 2011, 118, 6709-6717.
21. Sommerhoff, C. P.; Avrutina, O.; Schmoldt, H. U.; Gabrijelcic-Geiger, D.; Diederichsen, U.; Kolmar, H. Engineered cystine knot miniproteins as potent inhibitors of human mast cell tryptase beta. *J Mol Biol* 2010, 395, 167-175.
22. Wang, Y.; Qian, C.; Roks, A. J.; Westermann, D.; Schumacher, S. M.; Escher, F.; Schoemaker, R. G.; Reudelhuber, T. L.; van Gilst, W. H.; Schultheiss, H. P., et al. Circulating rather than cardiac angiotensin-(1-7) stimulates cardioprotection after myocardial infarction. *Circ Heart Fail* 2010, 3, 286-293.
23. Loot, A. E.; Roks, A. J.; Henning, R. H.; Tio, R. A.; Suurmeijer, A. J.; Boomsma, F.; van Gilst, W. H. Angiotensin-(1-7) attenuates the development of heart failure after myocardial infarction in rats. *Circulation* 2002, 105, 1548-1550.
24. Iusuf, D.; Henning, R. H.; van Gilst, W. H.; Roks, A. J. Angiotensin-(1-7): Pharmacological properties and pharmacotherapeutic perspectives. *European journal of pharmacology* 2008, 585, 303-312.
25. Hernandez, J. F.; Gagnon, J.; Chiche, L.; Nguyen, T. M.; Andrieu, J. P.; Heitz, A.; Trinh Hong, T.; Pham, T. T.; Le Nguyen, D. Squash trypsin inhibitors from *Momordica cochinchinensis* exhibit an atypical macrocyclic structure. *Biochemistry* 2000, 39, 5722-5730.
26. Jagadish, K.; Gould, A.; Borra, R.; Majumder, S.; Mushtaq, Z.; Shekhtman, A.; Camarero, J. A. Recombinant expression and phenotypic screening of a bioactive cyclotide against alpha-synuclein-induced cytotoxicity in baker's yeast. *Angew Chem Int EdEngl* 2015, 54, 8390-8394.
27. Jagadish, K.; Borra, R.; Lacey, V.; Majumder, S.; Shekhtman, A.; Wang, L.; Camarero, J. A. Expression of fluorescent cyclotides using protein trans-splicing for easy monitoring of cyclotide-protein interactions. *Angew Chem Int EdEngl* 2013, 52, 3126-3131.
28. Borra, R.; Camarero, J. A. Recombinant expression of backbone-cyclized polypeptides. *Biopolymers* 2013, 100, 502-509.
29. Austin, J.; Wang, W.; Puttamadappa, S.; Shekhtman, A.; Camarero, J. A. Biosynthesis and biological screening of a genetically encoded library based on the cyclotide mcoti-i. *Chembiochem* 2009, 10, 2663-2670.
30. Durik, M.; van Veghel, R.; Kuipers, A.; Rink, R.; Haas Jimoh Akanbi, M.; Moll, G.; Danser, A. H.; Roks, A. J. The effect of the thioether-bridged, stabilized angiotensin-(1-7) analogue cyclic ang-(1-7) on cardiac remodeling and endothelial function in rats with myocardial infarction. *Int J Hypertens* 2012, 2012, 536426.
31. Kluskens, L. D.; Nelemans, S. A.; Rink, R.; de Vries, L.; Meter-Arkema, A.; Wang, Y.; Walther, T.; Kuipers, A.; Moll, G. N.; Haas, M. Angiotensin-(1-7) with thioether bridge: An angiotensin-converting enzyme-resistant, potent angiotensin-(1-7) analog. J Pharmacol Exp Ther 2009, 328, 849-854.
32. Contreras, J.; Elnagar, A. Y. O.; Hamm-Alvarez, S. F.; Camarero, J. A. Cellular uptake of cyclotide mcoti-i follows multiple endocytic pathways. J. Control. Release 2011, 155, 134-143.
33. Camarero, J. A.; Mitchell, A. R. Synthesis of proteins by native chemical ligation using fmoc-based chemistry. Protein Pept Lett 2005, 12, 723-728.
34. Cavanagh, J.; Rance, M. Suppression of cross relaxation effects in tocsy spectra via a modified disi-2 mixing sequence. J. Magn. Res. 1992, 96, 670-678.
35. Wuthrich, K. Nmr of proteins and nucleic acids. 1986.
36. Felizmenio-Quimio, M. E.; Daly, N. L.; Craik, D. J. Circular proteins in plants: Solution structure of a novel macrocyclic trypsin inhibitor from *Momordica cochinchinensis*. J Biol Chem 2001, 276, 22875-22882.
37. Aboye, T., Meeks, C. J., Majumder, S. Shekhtman, A., Rodgers, K., and Camarero, J. Design of a MCoTI-based cyclotide with Angiotensin (1-7)-like activity. Molecules 2016 Jan. 26; 21(2): 152.

What is claimed is:

1. A cyclotide comprising:
   a) a cyclotide backbone selected from the group consisting of SEQ ID NOs: 2, 4, and 5 and
   b) an angiotensin polypeptide consisting of the sequence of SEQ ID NO: 14,
   wherein the cyclotide maintains a biological activity of an angiotensin polypeptide.

2. The cyclotide of claim 1, further comprising a label or purification marker.

3. A composition comprising the cyclotide of claim 1 and a carrier.

4. The composition of claim 3, wherein the carrier is a pharmaceutically acceptable carrier.

5. The composition of claim 4, further comprising a therapeutic agent.

6. A plurality of cyclotides of claim 1.

7. The plurality of claim 6, wherein the amino acid sequences of the plurality are the same or different from each other.

8. A composition comprising the plurality of claim 7 and a carrier.

9. The composition of claim 8, wherein the carrier is a pharmaceutically acceptable carrier.

10. The composition of claim 8, further comprising a therapeutic agent.

11. A cyclotide comprising a sequence selected from the group consisting of SEQ ID NOs: 17, 18, 19, and 20.

12. An isolated polynucleotide encoding the cyclotide of claim 1.

13. A composition comprising an isolated polynucleotide of claim 12 and a carrier.

14. The composition of claim 13, wherein the carrier is a pharmaceutically acceptable carrier.

15. A complement of the polynucleotide of claim 12.

16. An isolated polynucleotide of claim 15, further comprising a label or a purification marker.

17. A vector comprising the isolated polynucleotide of claim 12.

18. An isolated host cell comprising the cyclotide of claim 1.

19. The isolated host cell of claim 18, wherein the cell is a eukaryotic cell or a prokaryotic cell.

20. An isolated host cell comprising the polynucleotide of claim 12.

21. The isolated host cell of claim 20, wherein the isolated host cell is a eukaryotic cell or a prokaryotic cell.

22. The isolated host cell of claim 21, wherein the cell is a prokaryotic cell.

23. A method for producing a recombinant cyclotide polypeptide comprising growing the isolated host cell of claim 20 under conditions to express the polynucleotide.

24. The method of claim 23, further comprising purifying the polypeptide.

25. A method for any one of: promoting vasodilation in a tissue, inhibiting the proliferation of a cell or tissue, or inhibiting angiogenesis, comprising contacting the cell or tissue with a cyclotide of claim 1, wherein the contacting is in vitro or in vivo.

26. The method of claim 25, wherein the cell or tissue is a mammalian cell or tissue.

27. The method of claim 26, wherein the mammalian cell or tissue is a human cell or tissue.

28. A method for inhibiting the growth of a tumor cell comprising contacting the tumor cell with a cyclotide of claim 1, wherein the contacting is in vitro or in vivo.

29. The method of claim 28, wherein the tumor cell expresses MAS 1.

30. The method of claim 28, wherein the tumor cell is a lung cancer tumor cell or a breast cancer tumor cell.

31. The method of claim 28, wherein the tumor cell is a mammalian cell, optionally a human cell.

32. A method for any one of: promoting vasodilation in a tissue, inhibiting the proliferation of a cell or tissue, treating myocardial infarction or inhibiting angiogenesis, in a subject in need thereof, comprising administering to a subject in need thereof, an effective amount of cyclotide of claim 1.

33. A method for inhibiting the growth of a tumor in a subject in need thereof, comprising administering to the subject an effective amount of the cyclotide of claim 1.

34. The method of claim 33, wherein the tumor expresses MAS 1.

35. The method of claim 34, wherein the tumor is a lung cancer tumor or breast cancer tumor.

36. The method of claim 33, wherein the subject is a mammal, optionally a human.

* * * * *

UNITED STATES PATENT AND TRADEMARK OFFICE
CERTIFICATE OF CORRECTION

PATENT NO. : 10,988,522 B2
APPLICATION NO. : 16/232985
DATED : April 27, 2021
INVENTOR(S) : Julio A. Camarero Palao, Teshome L. Aboye and Kathleen E. Rodgers It is certified that error appears in the above-identified patent and that said Letters Patent is hereby corrected as shown below:

In the Specification

In Column 1, Line 19, please delete "R01-GM113363" and insert -- R01-GM113636 --

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*